(12) United States Patent
Kreutter et al.

(10) Patent No.: US 7,550,474 B2
(45) Date of Patent: *Jun. 23, 2009

(54) SUBSTITUTED PHENYL ACETAMIDES AND THEIR USE AS PROTEASE INHIBITORS

(75) Inventors: Kevin D. Kreutter, Plainsboro, NJ (US); Lily Lee, New York, NY (US); Tianbao Lu, Churchville, PA (US); Venkatraman Mohan, Plainsboro, NJ (US); Sharmila Patel, Jamison, PA (US); Hui Huang, Monroe, NJ (US); Guozhang Xu, Langhorne, PA (US); Mark Fitzgerald, Atco, NJ (US)

(73) Assignee: Johnson & Johnson Pharmaceuticals Research & Development, L.L.C., Raritan, NJ (US)

( * ) Notice: Subject to any disclaimer, the term of this patent is extended or adjusted under 35 U.S.C. 154(b) by 814 days.

This patent is subject to a terminal disclaimer.

(21) Appl. No.: 10/816,544

(22) Filed: Apr. 1, 2004

(65) Prior Publication Data

US 2004/0254166 A1    Dec. 16, 2004

Related U.S. Application Data

(60) Provisional application No. 60/461,421, filed on Apr. 10, 2003.

(51) Int. Cl.
*A61K 31/435* (2006.01)
*C07D 221/02* (2006.01)
*C07D 335/00* (2006.01)
*C07D 309/00* (2006.01)
*C07C 321/00* (2006.01)

(52) U.S. Cl. .................. 514/277; 546/112; 546/152; 549/13; 549/356; 564/162

(58) Field of Classification Search ............ 514/217.12, 514/227.5, 237.5, 252.12, 317, 365, 374, 514/400, 408, 618, 277; 540/607; 544/162, 544/399, 59; 546/233, 112, 152; 548/200, 548/235, 338.1, 577; 564/162; 549/13, 356
See application file for complete search history.

(56) References Cited

U.S. PATENT DOCUMENTS

| | | | |
|---|---|---|---|
| 4,418,052 A | 11/1983 | Wong | 424/1.1 |
| 4,499,082 A | 2/1985 | Shenvi et al. | 514/2 |
| 4,652,440 A | 3/1987 | Paik et al. | 424/1.1 |
| 4,727,064 A | 2/1988 | Pitha | 514/58 |
| 4,764,604 A | 8/1988 | Muller | 536/103 |
| 4,957,939 A | 9/1990 | Gries et al. | 514/492 |
| 4,980,148 A | 12/1990 | Dean | 424/9 |
| 5,011,686 A | 4/1991 | Pang | 424/94.1 |
| 5,024,829 A | 6/1991 | Berger et al. | 424/1.1 |
| 5,024,998 A | 6/1991 | Bodor | 514/58 |
| 5,122,361 A | 6/1992 | Kung et al. | 424/1.1 |
| 5,466,811 A | 11/1995 | Alexander | 546/283 |
| 5,656,600 A | 8/1997 | Abelman et al. | 514/13 |
| 5,786,515 A | 7/1998 | Dolling et al. | 568/316 |
| 6,521,663 B2 * | 2/2003 | Pan et al. | 514/518 |
| 2002/0193398 A1 | 12/2002 | Barrow et al. | 514/300 |

FOREIGN PATENT DOCUMENTS

| | | |
|---|---|---|
| CA | 2 164 684 | 6/1996 |
| EP | 0 470 578 A1 | 2/1992 |
| EP | 0 604 022 A1 | 6/1994 |
| EP | 0 761 521 B1 | 12/2000 |
| WO | WO 96/11668 | 4/1996 |
| WO | WO 96/32143 | 10/1996 |
| WO | WO 96/38136 | 12/1996 |
| WO | WO 97/01338 | 1/1997 |
| WO | WO 99/26926 | 6/1999 |
| WO | WO 01/68605 A1 | 9/2001 |
| WO | WO 02/28825 A2 | 4/2002 |

OTHER PUBLICATIONS

Ashwood, M.S. et al., "Copper-Mediated Reeaction of 2-Halopyridines with Ethyl Bromodifluoroacetate", *Tetrahedron Letters*, 2002, 43, 9271-9273.

(Continued)

*Primary Examiner*—Taylor Victor Oh
(74) *Attorney, Agent, or Firm*—Woodcock Washburn LLP

(57) ABSTRACT

Phenyl acetamide compounds are described, including compounds of Formula I:

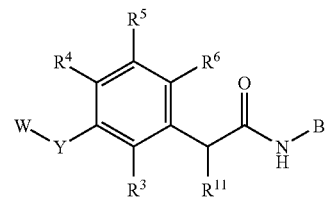

or a solvate, hydrate or pharmaceutically acceptable salt thereof; wherein $R^3$-$R^6$, $R^{11}$, B, Y and W are set forth in the specification. The compounds of the invention are potent inhibitors of proteases, especially trypsin-like serine proteases, such as thrombin and factor Xa. Compositions for inhibiting loss of blood platelets, inhibiting formation of blood platelet aggregates, inhibiting formation of fibrin, inhibiting thrombus formation, and inhibiting embolus formation are described. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents. Additionally, the compounds can be detectably labeled and employed for in vivo imaging of thrombi.

42 Claims, No Drawings

OTHER PUBLICATIONS

Baugh, R.J. et al., "Human Leukocyte Granule Elastase: Rapid Isolation and Characterization", *Biochemistry*, 1979, 15(4),836-841.

Bergeron, R.J. et al., "Total Synthesis of (+_)-15-Deoxyspergualin", *J. Org. Chem.*, 1987, 52, 1700-1703.

Bernatowicz, M.S. et al., "Urethane Protected Derivatives of 1-Guanylpyrazole for the Mild and Efficient Preparation of Guanidines", *Tetrahedron Letters*, 1993, 34(21),3389-3392.

Claeson, G., "Synthetic Peptides and Peptidomimetics as Substrates and Inhibitors of Thrombin and Other Proteases in the Blood Coagulation System", *Blood Coagulation and Fibrinolysis*, 1994, 5. 411-436.

Clagett-Dame, M et al., "Preparation of an Affinity Chromatography Matrix for the Selective Purfication of the Dopamine D2 Receptor from Bovine Striatal Membranes", *Biochima. Biophysica. Acta*, 1989, 986, 271-280.

Couglin, S.R., "Molecular Mechanisms of Thrombin Signaling", *Seminars in Hematology*, 1994, 31(4). 270-277.

Cuypers, H.T. et al., "Sulhydryl Content of Bovine Eye Lens Leucine Aminopeptidase", *The Journal of Biological Chemistry* 1982, 257(12), 7086-7091.

Dalcanale, E. et al., "Selective Oxidation of Aldehydes to Carboxylic Acids with Sodium Chlorite-Hydrogen Peroxide", *J. Org Chem.*, 1986, 51, 567-569.

de Roos, A. et al., "Myocardial Infarct Sizing and Assessment of Reperfusion by Magnetic Resonance Imaging: A Review", *International Journal of Cardiac. Imaging*, 1991, 7, 133-138.

Eto, H. et al., "New Antifungal, 1,2,4-Triazoles with Difluoro(heteroaryl) Methyl Moiety", *Chem Pharm Bull.*, 2000, 48, 982-990.

Feng, D.M. et al., "Discovery of a Novel, Selective, and Orally Bioavailable Class of Thrombin Inhibitors Incorporating Aminopyridyl Moieties at the P1 Position", *J. Med Chem*, 1997, 40, 3726-3733.

Harker, L.A., "Strategies for Inhibiting the Effects of Thrombin", *Blood Coagulation and Fibrinolysis 5 (Suppl 1)*, 1994, S47-S64.

Khaw, B.A. et al., "Myocardial Infarct Imaging of Antibodies to Canine Cardiac Myosin with Indium-111-Diethylentriamine Pentaacetic Acid", *Science*, 1980, 209, 295-297.

Lefkovits, J. et al., "Direct Thrombin Inhibitors in Cardiovascular Medicine", *Circulation*, 1994, 90(3), 1522-1536.

Mitsunobu, O., "The Use of Diethyl Azodicarboxylate and Triphenylphosphine in Synthesis and Transformation of Natural Products", *Synthesis*, 1981, 1, 1-28.

Powers, W.J. et al., "Indium-III Platelet Scintigraphy in Cerebrovascular Disease", *Neurology*, 1982, 32, 938-943.

Sanderson, P.E.J. et al., "Efficacious, Orally Bioavailable Thrombin Inhibitors Based on 3-Aminopyridinone or 3-Aminopyrazinone Acetamide Peptidomimetic Templates", *J. Med Chem*, 1998, 41, 4466-4474.

Sato, K. et al., "Synthesis of Alkenyl-and Aryldifluoracetate Using a Copper Complex from Ethyl Bromodifluoracetate", *Chem. Pharm Bull.*, 1999, 47(7), 1013-1016.

Saulnier, M.G. et al. "An Efficient Method for the Synthesis of Guanidino Prodrugs", *Bioorganic & Medicinal Chemistry Letters*, 1994, 4(16), 1985-1990.

Szilagyi, G. et al., "Synthesis and Antihypertensive Activity of Novel 6-Substituted-3-Pyridazinylhydrazones", *European J. Med. Chem.*, 1984, 19(2), 111-117.

Thakur, M.L. et al, "Indium-III Labeled Platelets: Studies on Preparation and Evaluation of In Vitro and In Vivo Functions", *Thrombosis Research.*, 1976, 9, 345-357.

Tillyer, R. et al., Efficient Synthesis of α-Chloro Ketones via Reaction of Organometallic Reagents with N-Methoxy-N-Methylchloroacetamide, *Synlett*, 1996, 225-226.

*United States Pharmacopeia/ National Formulary-USP*, 1995, United States Pharmacopeial Convention, Inc.; Rockville, Maryland, p. 1636.

\* cited by examiner

SUBSTITUTED PHENYL ACETAMIDES AND THEIR USE AS PROTEASE INHIBITORS

CROSS REFERENCE TO RELATED APPLICATIONS

This application claims priority to U.S. Provisional Application Ser. No. 60/461,421, filed Apr. 10, 2003, which is incorporated herein by reference in its entirety.

FIELD

The present invention relates to novel compounds that function as proteolytic enzyme inhibitors, and particularly to a new class of thrombin inhibitors.

BACKGROUND

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs*, Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons. Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4): 270-277 (1994)), and autoamplifies its own production through a feedback mechanism. Thus, inhibitors of thrombin function have therapeutic potential in a host of cardiovascular and non-cardiovascular diseases.

Factor Xa is another serine protease in the coagulation pathway. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411-436 (1994); Harker, *Blood Coagulation and Fibrinolysis* 5 (*Suppl* 1):S47-S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522-1536 (1994); Harker, *Blood Coagulation and Fibrinolysis* 5 (*Suppl* 1):S47-S58 (1994)).

In vivo diagnostic imaging methods for intravascular thrombi have been previously reported. These imaging methods use compounds that are detectably labeled with radioactive or paramagnetic atoms. For example, platelets labeled with the gamma emitter, In-111, can be employed as an imaging agent for detecting thrombi (Thakur, M. L. et al., *Thromb Res.* 9:345 (1976); Powers et al., *Neurology* 32:938 (1982)). The thrombolytic enzyme streptokinase labeled with Tc-99m has been proposed as an imaging agent (Wong, U.S. Pat. No. 4,418,052 (1983)). The fibrin-binding domains of *Staphylococcus aureus* derived protein A labeled with the gamma emitters, I-125 and I-131, have been proposed as imaging agents (Pang, U.S. Pat. No. 5,011,686 (1991)). Monoclonal antibodies having specificity for fibrin (in contrast to fibrinogen) and labeled with Tc-99m have been proposed as imaging agents (Berger et al., U.S. Pat. No. 5,024,829 (1991); Dean et al., U.S. Pat. No. 4,980,148 (1990)). The use of the paramagnetic contrasting agent, gadolinium diethylenetriaminepentaacetic acid in magnetic resonance imaging of patients treated by thrombolysis for acute myocardial infarction has been reported (De Roos, A. et al., *Int. J. Card. Imaging* 7:133 (1991)). Radiolabeled and paramagnetically labeled alpha-ketoamide derivatives have also been proposed as thrombus imaging agents (Abelman et al., U.S. Pat. No. 5,656,600).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

SUMMARY

The present invention is directed, inter alia, to novel substituted phenyl acetamides having Formula I (below). Also provided are processes for preparing compounds of Formula I. The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin, or are intermediates useful for forming compounds having antithrombotic activity. Also provided are methods of inhibiting or treating aberrant proteolysis in a mammal and methods of treating thrombosis, ischemia, stroke, restenosis or inflammation in a mammal by administering an effective amount of a compound of Formula I.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions can optionally include anticoagulants, antiplatelet agents, and thrombolytic agents. The compositions can be added to blood, blood products, or mammalian organs in order to effect the desired inhibitions.

Also provided are methods of inhibiting or treating aberrant proteolysis in a mammal, and methods for treating myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

DETAILED DESCRIPTION

Compounds of the present invention include compounds of Formula I:

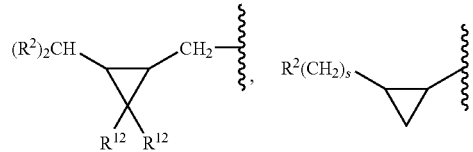

or a solvate, hydrate or pharmaceutically acceptable salt thereof; wherein:

W is $R^1$ or $R^1S(O_2)$;

$R^1$ is $R^2$, $R^2(CH_2)_tC(R^{12})_2$, where t is 0-3, and each $R^{12}$ can be the same or different, $(R^2)(OR^{12})CH(CH_2)_p$, where p is 1-4, $(R^2)_2(OR^{12})C(CH_2)_p$, where p is 1-4, $R^2C(R^{12})_2(CH_2)_t$, wherein t is 0-3, and each $R^{12}$ can be the same or different, wherein $(R^{12})_2$ can also form a ring with C represented by $C_{3-9}$ cycloalkyl, $R^2CF_2C(R^{12})_2(CH_2)_q$, wherein q is 0-2, and each $R^{12}$ can be the same or different, wherein $(R^{12})_2$ can also form a ring with C represented by $C_{3-9}$ cycloalkyl, $R^2CH_2C(R^{12})_2(CH_2)_q$, wherein q is 0-2, and each $R^{12}$ can be the same or different, wherein $(R^{12})_2$ can also form a ring with C represented by $C_{3-9}$ cycloalkyl, $(R^2)_2CH(CH_2)_r$, where r is 0-4 and each $R^2$ can be the same or different, and wherein $(R^2)_2$ can also form a ring with CH represented by $C_{3-9}$ cycloalkyl, $C_{7-12}$ bicylic alkyl, $C_{10-16}$ tricylic alkyl, or a 5- to 7-membered mono- or bicyclic heterocyclic ring which can be saturated or unsaturated, and which contains from one to three heteroatoms selected from the group consisting of N, O and S, $R^2O(CH_2)_p$, wherein p is 2-4, $(R^2)_2CF(CH_2)_r$, wherein r is 0-4 and each $R^2$ can be the same or different, wherein $(R^2)_2$ can also form a ring with C represented by $C_{3-9}$ cycloalkyl, $C_{7-12}$ bicyclic alkyl, $C_{10-16}$ tricyclic alkyl, or a 5- to 7-membered mono- or bicyclic heterocyclic ring which can be saturated or unsaturated, and which contains from one to three heteroatoms selected from the group consisting of N, O and S,

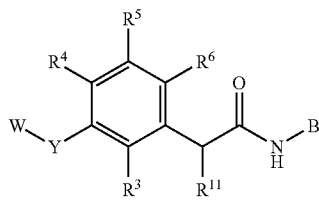

where s is 0 or 1, or $R^2CF_2C(R^{12})_2$;

$R^2$ is phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, $COOH$, $CO_2R^{21}$, $CONH_2$, $CONR^{22}R^{23}$, $SO_2$ alkyl, $SO_2NH_2$, or $SO_2NR^{22}R^{23}$, a 5- to 7-membered mono- or a 9- to 10-membered bicyclic heterocyclic or heteroaryl ring, which can be saturated or unsaturated, wherein the heterocyclic or heteroaryl ring contains from one to four heteroatoms selected from the group consisting of N, O and S, wherein the nitrogen and sulfur heteroatoms are optionally oxidized, and wherein the heterocyclic or heteroaryl ring is unsubstituted or substituted with one or more of $C_{1-4}$ alkyl, $C_{1-4}$ alkoxy, halogen, hydroxy, $CF_3$, $OCF_3$, $COOH$, $CO_2R^{21}$, $CONH_2$, $CONR^{22}R^{23}$, $SO_2$ alkyl, $SO_2NH_2$, or $SO_2NR^{22}R^{23}$, $C_{3-9}$ cycloalkyl, which is unsubstituted or substituted with one or more of $C_{1-4}$ alkyl, $C_{1-4}$ alkoxy, halogen, hydroxy, $CF_3$, $OCF_3$, $COOH$, $CO_2R^{21}$, $CONH_2$, $CONR^{22}R^{23}$, $SO_2$alkyl, $SO_2NH_2$, or $SO_2NR^{22}R^{23}$, or $C_{7-12}$ bicyclic alkyl, which is unsubstituted or substituted with one or more of $C_{1-4}$ alkyl, $C_{1-4}$ alkoxy, halogen, hydroxy, $CF_3$, $OCF_3$, $COOH$, $CO_2R^{21}$, $CONH_2$, $CONR^{22}R^{23}$, $SO_2$alkyl, $SO_2NH_2$, or $SO_2NR^{22}R^{23}$ Y is —NH— or O;

$R^3$ is hydrogen, halogen or OH;

$R^4$ and $R^5$ are independently hydrogen, halogen, alkyl, alkenyl, alkynyl, hydroxy, alkoxy, haloalkyl, haloalkoxy, hydroxyalkyl, cyano, nitro, —$CO_2R^x$, —$CH_2OR^x$ or —$OR^x$, where $R^x$, in each instance, is independently one of hydrogen or $C_{1-6}$ alkyl;

$R^6$ is cyano or acetylenyl;

$R^{11}$ is hydrogen, halogen or alkyl;

$R^{12}$ is
  hydrogen, halogen,
  $C_{1-6}$ alkyl, unsubstituted or substituted with one or more of hydroxy,
  COOH, amino, or halogen, or
  $CF_3$;

$R^{21}$ is $C_{1-8}$ alkyl, $C_{1-8}$ cycloalkyl, $C_{1-8}$ alkyl ether, or $C_{1-8}$ cycloalkyl ether;

$R^{22}$ and $R^{23}$ are, independently, hydrogen, $C_{1-8}$ alkyl, $C_{1-8}$ cycloalkyl, $C_{1-8}$ alkyl ether, or $C_{1-8}$ cycloalkyl ether or taken together with the nitrogen atom to which they are attached, $R_{22}$ and $R_{23}$ form a 3 to 9 member saturated ring, wherein 0 to 2 of the ring carbons are replaced by nitrogen or oxygen;

B is selected from the group consisting of:

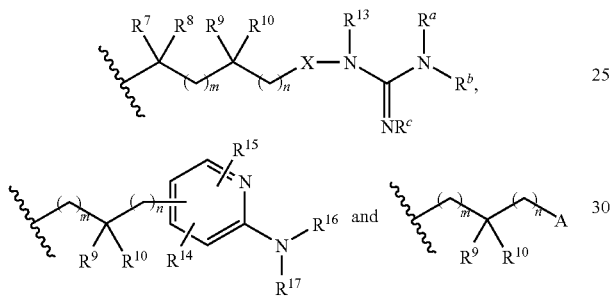

wherein
$R^7$, $R^8$, $R^9$, and $R^{10}$ are independently hydrogen or alkyl;

X is —O—, —$NR^{18}$—, or —CH=N— (where N is bonded to $NR^{13}$) where $R^{18}$ is hydrogen or alkyl, wherein said alkyl is optionally substituted with amino, monoalkylamino, dialkylamino, alkoxy, hydroxy, carboxy, alkoxycarbonyl, aryloxycarbonyl, aralkoxycarbonyl, acylamino, cyano or trifluoromethyl;

$R^a$, $R^b$ and $R^c$ are independently hydrogen, alkyl, hydroxy, alkoxy, alkoxycarbonyloxy, cyano or —$CO_2R^w$, where $R^w$ is $C_{1-12}$ alkyl, $C_{3-9}$ cycloalkyl, $C_{6-14}$ aryl, $C_{6-14}$ar$(C_{1-12})$ alkyl,

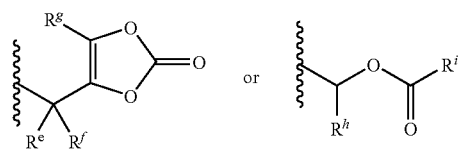

where $R^e$ and $R^f$ are independently hydrogen, $C_{1-6}$ alkyl, $C_{2-6}$ alkenyl or $C_{6-14}$ aryl, $R^g$ is hydrogen, $C_{1-6}$ alkyl, $C_{2-6}$ alkenyl or $C_{6-14}$ aryl, $R^h$ is hydrogen, $C_{1-6}$ alkyl, $C_{2-6}$ alkenyl or $C_{6-14}$ aryl, and $R^i$ is $C_{6-14}$ar$(C_{1-2})$alkyl or $C_{1-2}$ alkyl;

n is from zero to 2;

m is from zero to 2;

$R^{13}$ is hydrogen or alkyl;

$R^{14}$ and $R^{15}$ are independently hydrogen, alkyl, cycloalkyl, halogen or alkoxy;

$R^{16}$ and $R^{17}$ are independently hydrogen, alkyl, hydroxy, alkoxy, cyano or —$CO_2R^j$, where $R^j$ is $C_{1-12}$ alkyl, $C_{3-9}$ cycloalkyl, $C_{6-14}$ aryl, $C_{6-14}$ar$(C_{1-12})$alkyl, halo$(C_{1-12})$ alkyl or

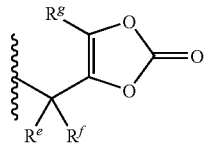

where $R^e$, $R^f$ and $R^g$ are independently hydrogen or $C_{1-12}$ alkyl; and A is a 9- to 10-membered bicyclic heterocyclic or heteroaryl ring which can be saturated or unsaturated,
wherein the heterocyclic or heteroaryl ring contains from three to five heteroatoms selected from the group consisting of N, O and S, and is optionally substituted with one or more of halogen, hydroxy, alkyl, alkoxy, or —$NR^{19}R^{20}$, where $R^{19}$ and $R^{20}$ are independently hydrogen or $C_{1-4}$ alkyl,
or wherein the heterocyclic or heteroaryl ring contains from one to two heteroatoms selected from N or O, and is monosubstituted with —$NR^{19}R^{20}$, where $R^{19}$ and $R^{20}$ are independently hydrogen or $C_{1-4}$ alkyl,
or wherein the heterocyclic or heteroaryl ring contains from one to two heteroatoms selected from the group consisting of N, O, S, one of which must be either O or S, and is optionally substituted with one or more of halogen, hydroxy, alkyl, alkoxy, or —$NR^{19}R^{20}$, where $R^{19}$ and $R^{20}$ are independently hydrogen or $C_{1-4}$ alkyl.

Compounds within the scope of the present invention include those for which $R^2$ is:
  phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, $CONH_2$, or $SO_2NH_2$,
  a 5- to 7-membered mono- or a 9- to 10-membered bicyclic heterocyclic or heteroaryl ring, which can be saturated or unsaturated, wherein the heterocyclic or heteroaryl ring contains from one to four heteroatoms selected from the group consisting of N, O and S, and is optionally substituted with halogen, hydroxy, or alkyl,
  $C_{3-9}$ cycloalkyl which can be saturated or unsaturated, or
  $C_{7-12}$ bicyclic alkyl which can be saturated or unsaturated,
  and the remaining substituents are as defined herein.

Compounds within the scope of the present invention include those for which:
  $R^4$ and $R^5$ are independently hydrogen, halogen, $C_{1-6}$ alkyl, $C_{2-6}$ alkenyl, $C_{2-8}$ alkynyl, hydroxy, halo$(C_{1-6})$alkyl, $C_{1-8}$ alkoxy, halo$(C_{1-8})$alkoxy or hydroxy$(C_{1-6})$alkyl, cyano, nitro, —$CO_2R^x$, —$CH_2OR^x$ or —$OR^x$,
  where $R^x$, in each instance, is independently one of hydrogen or $C_{1-6}$ alkyl;
  $R^{11}$ is hydrogen or $C_{1-6}$ alkyl;
  $R^7$, $R^8$, $R^9$ and $R^{10}$ are independently hydrogen or $C_{1-6}$ alkyl;
  $R^{18}$ is $C_{1-6}$ alkyl, which is optionally substituted with amino, mono$(C_{1-6})$ alkylamino, di$(C_{1-6})$alkylamino, $C_{1-8}$ alkoxy, hydroxy, carboxy, $C_{1-8}$ alkoxycarbonyl, $C_{6-10}$ aryloxycarbonyl, $C_{6-10}$ar$(C_{1-8})$alkoxycarbonyl, acylamino, cyano or trifluoromethyl;
  $R^a$, $R^b$ and $R^c$ are independently $C_{1-6}$ alkyl, $C_{1-8}$ alkoxy, or $C_{1-8}$ alkoxycarbonyloxy;
  $R^{13}$ is $C_{1-6}$ alkyl;

$R^{14}$ and $R^{15}$ are independently $C_{1-6}$ alkyl, $C_{3-9}$ cycloalkyl or $C_{1-8}$ alkoxy; and $R^{16}$ and $R^{17}$ are independently hydrogen, $C_{1-6}$ alkyl, $C_{1-8}$ alkoxy, or $C_{1-8}$ alkoxycarbonyl.

A preferred subgenus of compounds of Formula I above are those for which B is where X is O, and $R^7$-$R^{10}$, $R^{13}$, $R^a$-$R^c$, m and n are as defined above.

Another preferred subgenus of compounds of Formula I above are those for which B is where $R^9$, $R^{10}$ $R^{14}$-$R^{17}$, m and n are as defined above.

Yet another preferred subgenus of compounds of Formula I above are those for which B is where A, $R^9$, $R^{10}$, m and n are as defined above. Especially preferred compounds of this subgenus of those in which A is 3-aminobenzisoxazolyl.

Preferred compounds of Formula I above are those for which $R^1$ is $R^2CF_2C(R^{12})_2(CH_2)_q$. Especially preferred are those compounds in which $R^1$ is $R^2CF_2C(R^{12})_2(CH_2)_q$, in which $R^2$ is aryl, pyridyl, pyridyl-N-oxide or quinolinyl, any of which is optionally substituted with halogen or $C_{1-6}$ alkyl; $R^{12}$ is hydrogen; and q is zero. Preferred compounds are also those compounds in which $R^1$ is $R^2CF_2C(R^{12})_2(CH_2)_q$, in which $R^2$ is aryl, pyridyl, pyridyl-N-oxide, quinolinyl, or quinolinyl-N-oxide any of which is optionally substituted with halogen, $C_{1-6}$ alkyl or $SO_2$ alkyl; $R^{12}$ is hydrogen; and q is zero.

Preferred compounds of Formula I above are those for which $R^3$ is halogen or hydrogen. Even more preferred compounds of Formula I above are those for which $R^3$ is halogen. More preferred compounds within this subgenus are those for which $R^3$ is fluoro, including compounds for which $R^3$ is fluoro while $R^4$ and $R^5$ are hydrogen.

Preferred compounds of Formula I above are those for which $R^6$ is cyano. In another aspect, $R^6$ is acetylene.

Preferred also are those compounds of Formula I above for which $R^{11}$ is hydrogen or alkyl. Even more preferred compounds of Formula I above are those for which $R^{11}$ is hydrogen.

Preferred also are those compounds of Formula I above for which $R^3$ is halogen or hydrogen and $R^{11}$ is hydrogen or alkyl.

Preferred also are those compounds of Formula I above for which $R^6$ is cyano and $R^3$ is halogen. Even more preferred compounds of Formula I above are those for which $R^6$ is cyano and $R^3$ is fluoro. Even more preferred compounds of Formula I above are those for which $R^6$ is cyano and $R^3$ is fluoro while $R^4$ is hydrogen or fluoro and $R^5$ is hydrogen.

Preferred values of $R^a$, $R^b$ and $R^c$ in Formula I are independently hydrogen, hydroxy, $C_{1-6}$ alkyl, $C_{1-6}$ alkoxy, cyano or —$CO_2R^w$, where $R^w$, in each instance, is preferably one of $C_{1-4}$alkyl, $C_{4-7}$cycloalkyl or benzyloxycarbonyl. Suitable values of $R^a$, $R^b$ and $R^c$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, $R^a$, $R^b$ and $R^c$ are each hydrogen.

Also preferred at $R^a$, $R^b$ and $R^c$ is the group —$CO_2R^w$, where $R^w$ is one of where $R^e$-$R^i$ are defined as above. When $R^a$, $R^b$ and $R^c$ are —$CO_2R^w$, where $R^w$ is one of one of these moieties, the resulting compounds are prodrugs that possess desirable formulation and bioavailability characteristics. A preferred value for each of $R^e$, $R^f$ and $R^h$ is hydrogen, $R^g$ is methyl, and preferred values for $R^i$ include benzyl and tert-butyl.

Preferred compounds are those of Formula I, where $R^7$, $R^8$, $R^9$ and $R^{10}$ are independently one of hydrogen or $C_{1-6}$ alkyl. Useful values of $R^7$, $R^8$, $R^9$ and $R^{10}$ include hydrogen, methyl, ethyl, propyl, and n-butyl.

Preferred compounds when X is $NR^{18}$ are those wherein $R^{18}$ is hydrogen or $C_{1-6}$ alkyl, optionally substituted by one, two or three, preferably one, of amino, monoalkylamino, dialkylamino, alkoxy, hydroxy, alkoxycarbonyl, aryloxycarbonyl, aralkoxycarbonyl, carboalkoxy, phenyl, cyano, trifluoromethyl, acetylamino, pyridyl, thiophenyl, furyl, pyrrolyl or imidazolyl.

Suitable values of $R^{18}$ include hydrogen, methyl, ethyl, propyl, n-butyl, 2-hydroxyethyl, 3-hydroxypropyl, and 4-hydroxybutyl.

Most preferred are compounds of Formula I in which X is oxygen.

Preferred values of n in Formula I include from zero to 2, and most preferably zero or 1. Preferred values of m include from zero to 2, more preferably zero or 1.

Exemplary structures of compounds within the scope of the invention include the following:

-continued

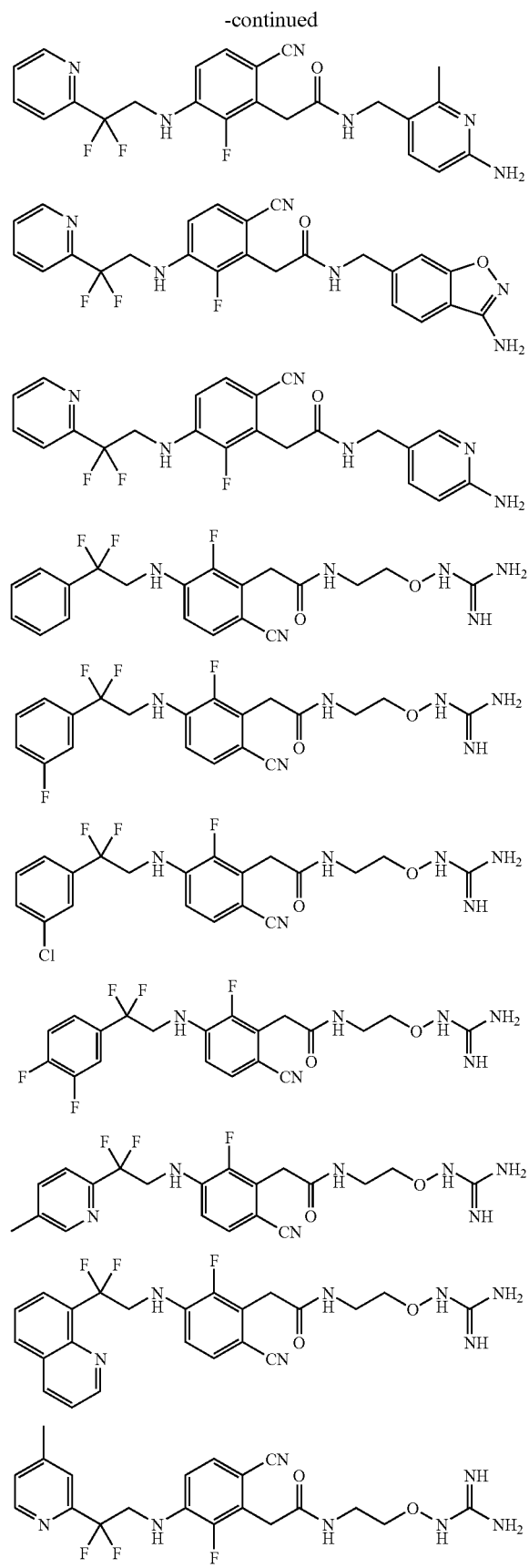

-continued

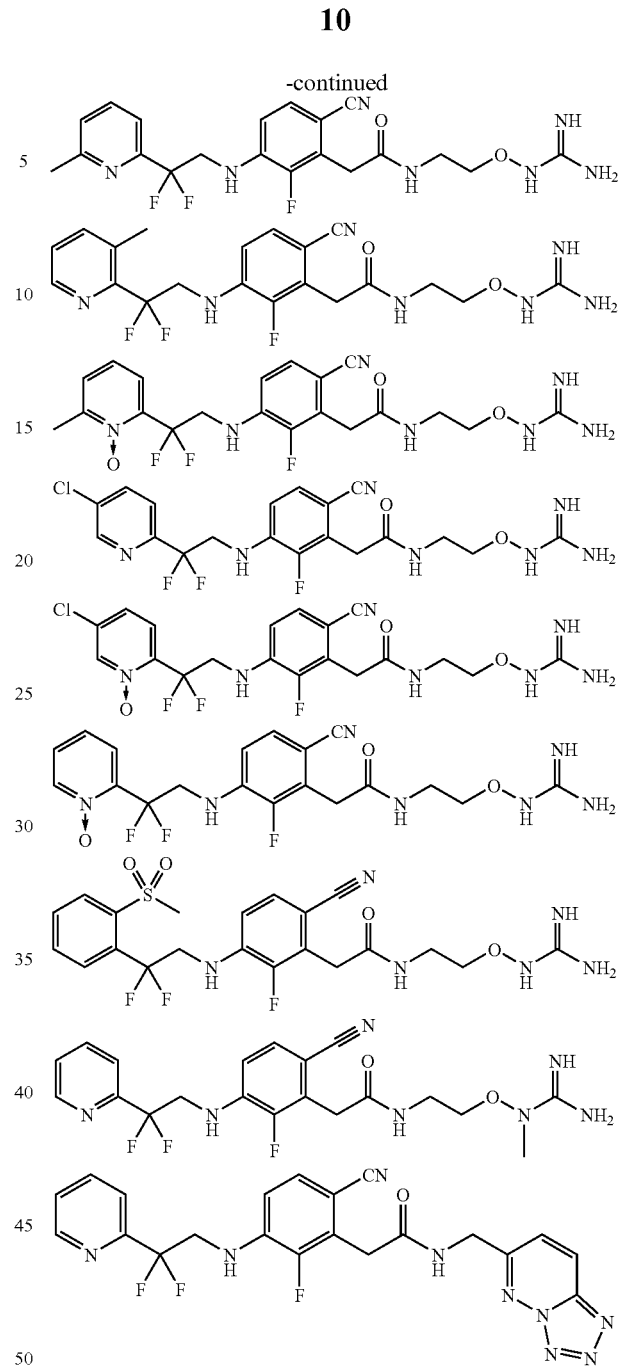

as well as pharmaceutically acceptable salts thereof, for example the hydrochloride and acetate salts thereof.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series. The compounds of the present invention can also have polymorphic crystalline forms, with all polymorphic crystalline forms being included in the present invention.

The compounds of Formula I can also be solvated, especially hydrated. Hydration can occur during manufacturing of the compounds or compositions comprising the compounds, or the hydration can occur over time due to the hygroscopic nature of the compounds.

Certain compounds within the scope of Formula I are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process. Useful prodrugs are those where $R^a$, $R^b$, $R^c$ and/or $R^d$ are —$CO_2R^w$, where $R^w$ is defined above. See, U.S. Pat. No. 5,466,811 and Saulnier et al., *Bioorg. Med. Chem. Lett.* 4:1985-1990 (1994).

When any variable occurs more than one time in any constituent or in Formula I, its definition on each occurrence is independent of its definition at every other occurrence. Also, combinations of substituents and/or variables are permissible only if such combinations result in stable compounds.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention provides diagnostic compositions which are used for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

According to a preferred aspect, useful compounds are those wherein the $R^1$ substituent is substituted with a detectable label, such as a radioactive iodine atom, such as I-125, I-131 or I-123. In this aspect, $R^1$ is preferably phenyl, having a para I-123, para I-125 or para I-131 substitution, or benzyl, having a meta I-123, meta I-125 or meta I-131 substitution.

The detectable label can also be a radioactive or paramagnetic chelate in which a suitable ligand (L) is attached to an $R^1$ substituent, either directly or via a divalent linking group A". Alternatively, the group -A"-L substitutes for the group W in Formula I. By suitable ligand is meant an organic moiety that is capable of chelating a radioactive or paramagnetic metal ion.

In these compounds, the divalent linking group A" includes groups that are capable of covalently bonding with a free amino group and the chelating means. For example, A" can be —C(=S)—, —C(=O)—, —C(=NH)—$(CH_2)_6$—C(=NH)—, —C(=O)—$(CH_2)_6$—C(=O)—,

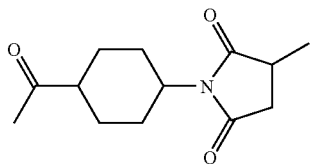

and the like.

Also, in the compounds represented by Formula I, the chelating ligand, L, includes groups capable of covalently bonding to or noncovalently binding to either a radioactive or paramagnetic atom. The chelating means including those which are customarily used for complexing radioactive or paramagnetic atoms. These include chelating means containing 3 to 12, preferably 3 to 8, methylene phosphonic acid groups, methylene carbohydroxamic acid groups, carboxyethylidene groups, or especially carboxymethylene groups, which are bonded to a nitrogen atom. If only one or two of the acid groups are bonded to a nitrogen atom, then that nitrogen is bonded to another nitrogen atom having such groups by an optionally substituted ethylene group or by up to four separated ethylene units separated by a nitrogen or oxygen or sulfur atom. Preferred as a completing means is diethylenetrimine-N,N,N',N",N"-pentaacetic acid (DTPA). DTPA is well known in the art as a chelating means for the radioactive atoms indium-111 (In-111), technetium-99m (Tc-99m), and the paramagnetic atom gadolinium (Gd). Khaw, et al., *Science* 209:295 (1980); Paik C. H. et al., U.S. Pat. No. 4,652,440 (1987); Gries, H. et al., U.S. Pat. No. 4,957,939 (1990). A preferred chelating ligand, L, is 1-(p-aminobenzyl)-diethylenetriaminepentaacetic acid. Also included as chelating means are compounds which contain sulfhydryl or amine moieties, the total of which in any combination is at least four. These sulfhydryl or amine moieties are separated from each other by at least two atoms which can be either carbon, nitrogen, oxygen, or sulfur. Especially preferred for chelating means, L, is metallothionein which is well known in the art as a chelating means for Tc-99m.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl. Preferably, alkyl is 1 to 6 carbon atoms.

The term "alkenyl" is used herein to mean a straight or branched chain radical of 2-20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2-20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage, is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 14 carbons in the ring portion, preferably 6-10 carbons in the ring portion, such as phenyl, naphthyl or tetrahydronaphthyl.

The term "heteroaryl" as employed herein refers to groups having 5 to 14 ring atoms; 6, 10 or 14" electrons shared in a cyclic array; and containing carbon atoms and 1, 2, 3 or 4 (preferably 1, 2, or 3) oxygen, nitrogen or sulfur heteroatoms (where examples of heteroaryl groups include, but are not limited to, thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group, refers to $C_{1-12}$ alkyl, preferably $C_{1-6}$ alkyl, groups as discussed above having an aryl substituent, such as benzyl, phenylethyl or 2-naphthylmethyl.

The term "cycloalkyl" as employed herein by itself or as part of another group, refers to cycloalkyl groups containing 3 to 9 carbon atoms, preferably 3 to 7 carbon atoms. Typical examples are cyclopropyl, cyclobutyl, cyclopentyl, cyclohexyl, cycloheptyl, cyclooctyl and cyclononyl.

The term "$C_{7-12}$ bicyclic alkyl" is intended to include bicyclo[2.2.1]heptyl (norbornyl), bicyclo[2.2.2]octyl, 1,1,3-trimethylbicyclo[2.2.1]heptyl(bornyl), and the like.

The term "halogen" or "halo" as employed herein by itself or as part of another group refers to chlorine, bromine, fluorine or iodine with chlorine and fluorine being preferred.

The term "monoalkylamine" as employed herein by itself or as part of another group refers to an amino group which is substituted with one alkyl group having from 1 to 12, preferably 1 to 6, carbon atoms.

The term "dialkylamine" as employed herein by itself or as part of another group refers to an amino group which is substituted with two alkyl groups, each having from 1 to 12, preferably 1 to 6, carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocycle" or "heterocyclic ring", as used herein except where noted, represents a stable 5- to 7-membered mono- or bicyclic or stable 7- to 10-membered bicyclic heterocyclic ring system, any ring of which can be saturated or unsaturated, and which consists of carbon atoms and from one to four heteroatoms, preferably one to three heteratoms, selected from the group consisting of N, O and S, and wherein the nitrogen and sulfur heteroatoms can optionally be oxidized, and the nitrogen heteroatom can optionally be quaternized, and including any bicyclic group in which any of the above-defined heterocyclic rings is fused to a benzene ring. Especially useful are rings containing one oxygen or sulfur, one to four nitrogen atoms, preferably one to three nitrogen atoms, or one oxygen or sulfur combined with one or two nitrogen atoms. The heterocyclic ring can be attached at any heteroatom or carbon atom which results in the creation of a stable structure. Examples of such heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, benzisoxazolyl, benzotetrazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it can form an $NR^aR^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

Schemes 1-5 outline a synthetic route to representative compounds of Formula I.

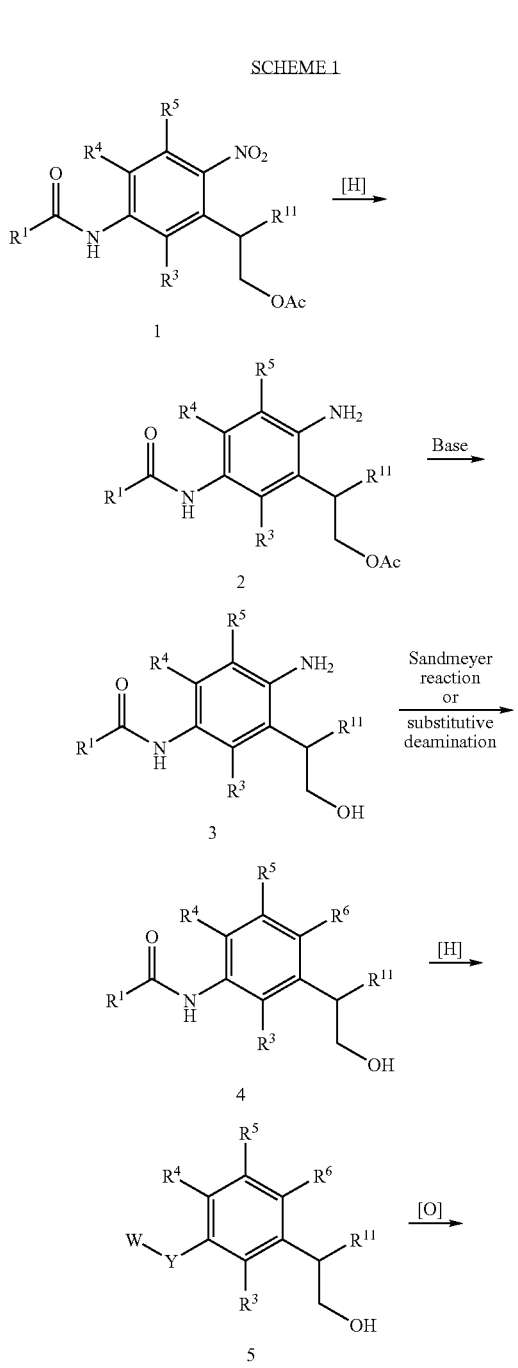

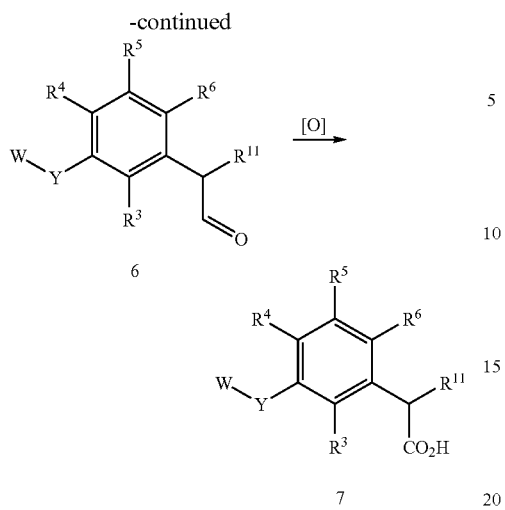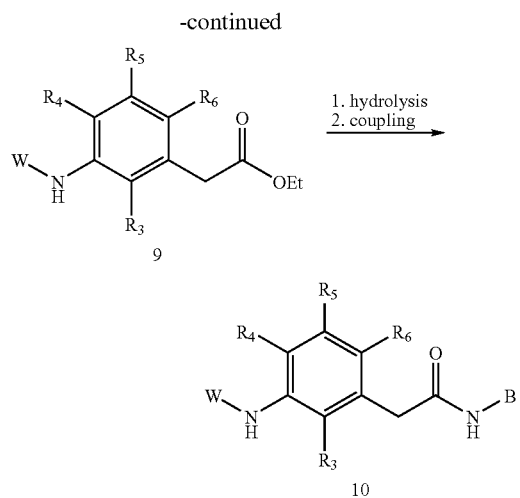

In Scheme 1, reduction of arylnitro compound 1 under typical conditions, such as catalytic hydrogenation with hydrogen in the presence of palladium on activated carbon in ethanol or methanol, gives arylamine 2. The acetyl protecting group of compound 2 is removed (in order to increase the solubility of the compound prior to the amino group manipulation) by hydrolysis under basic conditions, such as aqueous potassium carbonate ($K_2CO_3$) solution in methanol, to free the protected hydroxyl group, giving compound 3. The desired $R^6$ group is introduced into the center scaffold in place of the $NH_2$ group in compound 3 by a Sandmeyer-type reaction ((a) Gunstone, F. D., et al., *Org. Syn.* Collect Vol. 1, Wiley, New York, N.Y. (1941), p. 170; (b) Yokomoto, M, W., et al., EP published application No. 0 470 578 A1 (1991)) with suitable reagents, such as sodium nitrite ($NaNO_2$) and HCl followed by copper cyanide (CuCN) and potassium cyanide (KCN) to give compound 4. In the case of $R^6$=acetylene, the aniline 3 is converted to the corresponding bromide under typical Sandmeyer conditions, such as sodium nitrite ($NaNO_2$) and HCl followed by copper bromide (CuBr). The bromide is converted to the acetylene under standard conditions, such as $PdCl(pph_3)_2$ and tributylethylenyltin in a soluble solvent, such as DMF. Compound 4 in turn, is reduced with a suitable reducing agent, such as $BH_3$, to generate desired fragment WY of compound 5 where Y is —NH—. Oxidation of 5 with an oxidizing agent, such as sulfur trioxide pyridine complex ($SO_3$ pyridine) in DCM, yields aldehyde 6. Construction of the center and left fragment of the target compound is finally achieved by further oxidation of the aldehyde 6 to carboxylic acid 7 under suitable oxidation conditions, such as sodium chlorite ($NaClO_2$) in the presence of sodium dihydrogenphosphate ($NaH_2PO_4$) and DMSO (Dalcanale, E., et al., *J. Org. Chem.* 51:567 (1986)).

SCHEME 2

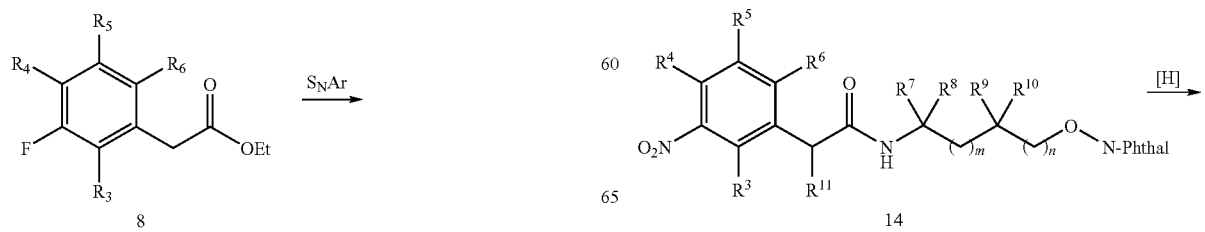

In Scheme 2, the amine is introduced by nucleophilic aromatic substitution, under typical conditions, such as DMSO at 100° C., giving compound 9. The ester group in 9 is hydrolyzed under standard conditions, such as LiOH, in a suitable solvent, such as MeOH:THF:$H_2O$, giving the corresponding carboxylic acid. The acid is coupled to an amine using standard coupling procedures, such as BOP, DIEA, using a suitable solvent, such as DMF, giving compounds with the structure 10.

SCHEME 3

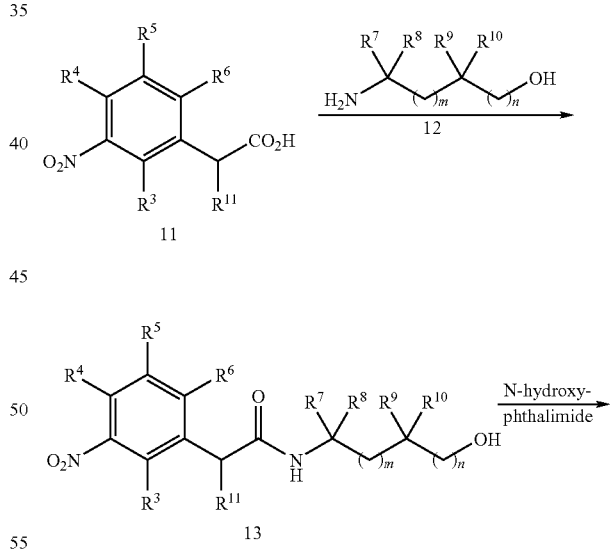

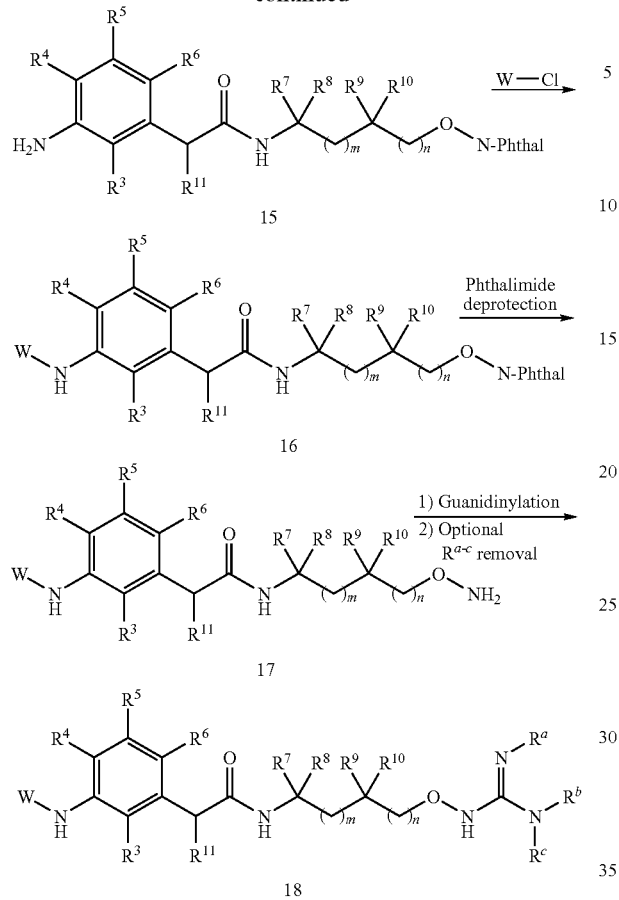

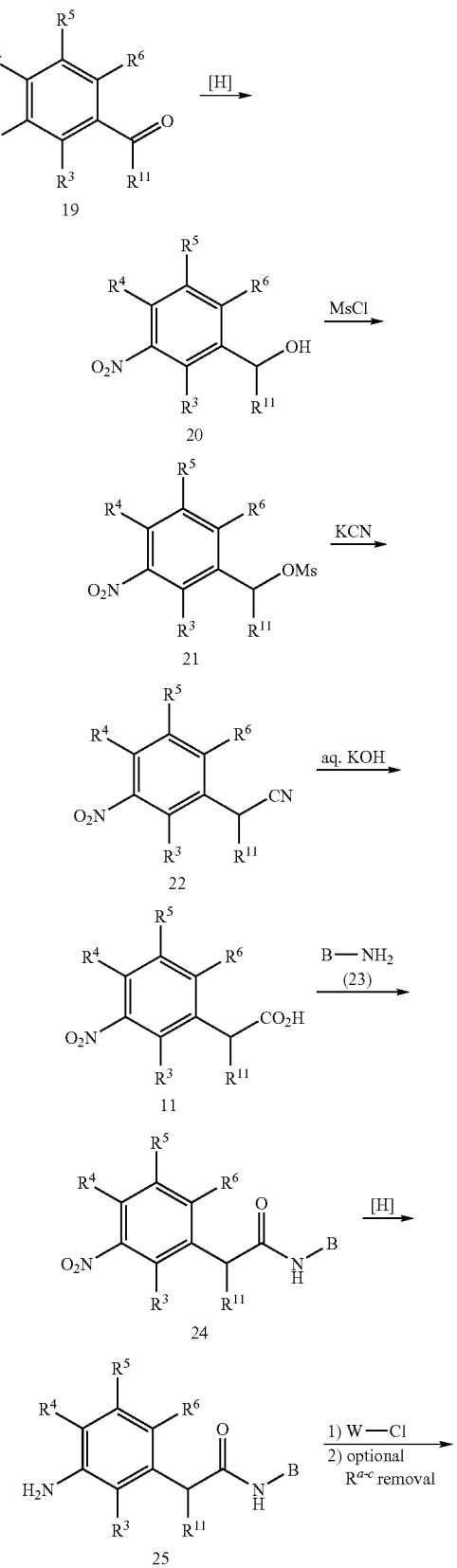

SCHEME 4

In Scheme 3, nitrophenylacetic acid 11 is coupled to an aminoalcohol 12, such as ethanolamine, using a standard peptide coupling procedure, such as in Scheme 2, to give alcohol 13. The alcohol is converted to the protected alkoxyamine by coupling to N-hydroxyphthalimide using standard reagents (Mitsunobu, O., *Synthesis* 1:1 (1981)), such as triphenylphosphine and diethylazodicarboxylate, in a suitable solvent, such as THF, to afford compound 14, which is then converted to aniline 15 under typical reducing conditions, such as hydrogenation over palladium(0) on carbon, in a suitable solvent, such as ethanol. The amine is reacted with an acylating agent (W=R$^1$C(O)) or a sulfonylating agent (W=R$^1$S(O$_2$)), such as benzylsulfonyl chloride, in a solvent, such as DCM, in Scheme 1 to give intermediate 16, and the alkoxyamine deprotected using standard conditions well known in the art (Greene, T. W. and Wuts, P. G. M., *Protective Groups in Organic Synthesis*, 2$^{nd}$ edition, John Wiley and Sons, New York (1991)), such as aqueous methylamine in ethanol/THF. Guanidinylation of the resulting alkoxyamine 17 is accomplished with a standard guanidinylation reagent, such as N,N'-bis(tert-butoxycarbonyl)-S-methylthiourea (Bergeron, R. J. and McManis, J. S., *J. Org. Chem.* 52:1700 (1987)) or N—R$^a$—N'—R$^b$, R$^c$-1H-pyrazole-1-carboxamidine (Bernatowicz, M. S. et al. *Tetrahedron Lett.* 34:3389 (1993)), and the guanidine optionally deprotected under typical deprotection conditions, such as trifluoroacetic acid (TFA) solution in DCM or HCl solution in 1,4-dioxane, to provide final target 18.

-continued

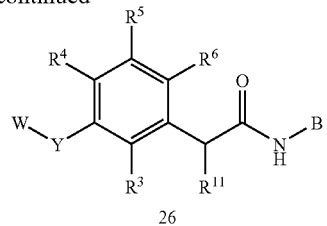

In Scheme 4, the ketone, aldehyde ($R^{11}$=H), or carboxylic acid ($R^{11}$=OH) starting material 19 is reduced with a suitable reagent, such as borane-THF, to give alcohol 20, which is then converted to a better leaving group by reaction with a sulfonyl chloride, such as methanesulfonyl chloride, in a suitable solvent, such as DCM, to produce compound 21. The sulfonate is displaced by cyanide under standard conditions, such as potassium cyanide in refluxing acetonitrile, to give nitrile 22, which is then hydrolyzed with a typical reagent, such as aqueous hydroxide. Coupling of the resulting acid 11 with amine 23 is accomplished as in Scheme 2 to give intermediate 24, and the nitro group is reduced as in Scheme 3 to afford aniline 25. This is acylated or sulfonylated as in Scheme 3 and the guanidine optionally deprotected as in Scheme 3 to give the final target 26 (Y=NH).

SCHEME 5

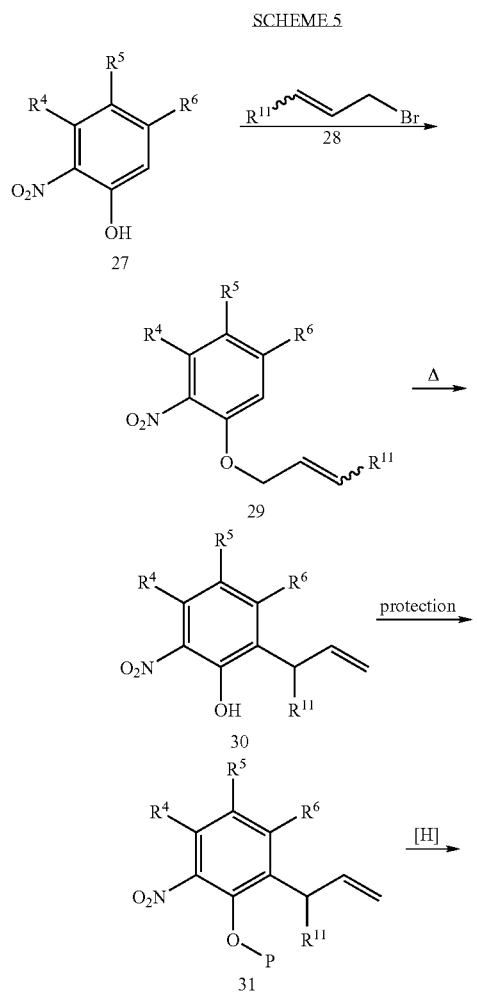

-continued

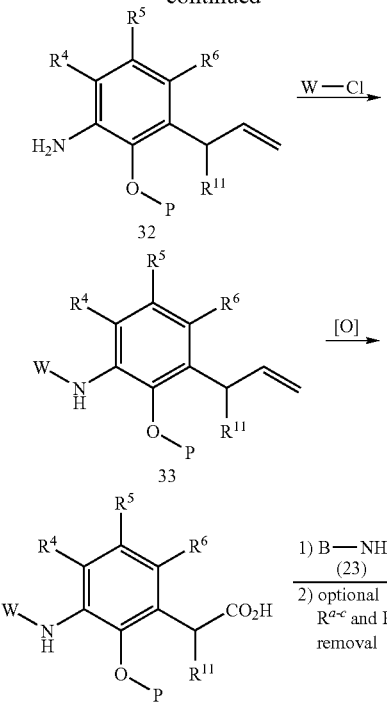

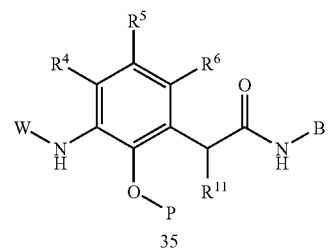

In Scheme 5, nitrophenol 27 is alkylated with allylic halide 28 and a suitable base, such a cesium carbonate, in a polar aprotic solvent, such as DMF, giving intermediate 29, which is then converted to compound 30 via the aromatic Claisen rearrangement by heating. The phenol is protected using typical reagents, such as benzyl bromide and cesium carbonate, in a solvent, such as DMF, to give 31 (where P is a typical hydroxyl protecting group) and the nitro group is reduced as in Scheme 3 to produce aniline 32. Aniline 32 is converted to intermediate 33 as in Scheme 4 and the alkene is oxidatively cleaved using standard conditions, such as sodium periodate and osmium tetraoxide in dioxane/water followed by Jones reagent, to provide acid 34. This is then coupled to amine 23, the guanidine optionally deprotected as in Scheme 3, and the phenol group optionally deprotected using standard conditions, such as hydrogenation over palladium (0) on carbon, in a suitable solvent, such as ethanol, to produce the target compound 35.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include, but are not limited to, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, trifluoroacetate, and undecanoate. Base salts include, but are not limited to, ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth, including salts with a guanidinyl moiety. Also, the basic nitrogen-containing groups can be quaternized with such agents as lower alkyl halides, such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Preferred acids for forming acid addition salts include HCl, acetic acid and methanesulfonic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

For their end-use application, the potency and other biochemical parameters of the enzyme-inhibiting characteristics of the compounds of the present invention are readily ascertained by standard biochemical techniques known to those of skill in the art. For example, an end use application of the compounds that inhibit chymotrypsin and trypsin is in the treatment of pancreatitis. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit thrombin can be employed for a number of therapeutic purposes. As thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA). Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, and blood lines. The compounds of the present invention can also be used as an anticoagulant in extracorporeal blood circuits.

Stents have been shown to reduce restenosis, but are thrombogenic. A strategy for reducing the thrombogenicity of stents is to coat, embed, adsord or covalently attach a thrombin-inhibiting agent to the stent surface. The compounds of the present invention can be employed for this purpose. Compounds of the invention can be attached to, or embedded within soluble and/or biodegradeable polymers as and thereafter coated onto stent materials. Such polymers can include polyvinylpyrrolidone, polyhydroxy-propylmethacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent No. 2,164,684 and PCT Published Applications Nos. WO 96/11668, WO 96/32143 and WO 96/38136.

By virtue of the effects of thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement.

The compounds of the present invention may be useful in treating neoplasia and metastasis as well as neurodegenerative diseases, such as Alzheimer's disease and Parkinson's disease.

When employed as thrombin inhibitors, the compounds of the present invention can be administered in an effective amount within the dosage range of about 0.1 to about 500 mg/kg, preferably between 0.1 to 10 mg/kg body weight, on a regimen in single or 2-4 divided daily doses.

When employed as inhibitors of thrombin, the compounds of the present invention can be used in combination with thrombolytic agents such as tissue plasminogen activator, streptokinase, and urokinase. Additionally, the compounds of the present invention can be used in combination with other antithrombotic or anticoagulant drugs such as, but not limited to, fibrinogen antagonists and thromboxane receptor antagonists.

The thrombin inhibitors can also be coupled with soluble polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the thrombin inhibitors can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Human leucocyte elastase is released by polymorphonuclear leukocytes at sites of inflammation and thus is a contributing cause for a number of disease states. Compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formula I are readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15: 836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each enzyme, namely N-Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25° C.

Useful dose ranges for the application of compounds of the present invention as neutrophil elastase inhibitors and as Cathepsin G inhibitors depend upon the nature and severity of the disease state, as determined by the attending diagnostician, with a range of from about 0.01 to 10 mg/kg body weight, per day, being useful for the aforementioned disease states.

Compounds of the present invention that inhibit urokinase or plasminogen activator are potentially useful in treating excessive cell growth disease state. As such compounds of the present invention may also be useful in the treatment of benign prostatic hypertrophy and prostatic carcinoma, the treatment of psoriasis, and as abortifacients. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

For compositions of the present invention suitable for administration to a human, the term "excipient" is meant to include, but not be limited by, those excipients described in the *Handbook of Pharmaceutical Excipients*, American Pharmaceutical Association, $2^{nd}$ Ed. (1994), which is herein incorporated by reference in its entirety. Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxy-propylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which can optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that can be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers can be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension can also contain stabilizers.

Compounds of Formula I can be labeled with radioactive iodine by using an exchange reaction. Exchange of hot iodine for cold iodine is well known in the art. Alternatively, a radio iodine labeled compound can be prepared from the corresponding bromo compound via a tributylstannyl intermediate. See, U.S. Pat. No. 5,122,361, herein incorporated by reference.

The present invention also includes compositions which are useful for in vivo imaging of thrombi in a mammal, wherein the compositions are comprised of a compound of Formula I complexed with a radioactive atom.

For the compounds of Formula I, suitable radioactive atoms include Co-57, Cu-67, Ga-67, Ga-68, Ru-97, Tc-99m, In-111, In-113m, Hg-197, Au-198, and Pb-203. Some radioactive atoms have superior properties for use in radiochemical imaging techniques. In particular, technetium-99m (Tc-99m) is an ideal radioactive atom for imaging because of its nuclear properties. Rhenium-186 and -188 also have gamma emission which allows it to be imaged. Preferred compositions contain the radioactive atom, Tc-99m.

The compounds of Formula I can be labeled by any of the many techniques known in the art to provide a composition of the present invention. For example, these compounds can be labeled through a chelating agent such as diethylene-triaminepentaacetic acid (DTPA) or metallothionein, both of which can be covalently attached to the compound of Formula I.

In general, the compositions of the present invention containing technetium-99m are prepared by forming an aqueous mixture of technetium-99m and a reducing agent and a water-soluble ligand, and then contacting the mixture with a compound of the present invention represented by Formula I. For example, the imaging compounds of this invention are made by reacting technetium-99m (in an oxidized state) with the compounds of the present invention having a chelating means in the presence of a reducing agent to form a stable complex between technetium-99m in a reduced state (IV or V valence state).

One embodiment of the composition of the present invention is prepared by labeling a compound of Formula I having a DTPA chelating means with technetium-99m. This can be accomplished by combining a predetermined amount (as 5 μg to 0.5 mg) of compound of the present invention with an aqueous solution containing citrate buffer and stannous reducing agent, then adding freshly eluted sodium pertechnetate containing a predetermined level of radioactivity (as 15 mCi). After allowing an incubation of the mixture at room temperature, the reaction mixture is loaded into a shielded syringe through a sterile filter (0.2-0.22 micron), then is dispensed into 0.9% saline for injection, if desired.

Another embodiment of the compositions of the present invention is prepared by labeling a compound of Formula I having a metallothionein chelating means with technetium-99m. This can be accomplished by combining aqueous sodium pertechnetate-99m with aqueous stannous glucoheptonate to form a soluble complex of technetium-99m (in reduced state) with two glucoheptonate molecules, then combining this solution with a compound of the Formula I having a metallothionein attached thereto. After incubating the mixture for a period of time and under conditions which allow for an exchange of the technetium-99m from the glucoheptonate complex to the metallothionein of the compound of Formula I, the technetium-labeled composition of the present invention is formed.

Reducing agents for use in the method are physiologically acceptable for reducing technetium-99m from its oxidized state to the IV or V valence state or for reducing rhenium from its oxidized state. Reducing agents which can be used are stannous chloride, stannous fluoride, stannous glucoheptonate, stannous tartarate, and sodium dithionite. The preferred agents are stannous reducing agents, especially stannous chloride or stannous glucoheptonate. The amount of reducing agent is that amount necessary to reduce the technetium-99m to provide for the binding to the chelating means of a compound of Formula I in this radioisotope's reduced state. For example, stannous chloride ($SnCl_2$) is the reducing agent and can be used in range from 1-1,000 μg/mL.

Citric acid complexes with technetium-99m quickly to form a stable technetium-99m-citrate complex. Upon contact with a compound of Formula I, substantially quantitative transfer of technetium-99m from its citrate complex to the chelating means of the compound of Formula I is achieved rapidly and under mild conditions. The amount of citric acid (as sodium citrate) can range from about 0.5 mg/ml up to the amount maximally soluble in the medium. Preferred amounts of citric acid range from 15 to 30 μg/ml.

The amount of compound of Formula I having a chelating means can range from 0.001 to about 3 mg/mL, preferably about 0.017 to about 0.15 mg/mL. Finally, technetium-99m in the form of pertechnetate can be used in amounts of preferably about 1-50 mCi. The amount of mCi per mg of compound of the present invention is preferably about 30-150.

The reaction between the compound of Formula I and the metal ion-transfer ligand complex is preferably carried out in a aqueous solution at a pH at which the compound of Formula I is stable. By "stable", it is meant that the compound remains soluble and retains its inhibitory activity against α-thrombin. Normally, the pH for the reaction will be from about 5 to 9, the preferred pH being between 6-8. The technetium-99m-citrate complex and a compound of Formula I are incubated, preferably at a temperature from about 20° C. to about 60° C., most preferably from about 20° C. to about 37° C., for a sufficient amount of time to allow transfer of the metal ion from the citrate complex to the chelating means of the compound of Formula I. Generally, less than one hour is sufficient to complete the transfer reaction under these conditions.

Alternative compositions of the present invention include an In-111 labeled compound of the present invention.

The present invention also includes compositions of the compounds of the present invention which are useful for in vivo imaging of thrombi in a mammal, comprised of a compound represented by Formula I complexed to a paramagnetic atom.

Preferred paramagnetic atoms are divalent or trivalent ions of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium(III) and ytterbium (III). Because of their very strong magnetic moments, gadolinium(III), terbium(III), dysoprosium(III), holmium(III), and erbium(III) are preferred. Especially preferred for the paramagnetic atom is gadolinium(III).

The compositions of the present invention can be prepared, for example, by combining a compound of Formula I with a paramagnetic atom. For example, the metal oxide or a metal salt (for example, nitrate, chloride or sulfate) of a suitable paramagnetic atom is dissolved or suspended in a medium comprised of water and an alcohol, such as methyl, ethyl or isopropyl alcohol. This mixture is added to a solution of an equimolar amount of the compound of Formula I in a similar aqueous medium and stirred. The reaction mixture can be heated moderately until the reaction is completed. Insoluble compositions formed can be isolated by filtering, while soluble compositions can be isolated by evaporation of the solvent. If acid groups on the chelating means are still present in the composition of the present invention, inorganic or organic bases, and even amino acids, can be added to convert the acidic complex into a neutral complex to facilitate isolation or purification of homogenous composition. Organic bases or basic amino acids can be used as neutralizing agents, as well as inorganic bases such as hydroxides, carbonates or bicarbonates of sodium, potassium or lithium.

The present invention also include diagnostic compositions which are useful for in vivo imaging of thrombi in a mammal, comprising a pharmaceutically acceptable carrier and a diagnostically effective amount of compositions derived from the compounds of Formula I.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medial diagnostic arts. Also, the diagnostically effective amount and method of administration can be tailored to achieve optimal efficacy but will depend on such factors as weight, diet, concurrent medication and other factors which those skilled in the medical arts will recognize. In any regard, the dose for imaging should be sufficient for detecting the presence of the imaging agent at the site of a thrombus in question. Typically, radiologic imaging will require that the dose provided by the pharmaceutical composition position of the present invention be, for example, about 5 to 20 μCi, preferably about 10 μCi. Magnetic resonance imaging will require that the dose provided be, for example, about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

"Pharmaceutically acceptable carriers" for in vivo use are well known in the pharmaceutical art, and are described, for example, in *Remington's Pharmaceutical Sciences*, Mack Publishing Co. (A. R. Gennaro edit. 1985). The pharmaceutical compositions of the present invention can be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions can contain minor amounts of nontoxic auxiliary substances, such as wetting agents, pH buffering agents, and the like. If desired, absorption enhancing preparations (e.g., liposomes) can be utilized.

The present invention also encompasses diagnostic compositions prepared for storage or administration. These would additionally contain preservatives, stabilizers and dyes. For example, sodium benzoate, sorbic acid and esters of p-hydroxybenzoic acid can be added as preservatives. In addition, antioxidants and suspending agents can be used.

The in vivo imaging methods of the present invention also offer several advantages over previous imaging techniques for the detection or monitoring of the presence, size, regression or increase of a thrombus. In particular, the present invention provides compounds, compositions and diagnostic compositions that bind tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

The term "in vivo imaging" as used herein relates to methods of the detection of a thrombus in a mammal, as well as the monitoring of the size, location and number of thrombi in a mammal, as well as dissolution or growth of the thrombus.

In employing the compounds, compositions or diagnostic compositions in vivo by this method, "administering" is accomplished parenterally, in either a systemic or local targeted manner. Systemic administration is accomplished by injecting the compounds, compositions by diagnostic compositions of the present invention into a convenient and accessible vein or artery. This includes but is not limited to administration by the ankecubutal vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

Also, the manner of delivery of a composition of the present invention to the site of a thrombus is considered within the scope of the term "administering". For example, a compound represented by Formula I having a chelating means attached thereto can be injected into the mammal, followed at a later time by the radioactive atom thereby forming in vivo at the site of the thrombus the composition comprising the compound of formula complexed to radioactive atom. Alternatively, a composition comprising the compound of formula complexed to radioactive atom can be injected into the mammal.

The "diagnostically effective amount" of the compounds, compositions or diagnostic compositions used in the methods of the present invention will, as previously mentioned, depend on the route of administration, the type of mammal being treated, and the physical characteristics of the specific mammal under treatment. These factors and their relationship to determining this dose are well known to skilled practitioners in the medical diagnostic arts. In any regard, the dose for in vivo imaging should be sufficient for detecting the presence of the imaging agent at the site of a thrombus in question.

Typically, radiologic imaging will require that the dose provided by the diagnostic composition of the present invention be about 5 to 20 μCi, preferably about 10 μCi. Magnetic resonance imaging will require that the dose provided by the diagnostic composition be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

The detecting of a thrombus by imaging is made possible by the presence of radioactive or paramagnetic atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The paramagnetic atoms associated with the compositions and diagnostic compositions of the present invention are detected in magnetic resonance imaging (MRI) systems. In such systems, a strong magnetic field is used to align the nuclear spin vectors of the atoms in a patient's body. The field is disturbed by the presence of paramagnetic atoms localized at a thrombus and an image of the patient is read as the nuclei return to their equilibrium alignments.

The following examples are illustrative, but not limiting, of the method and compositions of the present invention. Other suitable modifications and adaptations of the variety of conditions and parameters normally encountered and obvious to those skilled in the art are within the spirit and scope of the invention.

Example 1

N-[2-(Amidinoaminooxy)ethyl]-2-{3-[(2,2-difluoro-2-(5-methylpyridyl)ethyl)amino]-6-cyano-2-fluorophenyl}acetamide

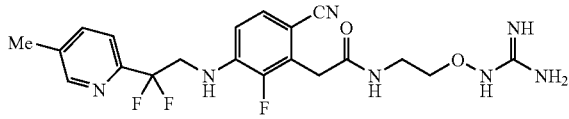

a.
N-[2-(Benzyloxycarbonylamino)ethoxy]phthalimide

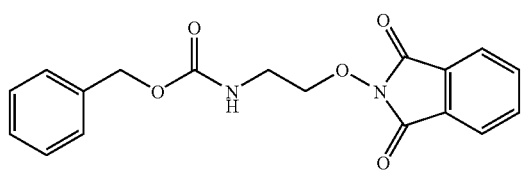

To a solution of benzyl N-(2-hydroxyethyl)carbamate (5.9 g, 30 mmol), N-hydroxyphthalimide (4.9 g, 30 mmol), and triphenylphosphine (7.9 g, 30 mmol) in tetrahydrofuran (100 mL) was added diethyl azodicarboxylate (5.2 g, 30 mmol). The reaction mixture was stirred at room temperature overnight. Ethyl acetate (200 mL) was added, washed with saturated NaHCO$_3$ (2×100 mL) and brine (100 mL), dried over Na$_2$SO$_4$, and filtered. After evaporating the filtrate, the residue was purified by flash column chromatography (methylene chloride to 4% ethyl acetate in methylene chloride) to give the title compound as a white solid (9.3 g, 91%). $^1$H-NMR (300 MHz, CDCl$_3$) δ 7.84 (m, 2H), 7.78 (m, 2H), 7.37 (m, 5H), 5.97 (br s, 1H), 5.14 (s, 2H), 4.27 (t, J=4.9 Hz, 2H), 3.51 (q, J=5.2 Hz, 2H).

b. 2-(Benzyloxycarbonylamino)ethoxyamine

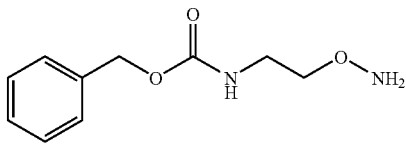

To a solution of N-[2-(benzyloxycarbonylamino)ethoxy]phthalimide (1.36 g, 4.0 mmol), as prepared in the preceding step, in ethanol (20 mL) and tetrahydrofuran (20 mL) was added 40% methylamine (2.0 mL, 25 mmol) and stirred at room temperature for 1 h. After evaporating the solvent, the residue was passed through silica gel (3:1 ethyl acetate:hexane to ethyl acetate) to give the title compound as a white solid (800 mg, 95%). $^1$H-NMR (300 MHz, CDCl$_3$) δ 7.36 (m, 5H), 5.47 (br s, 2H), 5.21 (br s, 1H), 5.10 (s, 2H), 3.72 (t, J=5.0 Hz, 2H), 3.44 (q, J=5.0 Hz, 2H).

c. [N,N'-Di(tert-butoxycarbonyl)]2-(benzyloxycarbonylamino)ethoxyguanidine

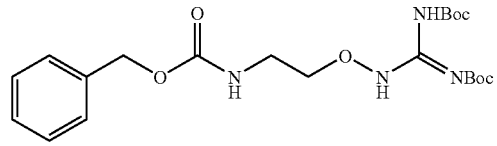

To a solution of 2-(benzyloxycarbonylamino)ethoxyamine (780 mg, 3.7 mmol), as prepared in the preceding step, in N,N-dimethylformamide (20 mL) was added [N,N'-di(tert-butoxycarbonyl)]amidinopyrazole (1.25 g, 4.0 mmol). The mixture was stirred at room temperature overnight, and the solvent evaporated under high vacuum. The residue was purified by flash column chromatography (0-5% ethyl acetate in methylene chloride) to give the title compound as a colorless oil (1.55 g, 93%). $^1$H-NMR (300 MHz, CDCl$_3$) δ 9.08 (s, 1H), 7.67 (s, 1H), 7.33 (m, 5H), 6.21 (br s, 1H), 5.21 (br s, 1H), 5.11 (s, 2H), 4.12 (t, J=4.8 Hz, 2H), 3.54 (q, J=4.9 Hz, 2H), 1.49 (s, 9H), 1.46 (s, 9H).

d. [N,N'-Di(tert-butoxycarbonyl)]2-aminoethoxyguanidine

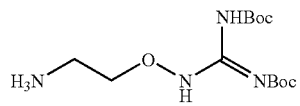

A mixture of [N,N'-di(tert-butoxycarbonyl)]2-(benzyloxycarbonylamino)ethoxyguanidine (730 mg, 1.5 mmol), as prepared in the preceding step, 10% palladium on carbon (70 mg) in ethanol (20 mL) and tetrahydrofuran (20 mL) was hydrogenated under hydrogen (balloon) for 30 min. The catalysts were removed by filtration through Celite and the filtrate was concentrated in vacuo. The residue was purified on a Waters Sep-Pak (10 g, 95:5 methylene chloride:methanol saturated with ammonia) to give the title compound as a colorless oil (290 mg, 61%). $^1$H-NMR (300 MHz, CDCl$_3$) δ 9.08 (br s, 1H), 4.08 (t, J=5.2 Hz, 2H), 2.99 (q, J=5.1 Hz, 2H), 1.50 (s, 9H), 1.48 (s, 9H).

In order to give the title compound as a white hygroscopic solid in the form of the hydrochloride salt, a 2-L Parr glass hydrogenation bottle was flushed with nitrogen and charged with chloroform (150 mL) and 10% palladium-on-carbon (30 g). [N,N'-Di(tert-butoxycarbonyl)]2-(benzyloxycarbonylamino)ethoxyguanidine (196.7 g, 0.37 moles), as prepared in the preceding step, was dissolved in methanol, diluting it to a volume of 640 mL. The methanol solution was added to the contents of the hydrogenation bottle. The mixture was shaken while maintaining 15-30 psi of hydrogen pressure. (Note: After one hour and again after another two hours, the vessel was vented and placed under vacuum for five minutes to remove the carbon dioxide by-product. The shaker bottle was then refilled with hydrogen to 30 psi.) After the second replacement of the carbon dioxide by-product mixture, the shaking was continued until the uptake of hydrogen ceased (approximately 20 hours, total reaction time). The reaction vessel was vented and the mixture was treated with celite (30 g). The suspension was filtered through a pad of celite (30 g). The filter cake was washed with anhydrous ethanol (3×150 mL). Clarion 470 clay (0.5 g) was added to the filtrate and the suspension was clarified by vacuum filtration. The solution was concentrated to dryness under reduced pressure (28 inches Hg, 50° C.) on a rotary evaporator. The residue was dried further for two hours under full vacuum (29 inches Hg, 50° C.).

The dried residue was treated with water (1.2 L) and the mixture was stirred for 30 minutes to effect a complete solution. Potassium carbonate (110 g) was added to the solution and the mixture was stirred for 20 minutes. Methylene chloride (450 mL) was added and the biphasic mixture was stirred for 40 minutes. The organic layer was separated, washed with water (4×1.2 L), and dried over potassium carbonate. The suspension was vacuum filtered and the filtrate was cautiously treated, in small portions, to pH 2-3 with 5-6M anhydrous hydrogen chloride in 2-propanol (62 mL). (Note: Caution must be observed during the acidification as a more acidic pH will cause loss of the BOC groups.) The filtrate was concentrated to dryness under reduced pressure (28 inches Hg, 40° C.) on a rotary evaporator. The solid residue was removed to a drying pan and oven dried in vacuo at 50° C. overnight (approximately 12 hours) to afford title compound as a white hygroscopic solid (111.9 g, 98.4% yield, 0.36 moles). $^1$H NMR (400 MHz, CDCl$_3$) δ 9.18 (s, 1H), 8.67 (br s, 3H), 7.58 (s, 1H), 4.34 (m, 2H), 3.42 (m, 2H), 1.51 (s, 9H), 1.46 (s, 9H).

e. Difluoro-(5-methyl-pyridin-2-yl)-acetic Acid Ethyl Ester

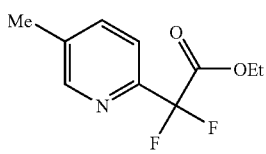

To a stirred suspension of Cu(0) (12.2 g, 0.19 mmol, 2.2×) in DMSO (87 mL) at RT under argon was added ethyl bromodifluoroacetate (13.4 mL, 0.10 mol, 1.2×) (see Eto, H., et al.; Chem. Pharm. Bull. 48: 982-990, 2000; and Ashwood, M. S., et al.; Tetrahedron Lett. 43: 9271-9273, 2002). After 2.5 h, 2-bromo-5-methylpyridine was added in one portion, the flask resealed, re-evacuated, and purged with argon. After 48 h, the reaction was partitioned between EtOAc (200 mL) and saturated NH$_4$Cl (150 mL). The organic phase was rewashed with saturated NH$_4$Cl (100 mL) until the blue color dissipated. The organic phase was dried over Na$_2$SO$_4$ and concentrated in vacuo to afford a yellow/green non-viscous oil. Purification via flash chromatography (30% EtOAc/hexanes) afforded the product as a clear oil (10.5 g, 0.05 mol, 56% yield). $^1$H NMR (300 Hz, CDCl$_3$) δ 8.47 (s, 1H), 7.63 (m, 2H), 4.37 (q, J=7.3 Hz), 2.40 (s, 3H), 1.33 (t, J=7.3 Hz, 3H); LC/MS (m/z) [M+1]$^+$ 216.2 (calculated for C$_{10}$H$_{12}$F$_2$NO$_2$, 216.2).

f. 2,2-Difluoro-2-(5-methyl-pyridin-2-yl)-ethanol

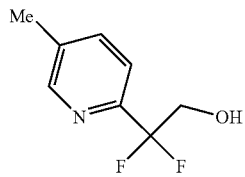

To a solution of difluoro-(5-methyl-pyridin-2-yl)-acetic acid ethyl ester (10.5 g, 0.05 mol), as prepared in the previous step, in EtOH (98 mL) cooled to 0° C. was added NaBH$_4$ (3.7 g, 0.098 mol, 2×). After 3 h the reaction was carefully quenched with saturated NH$_4$Cl (100 mL) and partitioned with EtOAc (200 mL). The organic phase was dried over Na$_2$SO$_4$ and concentrated in vacuo to afford the product as a white solid (8.5 g, 0.05 mol, 100% crude yield). $^1$H NMR (300 Hz, CDCl$_3$) δ 8.43 (s, 1H), 7.66 (m, 2H), 4.22 (t, J=12.3 Hz), 2.41 (s, 1H); LC/MS (m/z) [M+1]$^+$ 174.1 (calculated for C$_8$H$_{10}$F$_2$NO, 174.2).

g. 2-(1,1-Difluoro-2-iodo-ethyl)-5-methyl-pyridine

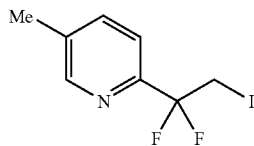

2,2-Difluoro-2-(5-methyl-pyridin-2-yl)-ethanol (8.5 g, 0.05 mol), as prepared in the previous step, was dissolved into toluene:CH3CN (98 mL, 2:1) and cooled to 0° C. To this solution was added PPh$_3$ (19.3 g, 0.074 mol, 1.5×), imidazole (6.7 g, 0.098 mol, 2×) and I$_2$ (18.7 g, 0.074 mol, 1.5×). The reaction was heated to 90° C., then was cooled to RT and concentrated in vacuo to afford a thick amber oil. Purification via flash chromatography (CH$_2$Cl$_2$) afforded the product as a clear oil (4.6 g, 0.016 mol, 33% yield). $^1$H NMR (300 Hz, CDCl$_3$) δ 8.48 (s, 1H), 7.61 (m, 1H), 3.92 (t, J=14.7 Hz), 2.41 (s, 3H); LC/MS (m/z) [M+1]$^+$ 284.1 (calculated for C$_8$H$_9$F$_2$IN, 284.07).

h. 2-(2-Azido-1,1-difluoro-ethyl)-5-methyl-pyridine

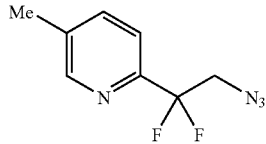

A solution of 2-(1,1-Difluoro-2-iodo-ethyl)-5-methyl-pyridine (3.8 g, 13.43 mmol), as prepared in the previous step, was dissolved into DMSO (6 mL), treated with NaN$_3$ (1.0 g, 16.12 mmol, 1.2×) and heated to 90° C. After 2 days, the reaction was partitioned between EtOAc (125 mL) and H$_2$O (2×50 mL). The organic phase was dried over Na$_2$SO$_4$ and concentrated to afford the product as a clear oil (2.46 g, 12.42 mmol, 93% crude yield). $^1$H NMR (300 Hz, CDCl$_3$) δ 8.49 (s, 1H), 7.63 (m, 2H), 4.01 (t, J=13.2 Hz), 2.41 (s, 3H); LC/MS (m/z) [M+1–N$_2$]$^+$ 171.1 (calculated for C$_8$H$_9$F$_2$N$_2$, 171.2).

i. 2,2-Difluoro-2-(5-methyl-pyridin-2-yl)-ethylamine

A solution of 2-(2-Azido-1,1-difluoro-ethyl)-5-methyl-pyridine (2.46 g, 12.42 mol), as prepared in the previous step, in EtOAc (150 mL) was treated with 2.46 g, 10 wt. % Pd—C under a H$_2$ atmosphere. After 24 h, the reaction was filtered through Celite and the filtrate concentrated to afford the product as a clear yellow oil (1.85 g, 10.76 mmol, 86% crude yield). $^1$H NMR (300 Hz, CDCl$_3$) δ 8.48 (s, 1H), 7.61 (m, 2H), 3.42 (t, J=14.2 Hz), 2.39 (s, 3H); LC/MS (m/z) [M+1]$^+$ 173.0 (calculated for C$_8$H$_{11}$F$_2$N$_2$, 173.2).

j. {6-Cyano-3-[2,2-difluoro-2-(5-methyl-pyridin-2-yl)-ethylamino]-2-fluoro-phenyl}-acetic Acid Ethyl Ester

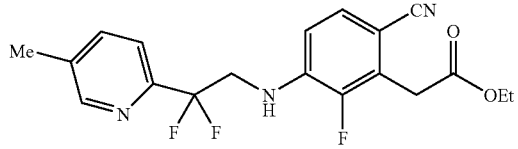

A mixture of 2,2-Difluoro-2-(5-methyl-pyridin-2-yl)-ethylamine (1.85 g, 10.76 mmol, 2×) and (6-Cyano-2,3-difluoro-phenyl)-acetic acid ethyl ester (1.2 g, 5.33 mmol), prepared as described in Example 2f, was dissolved into DMSO (3 mL) and heated to 90° C. under argon. After 20 h, the reaction was partitioned between EtOAc (50 mL) and H$_2$O (50 mL). The aqueous phase was re-extracted with EtOAc (30 mL) and the combined organic phase dried over Na$_2$SO$_4$ and concentrated to afford a yellow oil. Purification via flash chromatography (20% EtOAc/hexanes) afforded the product as a clear oil (968 mg, 2.57 mmol, 48% yield). $^1$H NMR (300 Hz, CDCl$_3$) δ 8.49 (s, 1H), 7.59 (m, 2H), 7.30 (m, 1H), 6.79 (t, J=8.2 Hz, 1H), 4.13 (m, 4H), 3.80 (d, J=2.0 Hz, 2H), 2.41 (s, 3H), 1.27 (t, J=6.9 Hz, 3H); LC/MS (m/z) [M+1]$^+$ 378.0 (calculated for C$_{19}$H$_{19}$F$_3$N$_3$O$_2$, 378.4).

k. N-[2-(N',N''-Bis(tert-butoxycarbonyl)amidinoaminooxy)ethyl]-2-{3-[(2,2-difluoro-2-(4-methylpyridyl)ethyl)amino]-6-cyano-2-fluorophenyl}acetamide

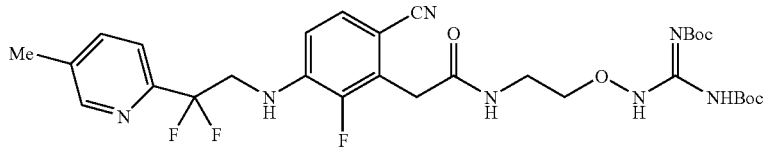

{6-Cyano-3-[2,2-difluoro-2-(5-methyl-pyridin-2-yl)-ethylamino]-2-fluoro-phenyl}-acetic acid ethyl ester (968 mg, 2.57 mmol), prepared as described in the previous step, was dissolved into MeOH:THF:H$_2$O (51 mL, 1:2:1) and treated with LiOH (92 mg, 3.85 mmol, 1.5×). After 1.5 h, the reaction was neutralized with 428 μL, 12N HCl and concentrated in vacuo. The crude material was diluted with toluene and concentrated (3×25 mL) to afford the saponification product {6-cyano-3-[2,2-difluoro-2-(5-methyl-pyridin-2-yl)-ethylamino]-2-fluoro-phenyl}-acetic acid. {6-cyano-3-[2,2-difluoro-2-(5-methyl-pyridin-2-yl)-ethylamino]-2-fluoro-phenyl}-acetic acid, HCl salt of [N,N'-di(tert-butoxycarbonyl)]-2-aminoethoxyguanidine (1.8 g, 5.13 mmol, 2×) (prepared as described in Example 1d), and BOP (1.8 g, 4.16 mmol, 1.6×) were dissolved into CH$_3$CN/CH$_2$Cl$_2$ (12 mL, 1:1) and cooled to 0° C. DIEA (2.7 mL, 15.6 mmol, 6×) was added dropwise and the reaction continued for 12 h, allowing the ice bath to warm to rt. The reaction was partitioned between EtOAc (50 mL) and H$_2$O (50 mL), the organic phase dried over Na$_2$SO$_4$, and concentrated to afford the crude product as a white amorphous solid. Purification via flash chromatography (20% EtOAc/CH$_2$Cl$_2$) afforded the product as a white solid (832 mg, 1.28 mmol, 50% yield). $^1$H NMR (300 Hz, CDCl$_3$) δ 9.14 (s, 1H), 8.49 (s, 1H), 7.61, m, 2H), 6.75 (t, J=8.2 Hz, 1H), 4.13 (m, 4H), 3.83 (s, 2H), 3.61 (m, 2H), 2.41 (s, 3H), 1.51 (s, 9H), 1.47 (s, 9H); LC/MS (m/z) [M+1]$^+$ 650.3 (calculated for C$_{30}$H$_{39}$F$_3$N$_7$O$_6$, 650.7).

l. N-[2-(Amidinoaminooxy)ethyl]-2-{3-[(2,2-difluoro-2-(5-methylpyridyl)ethyl)amino]-6-cyano-2-fluorophenyl}acetamide

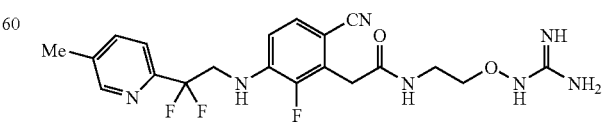

N-[2-(N',N''-Bis(tert-butoxycarbonyl)amidinoaminooxy)ethyl]-2-{3-[(2,2-difluoro-2-(5-methylpyridyl)ethyl)

amino]-6-cyano-2-fluorophenyl}acetamide (832 mg, 1.28 mmol), as prepared in the previous step, was dissolved into CH$_2$Cl$_2$ (6 mL), cooled to 0° C. and treated with TFA (2 mL), then allowed to warm to rt. After 12 h, the reaction was concentrated in vacuo to afford a yellow oil. Purification via flash chromatography (inactivated with NH$_3$, 10% MeOH/CH$_2$Cl$_2$) afforded the product as a white solid (413 mg, 0.92 mmol, 72% yield). 1H NMR (300 Hz, CD$_3$OD) δ 8.49 (s, 1H), 7.73 (d, J=7.9 Hz, 1H), 7.57 (d, J=8.2 Hz, 1H), 7.27 (d, J=8.6 Hz, 1H), 6.82 (t, J=8.2 Hz, 1H), 4.07 (t, J=13.8 Hz, 2H), 3.79 (t, J=5.3 Hz, 2H), 3.72 (d, J=1.98 Hz, 2H), 3.42 (t, J=5.3 Hz, 2H), 2.39 (s, 3H); LC/MS (m/z) [M+1]$^+$ 450.2 (calculated for C$_{20}$H$_{23}$F$_3$N$_7$O$_2$, 450.4).

m. N-[2-(Amidinoaminooxy)ethyl]-2-{3-[(2,2-difluoro-2-(5-methylpyridyl)ethyl)amino]-6-cyano-2-fluorophenyl}acetamide hydrochloride

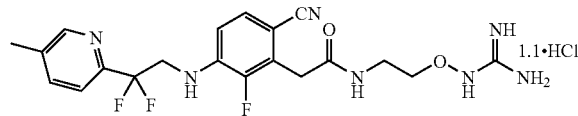

A solution of N-[2-(Amidinoaminooxy)ethyl]-2-{3-[(2,2-difluoro-2-(5-methylpyridyl)ethyl)amino]-6-cyano-2-fluorophenyl}acetamide (1.01 g, 2.24 mmol), as prepared in the previous step, dissolved into CH$_3$CN (25 mL) was treated with 2.0 mL, 2.425 M HCl/CH$_3$CN. The product (900 mg) was collected by filtration and recrystallized from EtOAc/MeOH to afford the final product as a pale yellow solid (800 mg, 1.65 mmol, 74% yield). $^1$H NMR (300 Hz, CDCl$_3$) δ 8.51 (s, 1H), 7.78-7.76 (m, 1H), 7.60 (d, J=8.0 Hz, 1H), 7.31-7.28 (m, 1H), 6.85 (t, J=8.6 Hz, 1H); 4.10 (t, J=14.2 Hz, 2H), 3.94 (t, J=5.3 Hz, 2H), 3.75 (d, J=1.65 Hz, 2H), 3.51 (t, J=5.6 Hz, 2H), 2.42 (s, 3H); LC/MS (m/z) [M+1]$^+$ 450.2 (calculated for C$_{20}$H$_{23}$F$_3$N$_7$O$_2$, 450.4). Elem. Anal. Calc. for free base •1.1 HCl•0.22H$_2$O: C, 48.35; H, 4.73; N, 19.73. Found: C, 48.44; H, 4.47; N, 19.61; Cl, 7.95. Karl Fischer % water: 0.86.

Example 2

N-[2-(Amidinoaminooxy)ethyl]-2-{3-[2-(3-chlorophenyl)-2,2-difluoroethylamino]-6-cyano-2-fluorophenyl}acetamide

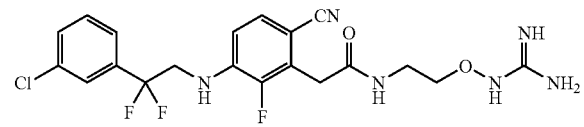

a. (3-Chlorophenyl)difluoroacetic Acid Ethyl Ester

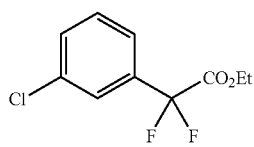

To a mixture of copper bronze (2.93 g, 46.1 mmol) in DMSO (5.0 mL) was added ethyl bromodifluoroacetate (3.2 mL, 25 mmol) under argon at room temperature (see Sato, K. et al; *Chem. Pharm. Bull.* 47:1013-1016, 1999). After stirring for 1 h, 1-chloro-3-iodobenzene (2.57 mL, 20.8 mmol) was added under argon at room temperature. After shaking for 3 days, the mixture was diluted with saturated NH$_4$Cl (50 mL) and extracted with ether (25 mL). The biphasic mixture was filtered through a pad of Celite, and the filter cake was washed with ether (25 mL). The organic layer was separated from the filtrate, and the aqueous layer was extracted with ether (25 mL). The combined organic layers were washed with saturated NH$_4$Cl (2×15 mL) and brine (15 mL), dried (Na$_2$SO$_4$), and concentrated to afford the title compound (4.77 g, 97%) as a clear yellow oil. $^1$H NMR (300 MHz, CDCl3) δ 7.63-7.59 (m, 1H), 7.53-7.45 (m, 2H), 7.43-7.36 (m, 1H), 4.31 (q, J=7.2 Hz, 2H), 1.32 (t, J=7.2 Hz, 3H).

b. 2-(3-Chlorophenyl)-2,2-difluoroacetamide

To a solution of NH$_3$ in MeOH (2 M, 50 mL, 100 mmol) was added (3-chlorophenyl)difluoroacetic acid ethyl ester (4.78 g, 20.4 mmol), as prepared in the preceding step. The homogeneous yellow solution was allowed to sit at room temperature for 13 h, and was then concentrated to provide 3.99 g (95%) of the title compound as a yellow powder. $^1$H NMR (300 MHz, DMSO-d6) δ 8.41 (br, 1H), 8.09 (br, 1H), 7.68-7.60 (m, 2H), 7.59-7.52 (m, 2H).

c. 2-(3-Chlorophenyl)-2,2-difluoroethylamine Hydrochloride

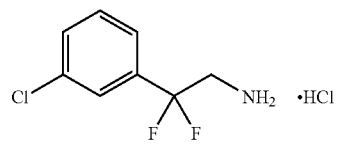

To a solution of borane in THF (1.0 M, 50 mL, 50 mmol) was added 2-(3-chlorophenyl)-2,2-difluoroacetamide (3.99 g, 19.4 mmol), as prepared in the preceding step, and the reaction mixture was refluxed for 9 h. After cooling to room temperature, the homogeneous colorless reaction was treated with water (2 mL) followed by 12 M HCl (6 mL), and was then refluxed for 1 h. The reaction was concentrated, and the residue was taken up in 2.5 M NaOH (30 mL) and extracted with ether (3×15 mL). The combined organic layers were washed with brine (20 mL), dried (Na$_2$SO$_4$), and concentrated to give 5.08 g impure free amine as a dark amber oil. This was dissolved in dry ether (30 mL), HCl (1.0 M in ether, 30 mL, 30 mmol) was added in one portion, and the resulting precipitate was washed with dry ether (3×15 mL) and dried under vacuum to give the title compound (2.96 g, 67%) as a light beige powder. $^1$H NMR (300 MHz, DMSO-d6) δ 8.74 (br, 3H), 7.72 (br, 1H), 7.70-7.64 (m, 1H), 7.63-7.56 (m, 2H), 3.80 (t, J=16.3 Hz, 2H).

d. 2-(3-Chlorophenyl)-2,2-difluoroethylamine

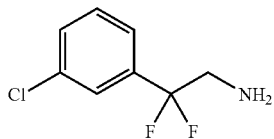

2-(3-chlorophenyl)-2,2-difluoroethylamine hydrochloride (1.65 g, 7.23 mmol), as prepared in the previous step, was taken up with 2.5 M NaOH (4 mL) and extracted with ether (1×8 mL, 1×4 mL). The combined organic layers were dried (Na$_2$SO$_4$) and briefly concentrated to provide 1.44 g (quant. yield) of the title compound as a clear dark brown oil. $^1$H NMR (300 MHz, CDCl$_3$) δ 7.48 (br, 1H), 7.46-7.41 (m, 1H), 7.40-7.34 (m, 2H), 3.17 (t, J=14.5 Hz, 2H), 1.29 (br, 2H).

e. 2-(6-Cyano-2,3-difluorophenyl)malonic Acid Diethyl Ester

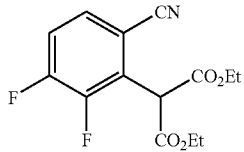

To a mixture of NaH (16.6 g, 657 mmol, dry) in THF (150 mL) was added dropwise over 30 min with stirring at 0-5° C. a solution of diethyl malonate (104.7 g, 654 mmol) in THF (120 mL). To this translucent mixture was then immediately added a solution of 2,3,4-trifluorobenzonitrile (47.7 g, 304 mmol) in THF (50 mL) dropwise with stirring at 0-5° C. The ice bath was then removed and the mixture allowed to stir at room temperature for 4 days. The clear yellow reaction was then diluted with 1 M HCl (350 mL), 4 N HCl was added to pH ~2 (paper), and the mixture was extracted with 1:1 ether/hexanes (1×350 mL, 1×200 mL). The combined organic layers were washed with brine (1×300 mL), dried (Na$_2$SO$_4$), and concentrated to afford the title compound (88.1 g, 98%) as a 1.35:1 mixture of regioisomers. $^1$H NMR of major (desired) regioisomer (300 MHz, CDCl$_3$) δ 7.51 (ddd, J=8.7 Hz, 4.6 Hz, 1.8 Hz, 1H), 7.29 (dt, J=8.9 Hz, 7.2 Hz, 1H), 5.12 (s, 1H), 4.35-4.20 (m, 4H), 1.31 (t, 7.2 J=Hz, 6H).

f. (6-Cyano-2,3-difluorophenyl)acetic Acid Ethyl Ester

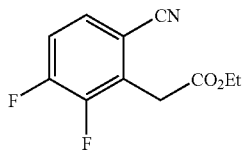

To a solution of 2-(6-cyano-2,3-difluorophenyl)malonic acid diethyl ester (88.1 g, 296 mmol, 1.35:1 mixture of regioisomers), as prepared in the preceding step, in DMSO (350 mL) and water (6.9 mL, 383 mmol) was added LiCl (13.2 g, 311 mmol). The mixture was stirred at 120° C. for 40 min, then allowed to cool to room temperature. The clear amber solution was poured into water (1750 mL) and extracted with ether (3×300 mL). The combined organic layers were washed with brine (500 mL), dried (Na$_2$SO$_4$), and concentrated. Flash chromatography of the residue on silica gel (5:1 hexane/EtOAc) provided 23.26 g (34% over two steps from 2,3,4-trifluorobenzonitrile) of the title compound as a colorless oil. $^1$H NMR (300 MHz, CDCl$_3$) δ 7.48 (ddd, J=8.6 Hz, 4.4 Hz, 1.8 Hz, 1H), 7.23 (dt, J=9.0 Hz, 7.4 Hz, 1H), 4.22 (q, J=7.2 Hz, 2H), 3.93 (d, J=2.0 Hz, 2H), 1.29 (t, J=7.2 Hz, 3H).

g. {3-[2-(3-Chlorophenyl)-2,2-difluoroethylamino]-6-cyano-2-fluorophenyl}acetic Acid Ethyl Ester

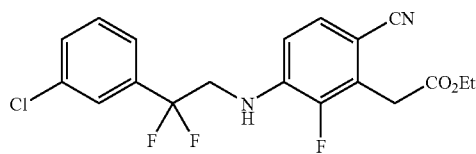

To a solution of DIPEA (1.38 mL, 7.9 mmol), 2-(6-cyano-2,3-difluorophenyl)malonic acid diethyl ester (1.35 g, 6.00 mmol), as prepared in the preceding step, and DMSO (1.7 mL) was added 2-(3-chlorophenyl)-2,2-difluoroethylamine (1.44 g, 7.51 mmol), as prepared in Example 2d. The reaction was stirred under argon at 110° C. for 69 h and then allowed to cool to room temperature. The mixture was diluted with saturated NaHCO$_3$ (15 mL) and extracted with ether (2×15 mL). The combined organic layers were dried (Na$_2$SO$_4$) and concentrated. The residue was purified by flash chromatography on silica gel (3:1 hexane/EtOAc) to afford the title compound (1.525 g, 64%) as a tan crystalline solid. $^1$H NMR (300 MHz, CDCl$_3$) δ 7.51-7.41 (m, 2H), 7.40-7.36 (m, 2H), 7.30 (dd, J=8.6 Hz, 1.3 Hz, 1H), 6.63 (t, J=8.2 Hz, 1H), 4.67 (br, 1H), 4.20 (q, J=7.0 Hz, 2H), 3.84 (d, J=2.0 Hz, 2H), 3.81 (dt, J=13.3 Hz, 6.9 Hz, 2H), 1.29 (t, J=7.1 Hz, 3H). LC/MS (ESI) calcd for C$_{21}$H$_{20}$ClF$_3$N$_3$O$_2$ (MH$^+$.MeCN) 438.1. found 438.2.

h. N-[2-(N',N"-Bis(tert-butoxycarbonyl)amidinoaminooxy)ethyl]-2-{3-[2-(3-chlorophenyl)-2,2-difluoroethylamino]-6-cyano-2-fluorophenyl}acetamide

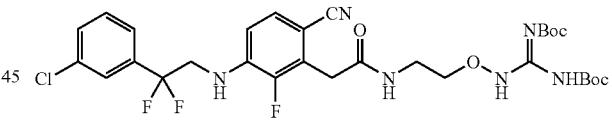

To a solution of LiOH (1.0 M in water, 5.78 mL, 5.78 mmol), MeOH (5.8 mL), and THF (11.6 µL) was added {3-[2-(3-chlorophenyl)-2,2-difluoroethylamino]-6-cyano-2-fluorophenyl}acetic acid ethyl ester (1.525 g, 3.85 mmol), as prepared in the preceding step. After stirring for 1 h at 50° C., the homogeneous yellow solution was cooled in an ice bath and acidified to pH ~2 (paper) with rapid dropwise addition of 0.4 M HCl (14.9 mL, 5.97 mmol) while stirring at 0-5° C. The mixture was immediately extracted with 1:1 hexane/EtOAc (40 mL) and EtOAc (20 mL). The combined organic layers were dried twice (Na$_2$SO$_4$) and concentrated to give the free acid intermediate (1.45 g, 102%) as a light beige powder that was used immediately for the next step without further purification or characterization.

To a mixture of the free acid intermediate (1.45 g, 3.85 mmol), BOP (2.80 g, 6.33 mmol), and the HCl salt of [N,N'-Di(tert-butoxycarbonyl)]2-aminoethoxyguanidine (1.61 g, 4.54 mmol), as prepared in Example 1d, in 1:1 DCM/MeCN (18 mL) was added DIPEA (4.1 mL, 24 mmol) in a rapid stream while stirring on an ice bath. The ice bath was immediately removed, and the homogeneous yellow solution was stirred at room temperature for 8 h. The reaction was concentrated, and flash chromatography on silica gel (hexane/EtOAc 5:6→2:3→1:2) of the residue provided the title compound (2.18 g, 83%) as a white foam. $^1$H NMR (300 MHz, CDCl$_3$) δ 9.14 (br, 1H), 8.26 (t, J=5.0 Hz, 1H), 7.60 (br, 1H), 7.51-7.48 (m, 1H), 7.47-7.41 (m, 1H), 7.40-7.36 (m, 2H), 7.29-7.25 (m, 1H), 6.59 (t, J=8.2 Hz, 1H), 4.64 (dt, J=6.7 Hz, 4.3 Hz, 1H), 4.14 (m, 2H), 3.87 (d, J=1.7 Hz, 2H), 3.78 (dt, J=13.3 Hz, 6.8 Hz, 2H), 3.62 (m, 2H), 1.51 (s, 9H), 1.48 (s, 9H). LC/MS (ESI) calcd for C$_{30}$H$_{37}$ClF$_3$N$_6$O$_6$ (MH$^+$) 669.2. found 669.3.

i. N-[2-(Amidinoaminooxy)ethyl]-2-{3-[2-(3-chlorophenyl)-2,2-difluoroethylamino]-6-cyano-2-fluorophenyl}acetamide

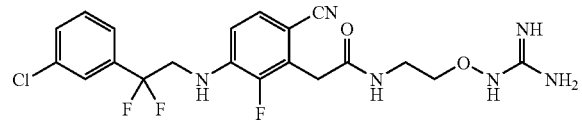

A solution of TFA (7.5 mL, 97 mmol) and anisole (3.0 mL, 27.6 mmol) in DCM (23 mL) was added to N-[2-(N',N''-bis(tert-butoxycarbonyl)amidinoaminooxy)ethyl]-2-{3-[(2,2-difluoro-2-(3-chlorophenyl)ethyl]amino]-6-cyano-2-fluorophenyl}acetamide (2.18 g, 3.26 mmol), as prepared in the preceding step, at room temperature. The dark yellow solution was stirred for 10 h, and then concentrated. The residue was subjected to flash chromatography (DCM/MeOH saturated with gaseous NH$_3$; 95:5→90:10) to yield 1.286 g (84%) of the title compound as a white solid. $^1$H NMR (300 MHz, CD$_3$OD) δ 7.57-7.55 (m, 1H), 7.51-7.40 (m, 3H), 7.27 (dd, J=8.6 Hz, 1.3 Hz, 1H), 6.77 (t, J=8.4 Hz, 1H), 3.93 (t, J=13.6 Hz, 2H), 3.80 (t, J=5.4 Hz, 2H), 3.74 (d, J=2.0 Hz, 2H), 3.43 (t, J=5.4 Hz, 2H). LC/MS (ESI) calcd for C$_{20}$H$_{21}$ClF$_3$N$_6$O$_2$ (MH$^+$) 469.1. found 469.2.

j. N-[2-(Amidinoaminooxy)ethyl]-2-{3-[2-(3-chlorophenyl)-2,2-difluoroethylamino]-6-cyano-2-fluorophenyl}acetamide Hydrochloride

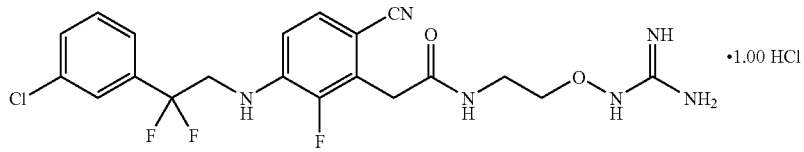

To a homogeneous pale yellow solution of 2-{3-[2-(3-chlorophenyl)-2,2-difluoroethylamino]-6-cyano-2-fluorophenyl}-N-(2-amidinoaminooxyethyl)acetamide (1.28 g, 2.74 mmol), as prepared in the preceding step, in dry MeCN (38 mL) was added anhydrous HCl (0.283 M in MeCN, 10.2 mL, 2.89 mmol) rapidly at room temperature in five ~2 mL portions with swirling. Immediately following addition of the last portion of HCl/MeCN, the solution was allowed to sit undisturbed at room temperature for 15 min, and the resulting crystals were filtered and dried under vacuum to afford the title compound (1.22 g, 88%) as off-white microcrystals. $^1$H NMR (300 MHz, CD$_3$OD) δ 7.57-7.54 (m, 1H), 7.52-7.41 (m, 3H), 7.29 (dd, J=8.6 Hz, 1.3 Hz, 1H), 6.80 (t, J=8.6 Hz, 1H), 3.95 (t, J=5.4 Hz, 2H), 3.94 (t, J=13.7 Hz, 2H), 3.76 (d, J=2.0 Hz, 2H), 3.52 (t, J=5.4 Hz, 2H). LC/MS (ESI) calcd for C$_{20}$H$_{21}$ClF$_3$N$_6$O$_2$ (MH$^+$) 469.1. found 469.1. Elem. Anal. Calc. for free base •1.00 HCl: C, 47.54; H, 4.19; N, 16.63; Cl, 7.02. Found: C, 47.42; H, 4.03; N, 16.62; Cl, 7.02. Karl Fischer % water: <0.10.

Example 3

N-(3-Aminobenzo[d]isoxazol-6-ylmethyl)-2-[6-cyano-3-(2,2-difluoro-2-pyridin-2-yl-ethylamino)-2-fluorophenyl]acetamide

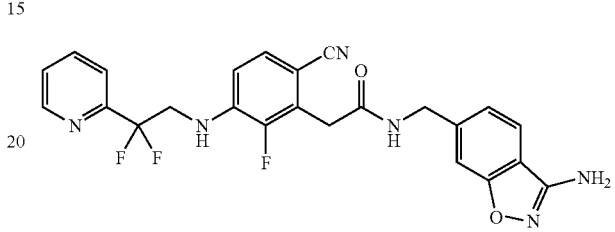

{6-cyano-3-[2,2-difluoro-2-(pyridin-2-yl)ethylamino]-2-fluoro-phenyl}acetic acid ethyl ester (161 mg, 0.444 mmol), prepared analogously to that described for {6-cyano-3-[2,2-difluoro-2-(5-methylpyridin-2-yl)ethylamino]-2-fluorophenyl}acetic acid ethyl ester in Example 1j, was dissolved in THF (0.977 mL) and MeOH (0.488 mL). LiOH (1.0 M in water, 0.488 mL, 0.488 mmol) was added with stirring at room temperature. After 7 h stirring at room temperature, additional LiOH (1.0 M in water, 0.300 mL, 0.300 mmol) was added, and the reaction mixture stirred at 50° C. for 30 min. After cooling to room temperature, 4 M HCl (0.236 mL, 0.944 mmol) was added to pH ~1 (paper). The translucent yellow solution was concentrated, and the residue taken up in toluene (2×2 mL) and concentrated by rotary evaporation followed by high vacuum to afford the free acid intermediate (202 mg, ~100%) contaminated with LiCl, which was used for the next step without further purification or characterization.

To a mixture of the free acid intermediate contaminated with LiCl (38.1 mg, ~84 μmol), BOP (62 mg, 140 μmol), and 6-aminomethylbenzo[d]isoxazol-3-ylamine (19.6 mg, 0.120 mmol), prepared essentially as described previously [Sanderson et al., WO 00/26210 (2000)], in DMF (0.6 mL) was added DIPEA (95 μL, 0.545 mmol) in a rapid stream with stirring at 0-5° C. The ice bath was immediately removed, and the initially immobile paste became an easily stirred white slurry after several minutes shaking at room temperature. After stirring 12 h at room temperature, the mixture was concentrated, diluted with saturated NaHCO$_3$ (4 mL), and extracted with EtOAc (2×4 mL). The combined organic layers were dried (Na$_2$SO$_4$) and concentrated, and the residue was dissolved in hot 9:1 EtOAc/MeOH and adsorbed to silica gel with rotary evaporation. Flash chromatography (9:1 EtOAc/MeOH) provided the title compound (18.9 mg, 47%) as an off-white powder. $^1$H NMR (300 MHz, acetone-d6) δ 8.74-8.69 (m, 1H), 7.97 (dt, J=7.7 Hz, 1.8 Hz, 1H), 7.90 (br, 1H), 7.76-7.69 (m, 2H), 7.57-7.52 (m, 1H), 7.39-7.34 (m, 2H), 7.22 (dd, J=8.2 Hz, 1.2 Hz, 1H), 6.98 (t, J=8.6 Hz, 1H), 6.12 (br, 1H), 5.73 (br, 2H), 4.56 (d, J=5.9 Hz, 2H), 4.26 (dt, J=14.3 Hz, 6.7 Hz, 2H), 3.82 (d, J=2.0 Hz, 2H). LC/MS (ESI) calcd for $C_{24}H_{20}F_3N_6O_2$ (MH$^+$) 481.2. found 481.2.

The following examples were synthesized using the procedures outlined above.

Example 4

N-[2-(Amidinoaminooxy)ethyl]-2-{3-[(2,2-difluoro-2-(4-methylpyridyl)ethyl)amino]-6-cyano-2-fluorophenyl}acetamide trifluoroacetate

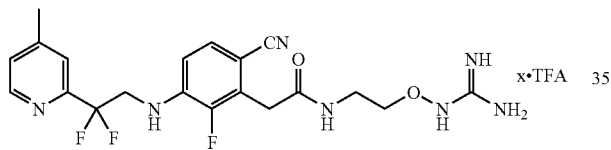

Prepared essentially as described for Example 1a-l, but substituting MeOH/CH2Cl2 (no NH3) as the chromatography elution solvent in Example 1l. 1H NMR (300 Hz, CD$_3$OD) δ 8.49 (d, J=5.3 Hz, 1H), 8.38 (bt, 1H), 7.55 (s, 1H), 7.34 (d, J=5.3 Hz, 1H), 7.29 (d, J=7.2 Hz, 1H), 6.85 (t, J=8.6 Hz, 1H), 4.08 (t, J=14.5 Hz, 2H), 3.95 (t, J=5.3 Hz, 2H), 3.75 (d, J=1.98 Hz, 2H), 3.57-3.46 (m, 2H), 3.34 (s, 1H), 2.41 (s, 3H); LC/MS (m/z) [M+1]$^+$ 450.2 (calculated for $C_{20}H_{22}F_3N_7O_2$, 449.18).

Example 5

N-[2-(Amidinoaminooxy)ethyl]-2-{3-[(2,2-difluoro-2-(6-methylpyridyl)ethyl)amino]-6-cyano-2-fluorophenyl}acetamide

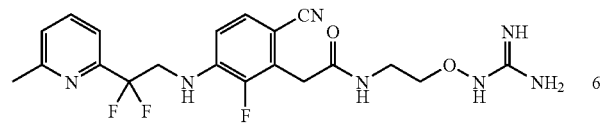

Prepared essentially as described for Example 1a-l. 1H NMR (CD$_3$OD) δ 7.77 (t, J=7.79 Hz, 1H), 7.47 (d, J=7.73 Hz, 1H), 7.34 (d, J=7.80 Hz, 1H), 7.27 (dd, J=8.64 and 1.31 Hz, 1H), 6.85 (t, J=8.47 Hz, H), 4.10 (t, J=13.79 Hz, 2H), 3.79 (t, J=5.22 Hz, 2H), 3.71 (d, J=1.91 Hz, 2H), 3.42 (t, J=5.51 Hz, 2H), 2.58 (s, 3H); LC/MS (m/z) [M+1]$^+$ 450.3 (calculated for $C_{20}H_{23}F_3N_7O_2$, 450.4).

a. N-[2-(Amidinoaminooxy)ethyl]-2-{3-[(2,2-difluoro-2-(6-methylpyridyl)ethyl)amino]-6-cyano-2-fluorophenyl}acetamide Hydrochloride

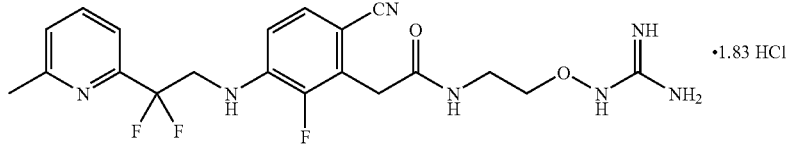

Prepared from N-[2-(Amidinoaminooxy)ethyl]-2-{3-[(2,2-difluoro-2-(6-methylpyridyl)ethyl)amino]-6-cyano-2-fluorophenyl}acetamide, as described in the previous step, using the protocol given in Example 1m, except the product collected by filtration was not recrystallized. $^1$H NMR (CD$_3$OD) δ 8.38 (m, 1H), 7.91 (m, 2H), 7.33 (d, J=8.73 Hz, 1H), 6.92 (t, J=8.65 Hz, 1H), 4.20 (t, J=13.40 Hz, 2H), 3.96 (t, J=5.37 Hz, 2H), 3.78 (d, J=1.91 Hz, 2H), 3.52 (t, J=5.33 Hz, 2H), 2.79 (s, 3H); LC/MS (m/z) [M+1]$^+$ 450.4 (calculated for $C_{20}H_{22}F_3N_7O_2$, 449.18). Elem. Anal. Calc.: C, 45.99; H, 4.63; N, 18.77; Cl, 13.57. Found: C, 45.97; H, 4.40; N, 18.60; Cl, 12.39. Karl Fischer % water, 1.42. One mole free base contains 1.83 mol HCl and 0.41 mol water.

Example 6

N-[2-(Amidinoaminooxy)ethyl]-2-{3-[(2,2-difluoro-2-(3-methylpyridyl)ethyl)amino]-6-cyano-2-fluorophenyl}acetamide trifluoroacetate

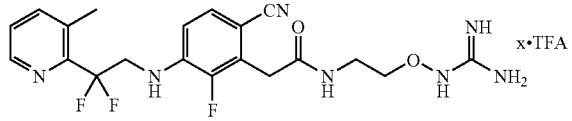

Prepared essentially as described for Example 1a-l, but substituting MeOH/CH$_2$Cl$_2$ (no NH$_3$) as the chromatography elution solvent in Example 1l. 1H NMR (300 Hz, CD$_3$OD) δ 8.51-8.32 (m, 2H), 7.72 (d, J=7.9 Hz, 1H), 7.46-7.27 (m, 2H), 6.90 (t, J=7.9 Hz, 1H), 4.25 (t, J=13.8 Hz, 2H), 3.95 (t, J=5.3 Hz, 2H), 3.76 (d, J=1.98 Hz, 2H), 3.59-3.45 (m, 2H), 2.92-2.85 (m, 1H), 2.58 (s, 3H); LC/MS (m/z) [M+1]$^+$ 450.2 (calculated for $C_{20}H_{22}F_3N_7O_2$, 449.18).

Example 7

N-[2-(Amidinoaminooxy)ethyl]-2-{3-[(2,2-difluoro-2-(quinolin-8-yl)ethyl)amino]-6-cyano-2-fluorophenyl}acetamide

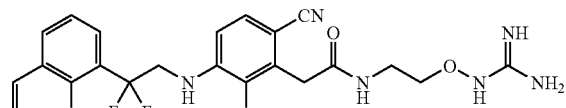

a. 2-Chloro-1-quinolin-8-yl-ethanone

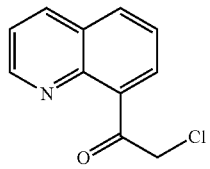

To a solution of n-BuLi (28 mL, 44.0 mmol, 1.6M in hexanes) at −78° C. was added a solution of 8-bromoquinoline (8.5 g, 40.0 mmol) in Et$_2$O (60 mL) over 20 minutes. After stirring for 22 minutes, a solution of 2-chloro-N-methoxy-N-methylacetamide (5.7 g, 41 mmol) in THF (35 mL) was added over 12 minutes (see Tillyer, R. et al; *Synlett* 225-226, 1996; and Dolling, U. H. et al; U.S. Pat. No. 5,786,515). After 3 hours the reaction was poured into 11 mL, 4N HCl. The aqueous phase was neutralized to pH 7 using solid NaHCO$_3$ and partitioned with Et$_2$O (2×100 mL). The combined organic phase was washed with brine (50 mL), dried over Na$_2$SO$_4$ and concentrated in vacuo. Purification via SiO$_2$ chromatography (20% EtOAc/hexanes) afforded the product as a yellow solid (4.2 g). 1H NMR (300 Hz, CDCl$_3$) δ 9.0-8.96 (m, 1H), 8.26-8.19 (m, 2H), 8.04-8.01 (m, 1H), 7.68-7.63 (m, 1H), 7.52-7.48 (m, 1H), 5.37 (s, 2H).

b. 2-Azido-1-quinolin-8-yl-ethanone

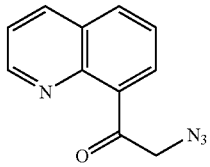

To a solution of 2-chloro-1-quinolin-8-yl-ethanone (5.85 g, 28.5 mmol) in DMSO (60 mL), as prepared in the last step, was added NaN$_3$ (2.2 g, 33.9 mmol). After 2 hours, the reaction was diluted with EtOAc (250 mL) and washed with H$_2$O (3×100 mL). The organic phase was washed with brine (100 mL), dried over Na$_2$SO$_4$ and concentrated in vacuo. Purification via SiO$_2$ chromatography (20% EtOAc/hexanes) afforded the product as a pale yellow solid (4.95 g). 1H NMR (300 Hz, CDCl$_3$) δ 9.0-8.97 (m, 1H), 8.26-8.22 (m, 2H), 8.04-8.02 (m, 1H), 7.68-7.63 (m, 1H), 7.52-7.48 (m, 1H), 5.12 (s, 2H).

c. 8-(2-Azido-1,1-difluoro-ethyl)-quinoline

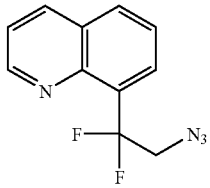

A cooled solution of 2-azido-1-quinolin-8-yl-ethanone (8.79 g, 41.46 mmol), as prepared in the last step, in CH$_2$Cl$_2$ (21 mL) at 4° C. was treated with DAST (12.2 mL, 91.21 mmol) and TFA (640 μL, 8.29 mmol). After 19 hours the reaction was added dropwise to NaHCO$_3$ $_{(satd)}$ at 4° C. The aqueous phase was washed with EtOAc (100 mL), the combined organic phase was washed with brine (100 mL) and concentrated in vacuo. Purification via SiO$_2$ chromatography (5% EtOAc/hexanes) afforded the product as a yellow oil (4.94 g). 1H NMR (300 Hz, CDCl$_3$) δ 9.0-8.96 (m, 1H), 8.24-8.20 (m, 1H), 8.09 (d, J=7.3 Hz, 1H), 7.97 (d, J=8.3 Hz, 1H), 7.63 (t, J=7.6 Hz, 1H), 7.50-7.46 (m, 1H), 4.51 (t, J=13.9 Hz, 2H); LC/MS (m/z) [M+1]$^+$ 235.1 (calculated for C$_{11}$H$_8$F$_2$N$_4$, 234.20).

d. 2,2-Difluoro-2-quinolin-8-yl-ethylamine

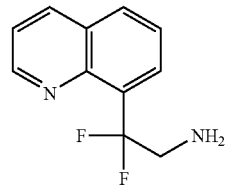

A solution of 8-(2-azido-1,1-difluoro-ethyl)-quinoline (3.8 g, 16.24 mmol) in MeOH (20 mL), as prepared in the last step, was treated with 10 wt. % Pd—C (754 mg) and NH$_4$HCO$_2$ (3 g). After 45 minutes the reaction was filtered through a pad of Celite and partitioned between EtOAc (100 mL) and NaHCO$_3$ $_{(satd)}$ (100 mL). The organic phase was washed with brine (100 mL), dried over Na$_2$SO$_4$ and concentrated in vacuo to afford the product as a yellow viscous oil (2.7 g). 1H NMR (300 Hz, CDCl$_3$) δ 9.0-8.98 (m, 1H), 8.22-8.19 (m, 1H), 8.05 (d, J=7.3 Hz, 1H), 7.93 (d, J=8.2 Hz, 1H), 7.60 (t, J=7.7 Hz, 1H), 7.49-7.45 (m, 1H), 3.82 (t, J=15.3 Hz, 2H); LC/MS (m/z) [M+1]$^+$ 209.2 (calculated for C$_{11}$H$_{10}$F$_2$N$_2$, 208.21).

e. N-[2-(Amidinoaminooxy)ethyl]-2-{3-[(2,2-difluoro-2-(quinolin-8-yl)ethyl)amino]-6-cyano-2-fluorophenyl}acetamide

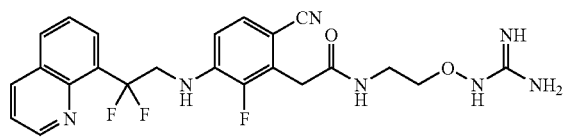

Prepared essentially as described in Example 1j-1l. $^1$H NMR (300 Hz, CD$_3$OD) δ 9.07-9.04 (m, 1H), 8.40 (d, J=8.3 Hz, 1H), 8.07-8.00 (m. 2H), 7.65-7.58 (m, 2H), 7.23 (d, J=8.6 Hz, 1H), 7.07 (t, J=8.7 Hz, 1H), 4.51 (t, J=14.8 Hz, 2H), 3.80 (t, J=5.4 Hz, 2H), 3.71 (d, J=1.9 Hz, 2H), 3.42 (t, J=5.4 Hz, 2H); LC/MS (m/z) [M+1]$^+$ 486.3 (calculated for C$_{23}$H$_{22}$F$_3$N$_7$O$_2$, 485.18).

f. N-[2-(Amidinoaminooxy)ethyl]-2-{3-[(2,2-difluoro-2-(quinolin-8-yl)ethyl)amino]-6-cyano-2-fluorophenyl}acetamide Hydrochloride

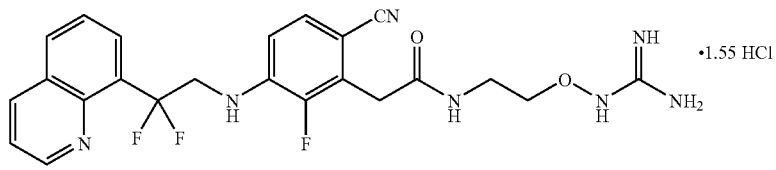

Prepared from N-[2-(Amidinoaminooxy)ethyl]-2-{3-[(2, 2-difluoro-2-(quinolin-8-yl)ethyl)amino]-6-cyano-2-fluorophenyl}acetamide (prepared in the previous step) using essentially the protocol given in Example 1m. 1H NMR (300 Hz, CD$_3$OD) δ 9.09-9.01 (m, 1H), 8.42-8.36 (m, 2H), 8.09-7.99 (m, 2H), 7.68-7.57 (m, 2H), 7.26 (d, J=8.6 Hz, 1H), 7.09 (t, J=8.6 Hz, 1H), 4.51 (t, J=15.1 Hz, 2H), 3.95 (t, J=5.9 Hz, 2H), 3.75 (d, J=1.98 Hz, 2H), 3.57-3.47 (m, 2H), 3.34 (s, 1H); LC/MS (m/z) [M+1]$^+$ 486.3 (calculated for C$_{23}$H$_{22}$F$_3$N$_7$O$_2$, 485.18). Elem. Anal. Calc. for free base •1.55 HCl•0.06H$_2$O: C, 50.87; H, 4.39; N, 18.05. Found: C, 50.70; H, 4.29; N, 17.99; Cl, 9.99. Karl Fischer % water: 0.23.

Example 8

N-(6-Amino-2-methyl-pyridin-3-ylmethyl)-2-[6-cyano-3-(2,2-difluoro-2-pyridin-2-yl-ethylamino)-2-fluoro-phenyl]-acetamide

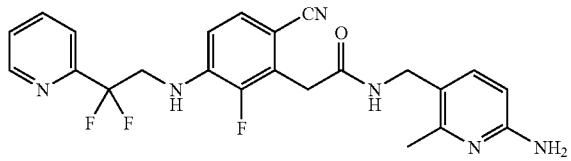

Prepared essentially as described in Examples 1k-l, using (5-aminomethyl-6-methyl-pyridin-2-yl)-carbamic acid tert-butyl ester (Sanderson, P. E. J. et al; J. Med. Chem. 41:4466, 1998) as the amine coupling partner. 1H NMR (300 Hz, CD$_3$OD) δ 8.67 (d, J=5.2 Hz, 1H), 7.92 (t, J=7.3 Hz, 1H), 7.69 (d, J=7.9 Hz, 1H), 7.53-7.48 (m, 1H), 7.35 (d, J=8.5 Hz, 1H), 7.27 (d, J=8.6 Hz, 1H), 6.83 (t, J=8.1 Hz, 1H), 6.39 (d, J=7.9 Hz, 1H), 4.25 (s, 2H), 4.11 (t, J=14.2 Hz, 2H), 3.71 (d, J=1.8 Hz, 2H), 2.33 (s, 3H); LC/MS (m/z) [M+1]$^+$ 455.1 (calculated for C$_{23}$H$_{21}$F$_3$N$_6$O, 454.17).

a. N-(6-Amino-2-methyl-pyridin-3-ylmethyl)-2-[6-cyano-3-(2,2-difluoro-2-pyridin-2-yl-ethylamino)-2-fluoro-phenyl]-acetamide hydrochloride

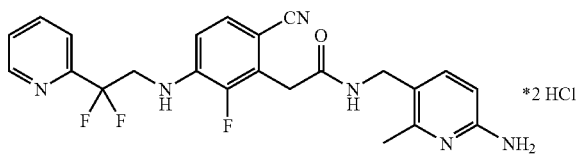

Prepared from N-(6-Amino-2-methyl-pyridin-3-ylmethyl)-2-[6-cyano-3-(2,2-difluoro-2-pyridin-2-yl-ethylamino)-2-fluoro-phenyl]-acetamide, as described in the previous step, using essentially the protocol given in Example 1m. 1H NMR (300 Hz, CD$_3$OD) δ 8.69 (d, J=4.6 Hz, 1H), 8.10-8.00 (m, 1H), 7.83 (d, J=9.2 Hz, 1H), 7.77 (d, J=7.9 Hz, 1H), 7.67-7.57 (m, 1H), 7.33-7.24 (m, 1H), 6.91-6.78 (m, 2H), 4.27 (s, 2H), 4.13 (t, J=13.8 Hz, 2H), 3.74 (d, J=1.98 Hz, 2H), 2.51 (s, 3H); LC/MS (m/z) [M+1]$^+$455.1 (calculated for C$_{23}$H$_{21}$F$_3$N$_6$O, 454.17). Elem. Anal. Calc. for free base •2.0 HCl •0.75H$_2$O: C, 51.07; H, 4.57; N, 15.54. Found: C, 50.85; H, 4.31; N, 15.40.

Example 9

N-(6-Amino-pyridin-3-ylmethyl)-2-[6-cyano-3-(2,2-difluoro-2-pyridin-2-yl-ethylamino)-2-fluoro-phenyl]-acetamide

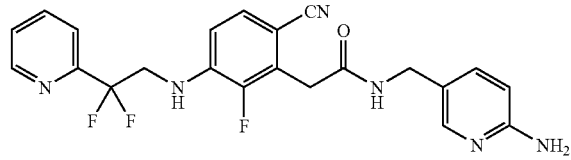

Prepared essentially as described in Example 1k, using 5-aminomethyl-pyridin-2-ylamine (Feng, D.-M. et al; J. Med. Chem. 40:3726, 1997) as the amine coupling partner. 1H NMR (300 Hz, CD$_3$OD) δ 8.65 (d, J=5.3 Hz, 1H), 7.97-7.88 (m, 1H), 7.82 (bs, 1H), 7.69 (d, J=7.9 Hz, 1H), 7.54-7.47 (m, 1H), 7.47-7.41 (m, 1H), 7.27 (d, J=8.6 Hz, 1H), 6.83 (t, J=8.6 Hz, 1H), 6.55 (d, J=8.6 Hz, 1H), 6.43-6.39 (m, 1H), 4.27 (s, 2H), 4.19-4.04 (m, 2H), 3.71 (d, J=1.98 Hz, 2H), 3.34 (s, 2H); LC/MS (m/z) [M+1]$^+$ 441.3 (calculated for C$_{22}$H$_{19}$F$_3$N$_6$O, 440.16).

Example 10

N-[2-(Amidinoaminooxy)ethyl]-2-{3-[(2,2-difluoro-2-pyridylethyl)amino]-6-cyano-2-fluorophenyl}acetamide

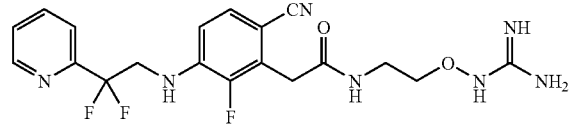

Prepared essentially as described for Example 1a-l. 1H NMR (300 Hz, CD$_3$OD) δ 8.68-8.64 (m, 1H), 7.93 (dt, J=7.8 Hz, 1.6 Hz, 1H), 7.70 (dt, J=7.9 Hz, 0.9 Hz, 1H), 7.51 (dd, J=7.6 Hz, 4.9 Hz, 1H), 7.28 (dd, J=8.6 Hz, 1.2 Hz, 1H), 6.83 (t, J=8.5 Hz, 1H), 4.12 (t, J=13.9 Hz, 2H), 3.80 (t, J=5.5 Hz, 2H), 3.72 (d, J=1.9 Hz, 2H), 3.43 (t, J=5.4 Hz, 2H); LC/MS (m/z) [M+1]$^+$ 436.2 (calculated for C$_{19}$H$_{20}$F$_3$N$_7$O$_2$, 435.16).

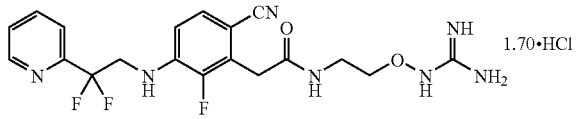

Prepared from N-[2-(Amidinoaminooxy)ethyl]-2-{3-[(2, 2-difluoro-2-pyridylethyl)amino]-6-cyano-2-fluorophenyl}acetamide (prepared in the previous step) using essentially the protocol given in Example 1m, except the product collected by filtration was not recrystallized. 1H NMR (300 Hz, CD$_3$OD) δ 8.75 (d, J=5.3 Hz, 1H), 8.23-8.14 (m, 1H), 7.90 (d, J=7.2 Hz, 1H), 7.78-7.69 (m, 1H), 7.31 (dd, J=8.6 Hz, 1.3 Hz, 1H), 6.88 (t, J=8.6 Hz, 1H), 4.16 (t, J=13.8 Hz, 2H), 3.96 (t, J=5.3 Hz, 2H), 3.76 (d, J=1.3 Hz, 2H), 3.52 (t, J=5.3 Hz, 2H); LC/MS (m/z) [M+1]$^+$ 436.2 (calculated for C$_{19}$H$_{20}$F$_3$N$_7$O$_2$, 435.16). Elem. Anal. Calc. for free base •1.70 HCl•0.89 water: C, 44.45; H, 4.61; N, 19.10; Cl, 11.74. Found: C, 44.7; H, 4.38; N, 19.22; Cl, 11.75.

Example 11

N-[2-(Amidinoaminooxy)ethyl]-2-{3-[(2,2-difluoro-2-phenylethyl)amino]-6-cyano-2-fluorophenyl}acetamide hydrochloride

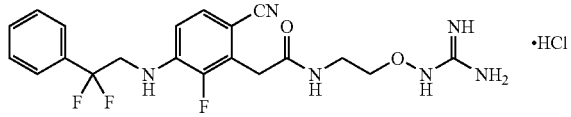

Prepared essentially as described for Example 2a-j. 1H NMR (300 Hz, CD$_3$OD) δ 7.57-7.51 (m, 2H), 7.49-7.43 (m, 3H), 7.27 (dd, J=8.6 Hz, 1.3 Hz, 1H), 6.77 (t, J=8.6 Hz, 1H), 3.98-3.90 (m, 4H), 3.76 (d, J=1.98 Hz, 2H), 3.52 (t, J=5.3 Hz, 2H); LC/MS (m/z) [M+1]$^+$ 435.2 (calculated for C$_{20}$H$_{21}$F$_3$N$_6$O$_2$, 434.17).

Example 12

N-[2-(Amidinoaminooxy)ethyl]-2-{3-[(2,2-difluoro-2-(3-fluorophenyl)ethyl)amino]-6-cyano-2-fluorophenyl}acetamide hydrochloride

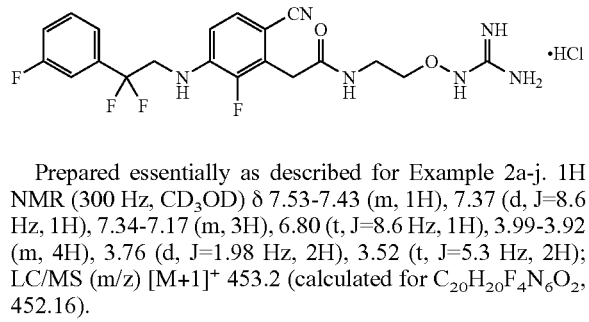

Prepared essentially as described for Example 2a-j. 1H NMR (300 Hz, CD$_3$OD) δ 7.53-7.43 (m, 1H), 7.37 (d, J=8.6 Hz, 1H), 7.34-7.17 (m, 3H), 6.80 (t, J=8.6 Hz, 1H), 3.99-3.92 (m, 4H), 3.76 (d, J=1.98 Hz, 2H), 3.52 (t, J=5.3 Hz, 2H); LC/MS (m/z) [M+1]$^+$ 453.2 (calculated for C$_{20}$H$_{20}$F$_4$N$_6$O$_2$, 452.16).

Example 13

N-[2-(Amidinoaminooxy)ethyl]-2-{3-[(2,2-difluoro-2-(3,4-difluorophenyl)ethyl)amino]-6-cyano-2-fluorophenyl}acetamide

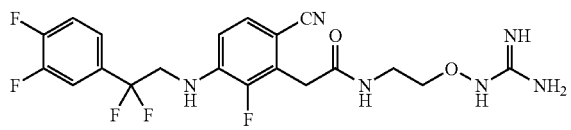

Prepared essentially as described for Example 2a-i. 1H NMR (300 Hz, CD$_3$OD) δ 7.54-7.46 (m, 1H), 7.40-7.33 (m, 2H), 7.28 (dd, J=8.6 Hz, 1.3 Hz, 1H), 6.79 (t, J=8.2 Hz, 1H), 3.93 (t, J=13.8 Hz, 2H), 3.80 (t, J=5.3 Hz, 2H), 3.74 (d, J=2.0 Hz, 2H), 3.43 (t, J=5.3 Hz, 2H); LC/MS (m/z) [M+1]$^+$ 471.2 (calculated for C$_{20}$H$_{19}$F$_5$N$_6$O$_2$, 470.15).

a. N-[2-(Amidinoaminooxy)ethyl]-2-{3-[(2,2-difluoro-2-(3,4-difluorophenyl)ethyl)amino]-6-cyano-2-fluorophenyl}acetamide hydrochloride

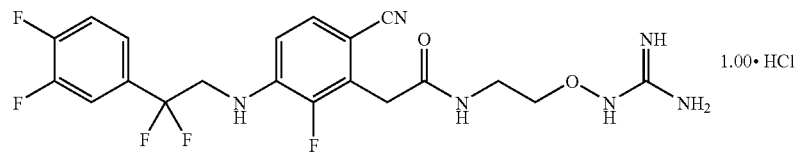

Prepared from N-[2-(Amidinoaminooxy)ethyl]-2-{3-[(2,2-difluoro-2-(3,4-difluorophenyl)ethyl)amino]-6-cyano-2-fluorophenyl}acetamide, as described in the previous step, using essentially the protocol given in Example 2j. 1H NMR (300 Hz, CD$_3$OD) δ 7.55-7.45 (m, 1H), 7.41-7.26 (m, 3H), 6.80 (t, J=8.6 Hz, 1H), 3.99-3.91 (m, 4H), 3.76 (d, J=1.98 Hz, 2H), 3.52 (t, J=5.3 Hz, 2H); LC/MS (m/z) [M+1]$^+$ 471.2 (calculated for C$_{20}$H$_{19}$F$_5$N$_6$O$_2$, 470.15). Elem. Anal. Calc. for free base•1.00 HCl: C, 47.39; H, 3.98; N, 16.58; Cl, 6.99. Found: C, 47.39; H, 3.74; N, 16.57; Cl, 7.01. Karl Fischer % water: <0.10.

Example 14

N-[2-(Amidinoaminooxy)ethyl]-2-{6-cyano-3-[2,2-difluoro-2-(6-methyl-1-oxy-pyridin-2-yl)-ethylamino]-2-fluoro-phenyl}acetamide

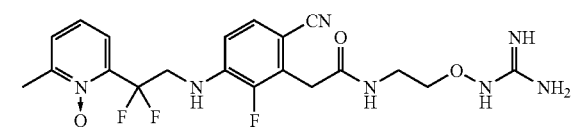

a. Methanesulfonic acid 2,2-difluoro-2-(6-methyl-pyridin-2-yl)-ethyl Ester

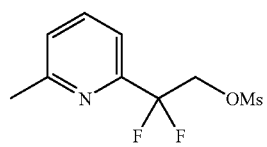

To a solution of 2,2-difluoro-2-(6-methyl-pyridin-2-yl)-ethanol (2.82 g, 16.3 mmol) (prepared essentially as described in Example 1f) in anhydrous THF (60 mL) at 0° C.

was added methanesulfonyl chloride (1.52 mL, 19.6 mmol), followed by triethylamine (4.54 mL, 32.6 mmol). After 2.5 hours, the reaction mixture was quenched with ice/water. The resulting mixture was extracted with ethyl acetate. The combined organic layers were dried over $Na_2SO_4$ and evaporated to afford the desired product as a clear oil (3.7 g, 97%). $^1$H NMR ($CDCl_3$) δ 7.73 (t, J=7.77 Hz, 1H), 7.51 (d, J=7.75 Hz, 1H), 7.28 (d, J=8.04 Hz, 1H), 4.89 (t, J=12.88 Hz, 2H), 3.07 (s, 3H), 2.58 (s, 3H); LC/MS (m/z) [M+1] 252.2 (calculated for $C_9H_{12}F_2NO_3S$, 252.0).

b. 2-(2-Azido-1,1-difluoro-ethyl)-6-methyl-pyridine

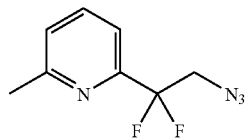

Methanesulfonic acid 2,2-difluoro-2-(6-methyl-pyridin-2-yl)-ethyl ester (900 mg, 3.83 mmol), as prepared in the preceding step, was dissolved in DMSO (2 mL). To this solution was added sodium azide (498 mg, 7.65 mmol) and the reaction mixture was heated at 180° C. under microwave irradiation for 1 hour. The reaction mixture was partitioned between water and ethyl acetate. The combined ethyl acetate extracts were dried over $Na_2SO_4$ and concentrated to afford a brown residue (700 mg, 92%). $^1$H NMR ($CDCl_3$) δ 7.73 (t, J=7.82 Hz, 1H), 7.52 (d, J=7.76 Hz, 1H), 7.26 (d, J=7.79 Hz, 1H), 4.02 (t, J=13.23 Hz, 2H), 2.50 (s, 3H).

c. 2,2-Difluoro-2-(6-methyl-pyridin-2-yl)-ethylamine

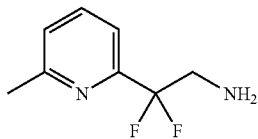

A solution of 2-(2-Azido-1,1-difluoro-ethyl)-6-methyl-pyridine (700 mg, 3.54 mmol), as prepared in the preceding step, in MeOH (10 mL) was treated with 10% Pd/C (150 mg) under 39 Psi $H_2$ atmosphere overnight. The reaction mixture was filtered through a pad of celite and the filtrate was evaporated to afford the product as a brown oil (605 mg, 99%). $^1$H NMR ($CDCl_3$) δ 7.69 (t, J=7.74 Hz, 1H), 7.46 (d, J=7.70 Hz, 1H), 7.22 (d, J=7.81 Hz, 1H), 3.42 (t, J=14.40 Hz, 2H), 2.58 (s, 3H); LC/MS (m/z) [M+1] 173.2 (calculated for $C_8H_{11}F_2N_2$, 173.1).

d. {6-Cyano-3-[2,2-difluoro-2-(6-methyl-pyridin-2-yl)-ethylamino]-2-fluoro-phenyl}-acetic Acid Ethyl Ester

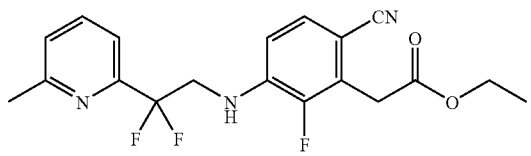

A mixture of 2,2-Difluoro-2-(6-methyl-pyridin-2-yl)-ethylamine (223.6 mg, 1.3 mmol), as prepared in the preceding step, and (6-cyano-2,3-difluoro-phenyl)-acetic acid ethyl ester (225 mg, 1.0 mmol), as prepared in Example 2f, was dissolved in DMSO (1.0 mL) and heated at 150° C. under microwave irradiation for 1 hour. The reaction mixture was partitioned between ethyl acetate and water. The combined EtOAc extracts were dried over $Na_2SO_4$ and evaporated. The crude product was purified by flash column chromatography on silica gel (EtOAc/hexanes 2/1, v/v) to afford the product as a white solid (208 mg, 42.5% yield based on the initial amine). $^1$H NMR ($CDCl_3$) δ 7.71 (t, J=8.02 Hz, 1H), 7.47 (d, J=8.15 Hz, 1H), 7.30 (dd, J=8.61 and 1.28 Hz, 1H), 7.25 (m, 1H), 6.79 (t, J=8.28 Hz, 1H), 4.18 (q, J=7.16 Hz, 2H), 4.12 (t, J=13.21 Hz, 2H), 3.81 (d, J=2.0 Hz, 2H), 2.60 (s, 3H), 1.27 (t, J=7.13 Hz, 3H); LC/MS (m/z) [M+1] 378.3 (calculated for $C_{19}H_{19}F_3N_3O_2$, 378.1).

e. {6-Cyano-3-[[2,2-difluoro-2-(6-methyl-pyridin-2-yl)-ethyl]-(2,2,2-trifluoro-acetyl)-amino]-2-fluoro-phenyl}-acetic Acid Ethyl Ester

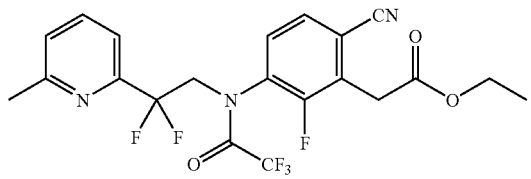

{6-Cyano-3-[2,2-difluoro-2-(6-methyl-pyridin-2-yl)-ethylamino]-2-fluoro-phenyl}-acetic acid ethyl ester (119.1 mg, 0.316 mmol), as prepared in the preceding step, was dissolved in $CH_2Cl_2$ (2 mL). To this solution were added DIEA (0.066 mL, 0.379 mmol) and TFAA (0.220 mL, 1.58 mmol) dropwise at 0° C. After 3 hours, the reaction mixture was partitioned between $CH_2Cl_2$ and water. The organic layers were combined, dried over $Na_2SO_4$, and evaporated. The residue was purified by flash column chromatography on silica gel (EtOAc/hexanes 1/1, v/v) to afford the desired product (142 mg, 95%). $^1$H NMR ($CDCl_3$) δ 7.73 (t, J=8.79 Hz, 1H), 7.70 (t, J=7.88 Hz, 1H), 7.58 (t, J=7.77 Hz, 1H), 7.48 (t, J=8.44 Hz, 1H), 7.24 (t, J=7.55 Hz, 1H), 5.07 (m, 2H), 4.25 (q, J=7.16 Hz, 2H), 3.94 (d, J=1.17 Hz, 2H), 2.49 (s, 3H), 1.26 (t, J=7.14 Hz, 3H); LC/MS (m/z) [M+1] 474.3 (calculated for $C_{21}H_{18}F_6N_3O_3$, 474.1).

f. {6-Cyano-3-[[2,2-difluoro-2-(6-methyl-1-oxy-pyridin-2-yl)-ethyl]-(2,2,2-trifluoro-acetyl)-amino]-2-fluoro-phenyl}-acetic Acid Ethyl Ester

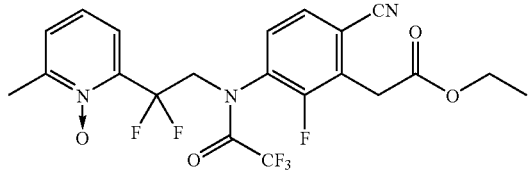

{6-Cyano-3-[[2,2-difluoro-2-(6-methyl-pyridin-2-yl)-ethyl]-(2,2,2-trifluoro-acetyl)-amino]-2-fluoro-phenyl}-acetic acid ethyl ester (141.9 mg, 0.30 mmol), as prepared in the preceding step, was dissolved in $CH_2Cl_2$ (0.3 mL). To this solution were added methyltrioxorhenium (VII) (6 mg, 0.013 mmol) and 30% aq. $H_2O_2$ (0.072 mL, 0.64 mmol). The reaction mixture was stirred at room temperature for 24 hours and concentrated. The brown residue was purified by flash column chromatography on silica gel (EtOAc/hexanes 2/1, v/v) to afford the desired product (34 mg, 23.1%). $^1$H NMR (CDCl$_3$) δ 7.58 (d, J=8.18 Hz, 1H), 7.49 (d, J=8.32 Hz, 1H), 7.39 (t, J=7.25 Hz, 1H), 7.28 (t, J=7.77 Hz, 1H), 5.16 (m, 2H), 4.78 (q, J=13.8 Hz, 2H), 4.20 (q, J=7.08 Hz, 2H), 3.92 (d, J=1.17 Hz, 2H), 2.44 (s, 3H), 1.26 (t, J=7.12 Hz, 3H); LC/MS (m/z) [M+1] 490.3 (calculated for C$_{21}$H$_{18}$F$_6$N$_3$O$_4$, 490.1).

g. {6-Cyano-3-[2,2-difluoro-2-(6-methyl-1-oxy-pyridin-2-yl)-ethylamino]-2-fluoro-phenyl}-acetic Acid

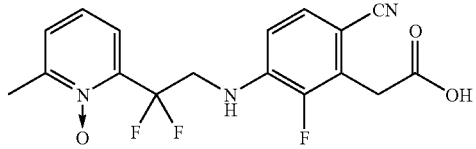

{6-Cyano-3-[[2,2-difluoro-2-(6-methyl-1-oxy-pyridin-2-yl)-ethyl]-(2,2,2-trifluoro-acetyl)-amino]-2-fluoro-phenyl}-acetic acid ethyl ester (34 mg, 0.0695 mmol), as prepared in the preceding step, was dissolved in MeOH/THF/H$_2$O (1.5 mL, 3:2:1) and treated with LiOH monohydrate (8.8 mg, 0.21 mmol). After 3 hours, the reaction mixture was neutralized with 1.0 mL of 2 N HCl and concentrated in vacuo. The crude material was diluted with toluene and concentrated to afford the desired product as a white solid (25.4 mg). This material was used for the next step coupling reaction without further purification. $^1$H NMR (CD$_3$OD) δ 7.62 (t, J=7.5 Hz, 1H), 7.61 (t, J=8.1 Hz, 1H), 7.43 (t, J=8.1 Hz, 1H), 7.24 (dd, J=9.0 and 1.2 Hz, 1H), 6.98 (t, J=8.4 Hz, 1H), 4.43 (t, J=13.8 Hz, 2H), 3.74 (d, J=2.1 Hz, 2H), 2.54 (s, 3H).

h. N-[2-(Amidinoaminooxy)ethyl]-2-{6-cyano-3-[2,2-difluoro-2-(6-methyl-1-oxy-pyridin-2-yl)-ethylamino]-2-fluoro-phenyl}acetamide

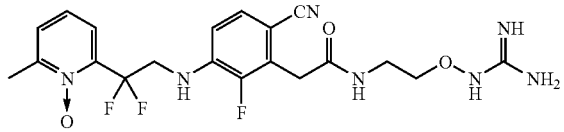

{6-Cyano-3-[2,2-difluoro-2-(6-methyl-1-oxy-pyridin-2-yl)-ethylamino]-2-fluorophenyl}-acetic acid (25.4 mg, 0.0695 mmol), as prepared in the preceding step, HCl salt of [N,N'-di(tert-butoxycarbonyl)]-2-aminoethoxyguanidine (34.5 mg, 0.097 mmol), HOBT (13.8 mg, 0.09 mmol), as prepared in Example 1d, and HBTU (34.3 mg, 0.09 mmol) were dissolved in anhydrous THF (3 mL) at room temperature. DIEA (44.8 mg, 0.35 mmol) was added dropwise and the reaction mixture was kept stirring overnight, then concentrated under reduced pressure. The residue was partitioned between ethyl acetate and water. The organic extracts were dried over Na$_2$SO$_4$, and evaporated to afford the crude product. This crude product was used for the next reaction without purification. To the t-BOC protected precursor in a 25-mL round bottom flask was added 30% TFA/CH$_2$Cl$_2$ (4 mL) at 0° C. The reaction mixture was stirred at room temperature for 2 hours and the organic solvents were evaporated. The resulting residue was diluted with NH$_3$-saturated CH$_2$Cl$_2$, concentrated. The crude product was purified by flash column chromatography on silica gel (NH$_3$-saturated 10% MeOH/CH$_2$Cl$_2$) to afford the product as a white solid (20 mg, 62% yield). $^1$H NMR (CD$_3$OD) δ 7.61 (t, J=8.59 Hz, 1H), 7.60 (t, J=7.83 Hz, 1H), 7.43 (t, J=8.0 Hz, 1H), 7.24 (dd, J=8.64 and 1.25 Hz, 1H), 6.98 (t, J=8.27 Hz, 1H), 4.40 (t, J=13.95 Hz, 2H), 3.79 (t, J=5.50 Hz, 2H), 3.69 (d, J=1.91 Hz, 2H), 3.42 (t, J=5.40 Hz, 2H), 2.54 (s, 3H); LC/MS (m/z) [M+1] 466.4 (calculated for C$_{20}$H$_{23}$F$_3$N$_7$O$_3$, 466.2)

Example 15

N-[2-(Amidinoaminooxy)ethyl]-2-{3-[(2,2-difluoro-2-(5-chloropyridin-2-yl)ethyl)amino]-6-cyano-2-fluorophenyl}acetamide

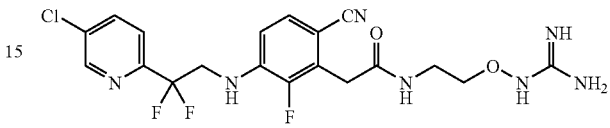

a. 2,2-Difluoro-2-(5-chloro-pyridin-2-yl)-ethylamine

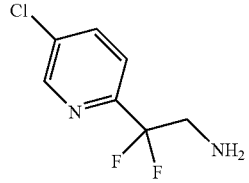

To a solution of 2-(2-Azido-1,1-difluoro-ethyl)-5-chloropyridine (1.94 g, 8.87 mmol) (prepared essentially as described for Example 14b) in THF (30 mL) cooled in an ice bath were added triphenylphosphine pellets (2.6 g, 9.76 mmol). The mixture was stirred at room temperature for 16 h. Ammonium hydroxide solution (10 mL) was added to the mixture followed by additional stirring for 4 h. NaOH solution (3 N, 40 mL) was then added and the mixture was heated at 40° C. for 1 h. The organic layer was separated and washed with HCl solution (2 N, 60 mL). The aqueous layer was then basified with 4 N NaOH solution and extracted with EtOAc twice. The solvent was evaporated to leave a pale yellow oil (1.6 g, 93% yield). $^1$H NMR (300 Hz, CDCl$_3$) δ 8.59 (d, 1H), 7.78 (dd, 1H), 7.62 (d, 1H), 3.40 (t, 2H); LC/MS (m/z) [M+1]$^+$ 193.0 (calculated for C$_7$H$_7$ClF$_2$N$_2$, 192.0).

b. N-[2-(Amidinoaminooxy)ethyl]-2-{3-[(2,2-difluoro-2-(5-chloropyridin-2-yl)ethyl)amino]-6-cyano-2-fluorophenyl}acetamide

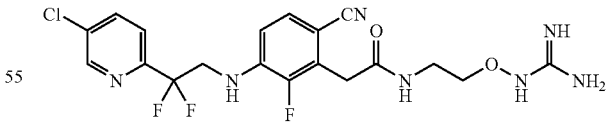

Prepared from 2,2-Difluoro-2-(5-chloro-pyridin-2-yl)-ethylamine (prepared in the previous step) essentially as described for Example 1j-1. $^1$H NMR (300 Hz, CDCl$_3$) δ 8.61 (dd, J=2.4, 0.6 Hz, 1H), 7.82 (dd, J=8.4, 2.4 Hz, 1H), 7.65 (dd, J=8.4, 0.6 Hz, 1H), 7.30 (dd, J=8.5, 1.2 Hz, 1H), 6.78 (t, J=8.3 Hz, 1H), 6.69 (m, 1H), 4.96 (m, 1H), 4.12 (m, 2H), 3.90 (t, J=4.6 Hz, 2H), 3.71 (d, J=1.8 Hz, 2H), 3.50 (m, 3H); LC/MS (m/z) [M+1]$^+$ 470.3 (calculated for C$_{19}$H$_{19}$ClF$_3$N$_7$O$_2$, 469.8).

c. N-[2-(Amidinoaminooxy)ethyl]-2-{3-[(2,2-difluoro-2-(5-chloropyridin-2-yl)ethyl)amino]-6-cyano-2-fluorophenyl}acetamide Hydrochloride

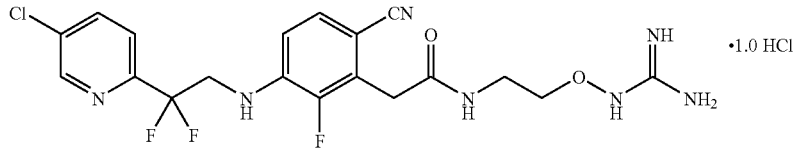

Prepared from N-[2-(Amidinoaminooxy)ethyl]-2-{3-[(2,2-difluoro-2-(5-chloropyridin-2-yl)ethyl)amino]-6-cyano-2-fluorophenyl}acetamide (prepared in the preceding step), essentially as described for Example 1m. $^1$H NMR (300 Hz, DMSO-$d_6$) δ 10.95 (s, 1H), 8.80 (d, J=2.2 Hz, 1H), 8.45 (brs, 1H), 8.15 (dd, J=8.5, 2.5 Hz, 1H), 7.72 (m, 5H), 7.40 (d, J=8.5 Hz, 1H), 6.84 (m, 2H), 4.10 (dt, J=15.0, 6.4 Hz, 2H), 3.78 (t, J=5.3 Hz, 2H), 3.62 (s, 2H), 3.35 (t, J=5.6 Hz, 2H); LC/MS (m/z) [M+1]$^+$ 470.4 (calculated for $C_9H_{19}ClF_3N_7O_2$, 469.8).

Example 16

N-[2-(Amidinoaminooxy)ethyl]-2-{3-[(2,2-difluoro-2-(5-chloro-1-oxy-pyridin-1-yl)ethyl)amino]-6-cyano-2-fluorophenyl}acetamide

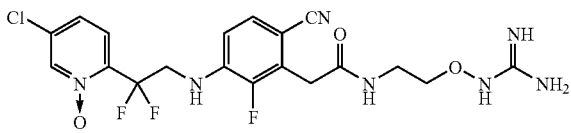

e. {6-Cyano-3-[N-trifluoroacetyl-2,2-difluoro-2-(5-chloro-pyridin-2-yl)-ethylamino]-2-fluoro-phenyl}-acetic Acid Ethyl Ester

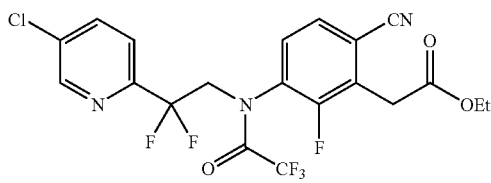

To a stirring solution of trifluoroacetic anhydride (5.05 g, 23.9 mmol, 5×) and {6-Cyano-3-[2,2-difluoro-2-(5-chloro-pyridin-2-yl)-ethylamino]-2-fluoro-phenyl}-acetic acid ethyl ester (prepared essentially as described for Example 1j) in $CH_2Cl_2$ (40 mL) was added slowly diisopropylethylamine (914 μL, 5.26 mmol). The reaction was allowed at room temperature overnight. The solvent was evaporated under high vacuum. The residue was dissolved in $CH_2Cl_2$ and washed with water twice. The organic layer was dried over $Na_2SO_4$. The product (2.37 g, 100% yield) was purified chromatographically (10-20% EtOAc/Hex). $^1$H NMR (300 Hz, CDCl$_3$) δ 8.52 (d, 1H), 7.82 (dd, 1H), 7.60 (3, 1H), 5.15 (m, 1H), 4.19 (m, 3H), 3.94 (d, 2H), 1.27 (t, 3H); LC/MS (m/z) [M+1]$^+$ 494.0 (calculated for $C_{20}H_{14}ClF_6N_3O_3$, 493.1).

b. {6-Cyano-3-[N-trifluoroacetyl-2,2-difluoro-2-(N-oxide-5-chloro-pyridin-2-yl)-ethylamino]-2-fluoro-phenyl}-acetic Acid Ethyl Ester

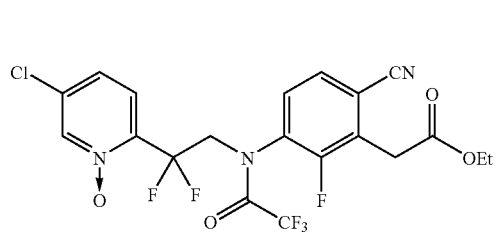

To a stirring solution of {6-Cyano-3-[N-trifluoroacetyl-2,2-difluoro-2-(5-chloro-pyridin-2-yl)-ethylamino]-2-fluoro-phenyl}-acetic acid ethyl ester (2.37 g, 4.8 mmol), prepared as the previous step, in 1,2-dichloroethane (5 mL) was added mCPBA (1.55 g, 6.24 mmol, 1.3×) and 3-t-butyl-4-hydroxy-5-methylphenyl sulfide (Kishi's radical inhibitor, 172 mg, 0.48 mmol). The mixture was heated at 55° C. for overnight. The solution was poured into a sat. NaHCO$_3$/Na$_2$S$_2$O$_3$ solution (100 mL). The organic layer was separated and the aqueous layer was backwashed with CH$_2$Cl$_2$. The combined organic layer was washed with sat. NaHCO$_3$ twice and brine once, and dried over Na$_2$SO$_4$. Purification via flash chromatography (30-50% EtOAc/Hex) afforded the product as an oil (2 g, 81% yield). $^1$H NMR (300 Hz, CDCl$_3$) δ 8.22 (s, 1H), 7.58 (m, 2H), 7.40 (m, 2H), 5.05 (m, 1H), 4.70 (m, 1H), 4.20 (q, 2H), 3.94 (d, 2H), 1.27 (t, 3H); LC/MS (m/z) [M+1]$^+$ 510.0 (calculated for $C_{20}H_{14}ClF_6N_3O_4$, 509.1).

c. {6-Cyano-3-[2,2-difluoro-2-(N-oxide-5-chloro-pyridin-2-yl)-ethylamino]-2-fluoro-phenyl}-acetic Acid

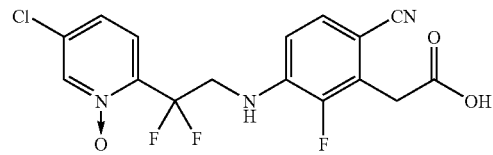

{6-Cyano-3-[N-trifluoroacetyl-2,2-difluoro-2-(N-oxide-5-chloro-pyridin-2-yl)-ethylamino]-2-fluoro-phenyl}-acetic acid ethyl ester (2 g, 3.9 mmol), as prepared in the preceding step, was dissolved in THF (10 mL) and CH$_3$OH (10 mL). To the stirring solution was added NaOH solution (1 N, 9.8 mL, 2.5×). The mixture was stirred overnight. The mixture was neutralized with 4 N HCl solution and then extracted with EtOAc. The organic layer was washed with brine and dried over Na$_2$SO$_4$. The solvent was evaporated and the white solid (1.5 g, 100% yield) was used for next step without further purification.

d. N-[2-(Amidinoaminooxy)ethyl]-2-{3-[(2,2-difluoro-2-(N-oxide-5-chloropyridyl)ethyl)amino]-6-cyano-2-fluorophenyl}acetamide

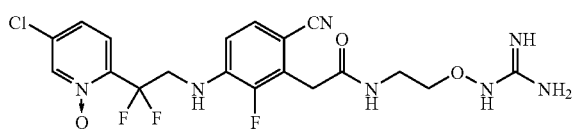

Prepared from {6-Cyano-3-[2,2-difluoro-2-(N-oxide-5-chloro-pyridin-2-yl)-ethylamino]-2-fluoro-phenyl}-acetic acid (prepared in the previous step), using essentially the same protocol as described for Example 1k-l. $^1$H NMR (300 Hz, CD$_3$OD) δ 8.56 (d, J=1.3 Hz, 1H), 7.69 (d, J=8.8 Hz, 1H), 7.58 (dd, J=8.6, 1.8 Hz, 1H), 7.28 (dd, J=8.6, 1.2 Hz, 1H), 6.98 (t, J=8.9 Hz, 1H), 4.38 (t, J=13.9 Hz, 2H), 3.79 (t, J=5.3 Hz, 2H), 3.71 (d, J=1.9 Hz, 2H), 3.42 (t, J=5.6 Hz, 2H); LC/MS (m/z) [M+1]$^+$ 486.4 (calculated for C$_{19}$H$_{19}$ClF$_3$N$_7$O$_3$, 485.1).

e. N-[2-(Amidinoaminooxy)ethyl]-2-{3-[(2,2-difluoro-2-(N-oxide-5-chloropyridyl)ethyl)amino]-6-cyano-2-fluorophenyl}acetamide Hydrochloride

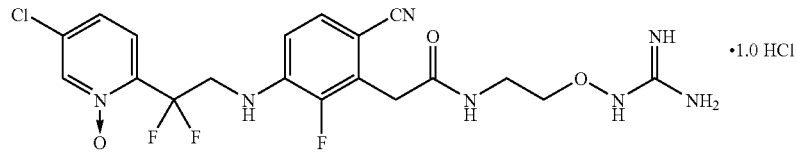

Prepared from N-[2-(Amidinoaminooxy)ethyl]-2-{3-[(2,2-difluoro-2-(N-oxide-5-chloropyridyl)ethyl)amino]-6-cyano-2-fluorophenyl}acetamide (prepared in the preceding step), essentially as described for Example 2j. $^1$H NMR (300 Hz, DMSO-d$_6$) δ 10.95 (s, 1H), 8.78 (d, J=1.8 Hz, 1H), 8.62 (t, J=5.4 Hz, 1H), 7.70 (d, J=8.7 Hz, 1H), 7.60 (dd, J=8.7, 1.8 Hz, 1H), 7.35 (m, 4H), 6.95 (m, 2H), 4.30 (dt, J=14.6, 6.8 Hz, 2H), 3.78 (t, J=5.4 Hz, 2H), 3.62 (s, 2H), 3.35 (t, 2H, buried inside water peak); LC/MS (m/z) [M+1]$^+$ 486.4 (calculated for C$_{19}$H$_{19}$ClF$_3$N$_7$O$_3$, 485.1). Elem. Anal. Calc. for free base •1.00 HCl•0.02 H$_2$O: C, 43.68; H, 3.86; N, 18.77; Cl, 13.54. Found: C, 44.07; H, 3.47; N, 18.84; Cl, 13.28.

Example 17

N-[2-(Amidinoaminooxy)ethyl]-2-{6-cyano-3-[2,2-difluoro-2-(1-oxy-pyridin-2-yl)-ethylamino]-2-fluoro-phenyl}acetamide

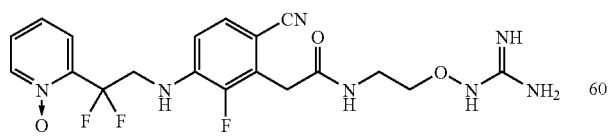

Prepared essentially as described for Examples 1a-j and 14e-h. 1H NMR (300 MHz, CD3OD) δ 8.42-8.37 (m, 1H), 7.79-7.73 (m, 1H), 7.63-7.52 (m, 2H), 7.26 (dd, J=8.6 Hz, 1.3 Hz, 1H), 6.99 (t, J=8.5 Hz, 1H), 4.43 (t, J=13.9 Hz, 2H), 3.79 (t, J=5.5 Hz, 2H), 3.70 (d, J=1.9 Hz, 2H), 3.42 (t, J=5.4 Hz, 2H). LC/MS (m/z) [M+1]$^+$ 452.4 (calculated for C$_{19}$H$_{20}$F$_3$N$_7$O$_3$, 451.2).

a. N-[2-(Amidinoaminooxy)ethyl]-2-{6-cyano-3-[2,2-difluoro-2-(1-oxy-pyridin-2-yl)-ethylamino]-2-fluoro-phenyl}acetamide Hydrochloride

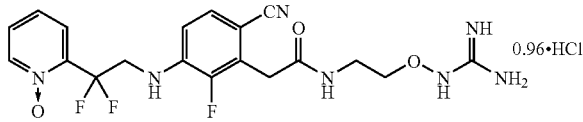

Prepared from N-[2-(Amidinoaminooxy)ethyl]-2-{6-cyano-3-[2,2-difluoro-2-(1-oxy-pyridin-2-yl)-ethylamino]-2-fluoro-phenyl}acetamide (prepared in the previous step) using essentially the protocol described for Example 2j. $^1$H NMR (300 MHz, CD$_3$OD) δ 8.42-8.38 (m, 1H), 7.79-7.75 (m, 1H), 7.64-7.54 (m, 2H), 7.29 (dd, J=8.7 Hz, 1.3 Hz, 1H), 7.03 (t, J=8.3 Hz, 1H), 4.44 (t, J=14.2 Hz, 2H), 3.94 (t, J=5.5 Hz, 2H), 3.73 (d, J=1.8 Hz, 2H), 3.51 (t, J=5.4 Hz, 2H). LC/MS (m/z) [M+1]$^+$ 452.4 (calculated for C$_{19}$H$_{20}$F$_3$N$_7$O$_3$, 451.2). Elem. Anal. Calc. for free base •0.96 HCl: C, 46.92; H, 4.34; N, 20.16; Cl, 7.00. Found: C, 47.04; H, 4.66; N, 20.26; Cl, 6.93. Karl Fischer % H$_2$O: <0.10.

Example 18

N-[2-(Amidinoaminooxy)ethyl]-2-{3-[(2,2-difluoro-2-(2-methanesulfonylphenyl)ethyl)amino]-6-cyano-2-fluorophenyl}acetamide

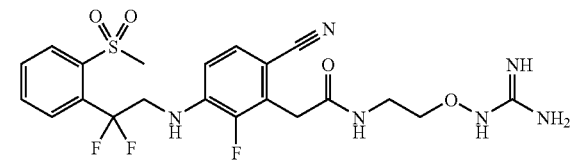

a. 1-Iodo-2-methanesulfonylbenzene

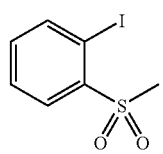

To a solution of 2-methylsulfonylaniline hydrochloride (1.71 g, 10 mmol) and conc. HCl (5 mL) in ice water (10 mL) was added dropwise an aqueous solution of sodium nitrite (11 mmol dissolved in 20 mL of H₂O), and the mixture was stirred at 0° C. for 15 min. Then an aqueous solution of KI (34 mmol dissolved in 30 mL of H₂O) was added dropwise and the mixture was stirred for 12 h at room temperature. The dark brown mixture was quenched with 2N NaOH solution until the pH became alkaline. The resulting light brown precipitate was collected by filtration, washed with H₂O and dried under vacuum to yield the desired compound (1.97 g, 70%). ¹H-NMR (300 MHz, CDCl₃) δ 8.23 (dd, J=7.9 Hz, 1.7 Hz, 1H), 8.12 (dd, J=7.9 Hz, 1.2 Hz, 1H), 7.57 (td, J=7.5 Hz, 1.2 Hz, 1H), 7.28 (td, J=7.6 Hz, 1.7 Hz, 1H), 3.26 (s, 3H).

b. Difluoro-(2-methanesulfonyl-phenyl)-acetic Acid Ethyl Ester

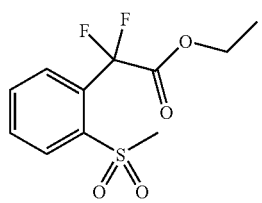

To a stirred suspension of Cu(0) (496 mg, 78 mmol) in DMSO (2.5 mL) at room temperature under nitrogen atmosphere was added ethylbromodifluoroacetate (0.5 mL, 39 mmol). The reaction mixture was stirred at 35° C. for 30 min. Then the solution was brought to room temperature and 1-iodo-2-methanesulfonylbenzene (1.0 g, 35 mmol), as prepared in the preceding step, was added. The reaction mixture was stirred at 35° C. for 12 h. The reaction mixture was cooled to room temperature and passed through a bed of Celite using EtOAc to rinse. The filtrate was washed with saturated NH₄Cl (50 mL) until the blue color dissipated. The organic phase was then washed with brine (50 mL), dried over Na₂SO₄ and concentrated in vacuo to afford 772 mg crude product. The residue was purified by flash column chromatography (20-40% ethyl acetate in hexanes) to yield the desired compound (264 mg, 27%). ¹H-NMR (300 MHz, CDCl₃) δ 8.18 (d, J=7.6 Hz, 1H), 7.94 (dd, J=7.7 Hz, 1.7 Hz, 1H), 7.76 (pd, J=7.6 Hz, 1.5 Hz, 2H), 4.31 (q, J=7.2 Hz, 2H), 3.15 (s, 3H), 1.29 (t, J=7.1 Hz, 3H). LC/MS (m/z) [M+1]⁺ 279.3 (calculated for C₁₁H₁₃F₂O₄S, 279.3).

c. N-[2-(Amidinoaminooxy)ethyl]-2-{3-[(2,2-difluoro-2-(2-methanesulfonylphenyl) ethyl)amino]-6-cyano-2-fluorophenyl}acetamide

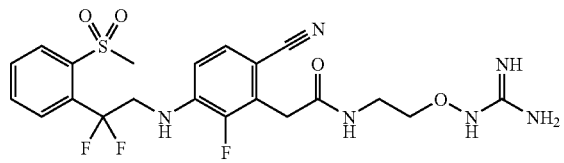

A solution of 3:1 CH₂Cl₂/TFA (0.8 mL) was added to N-[2-(N',N''-bis(tert-butoxycarbonyl)amidinoaminooxy) ethyl]-2-{3-[(2,2-difluoro-2-(2 methanesulfonylphenyl) ethyl)amino]-6-cyano-2-fluorophenyl}acetamide (34.8 mg, 0.049 mmol)(prepared essentially as described in Example 2h), and the reaction mixture was stirred at room temperature for 3 h. After evaporating the solvents, the residue was subjected to flash chromatography (DCM/MeOH saturated with gaseous NH₃; 95:5→90:10) to yield 18.4 mg (74%) of the title compound as a white solid. ¹H NMR (300 MHz, CD₃OD) δ 8.24 (m, 1H), 7.74 (m, 3H), 7.20 (dd, J=8.6 Hz, 1.3 Hz, 1H), 6.87 (t, J=8.7 Hz, 1H), 4.24 (t, J=14.2 Hz, 2H), 3.80 (t, J=5.2 Hz, 2H), 3.72 (d, J=1.9 Hz, 2H), 3.43 (t, J=5.5 Hz, 2H), 3.27 (s, 3H). LC/MS (m/z) [M+1]⁺ 513.4 (calculated for C₂₁H₂₄F₃N₆O₄S, 513.5).

d. N-[2-(Amidinoaminooxy)ethyl]-2-{3-[(2,2-difluoro-2-(2-methanesulfonylphenyl) ethyl)amino]-6-cyano-2-fluorophenyl}acetamide Hydrochloride

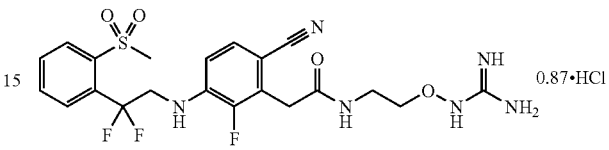

Prepared from N-[2-(Amidinoaminooxy)ethyl]-2-{3-[(2,2-difluoro-2-(2-methanesulfonylphenyl) ethyl)amino]-6-cyano-2-fluorophenyl}acetamide (prepared in the preceding step) using essentially the protocol described for Example 2j. ¹H NMR (300 MHz, CD₃OD) δ 8.27 (m, 1H), 7.74 (m, 3H), 7.22 (d, J=8.7 Hz, 1H), 6.90 (t, J=8.4 Hz, 1H), 4.24 (td, J=14.2 Hz, 4.7 Hz, 2H), 3.94 (t, J=5.5 Hz, 2H), 3.74 (d, J=1.6 Hz, 2H), 3.51 (t, J=5.4 Hz, 2H), 3.27 (s, 3H). LC/MS (m/z) [M+1]⁺ 513.4 (calculated for C₂₁H₂₄F₃N₆O₄S, 513.5). Elem. Anal. Calc. for free base •0.87 HCl•0.03 H₂O: C, 46.31; H, 4.43; N, 15.43; Cl, 5.64. Found: C, 46.15; H, 4.14; N, 15.28; Cl, 5.63. Karl Fischer % water: 0.11.

Example 19

N-[2-(Amidino-N-methyl-aminooxy)ethyl]-2-{3-[(2,2-difluoro-2-pyridyl-ethyl)amino]-6-cyano-2-fluorophenyl}acetamide

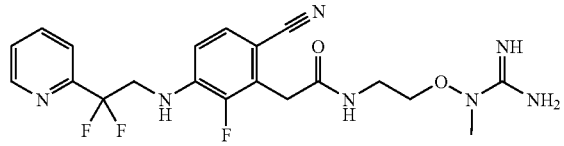

a. N-Hydroxy-N-methyl-carbamic Acid Methyl Ester

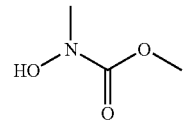

To an ice-cold stirred mixture of N-methylhydroxylamine hydrochloride (5.38 g, 64.4 mmol) and TEA (9.4 mL, 68 mmol) in DCM (35 mL) was added methyl chloroformate (5.2 mL, 67 mmol) in one portion via syringe. After 5 min stirring at 0° C., additional TEA (9.4 mL, 68 mmol) was added rapidly dropwise with stirring at 0° C. The ice-bath was then removed, and the white slurry was shaken for 4 h at rt. It was then partitioned with ice water (100 mL) and ether (50 mL), and the aq layer was extracted with ether (1×50 mL). The aqueous layer was saturated with solid NaCl and then extracted with EtOAc (5×50 mL). The combined organic layers were dried (Na₂SO₄) and concentrated to afford 5.91 g of the title compound (56.3 mmol, 87%) as a pale yellow oil contaminated (~8 mol %) with N-methoxycarbonyloxy-N-methylcarbamic acid methyl ester. 1H NMR (300 Hz, CDCl$_3$) δ 3.78 (s, 3H), 3.22 (s, 3H). LC/MS (m/z) [MH$^+$] 106 (calculated for C$_3$H$_8$NO$_3$, 106.1).

b. [2-(N-Methyl-N-methoxycarbonyl-aminooxy)-ethyl]-carbamic Acid tert-butyl Ester

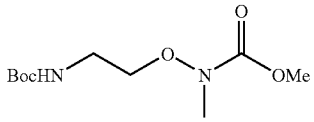

To a solution of N-Hydroxy-N-methyl-carbamic acid methyl ester (5.90 g, 56.2 mmol), as prepared in the previous step, in DMF (130 mL) at 0° C. was added NaH (1.35 g, 53 mmol) in one portion. The mixture was stirred at room temperature for 15 min, then stirred on an ice bath while a solution of methanesulfonic acid 2-tert-butoxycarbonylamino-ethyl ester (10.38 g, 43 mmol) (Clagett-Dame, M., et al; Biochim. Biophys. Acta, 986:271-280, 1989) in DMF (50 mL) was added in one portion. The ice bath was removed and the mixture stirred at room temperature 23 h. The DMF was removed by rotary evaporation, the residue was diluted with half-saturated NaHCO$_3$ (100 mL), and extracted with EtOAc (3×50 mL). The organic layers were combined, dried (Na$_2$SO$_4$), and concentrated. Flash chromatographic purification of the residue (3:2 hex/EtOAc) afforded 643 mg of the title compound as a colorless oil (2.59 mmol, 6% yield). 1H NMR (300 Hz, CDCl$_3$) δ 5.38 (br s, 1H), 3.89 (t, J=5.1 Hz, 2H), 3.78 (s, 3H), 3.34 (q, J=5.5 Hz, 2H), 3.14 (s, 3H), 1.45 (s, 9H); LC/MS (m/z) [MH$^+$–Boc] 149 (calculated for C$_5$H$_{13}$N$_2$O$_3$, 149.1).

c. 2-(tert-butoxycarbonylamino)ethoxy-N-methylamine

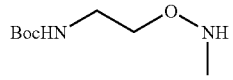

A mixture of [2-(N-Methyl-N-methoxycarbonyl-aminooxy)-ethyl]-carbamic acid tert-butyl ester (630 mg, 2.54 mmol), as prepared in the previous step, KOH (439 mg, 6.65 mmol, 15% water), D$_2$O (2.0 mL) was stirred at 90° C. for 18 h. The mixture was allowed to cool to room temperature (a bilayer formed), and extracted with DCM (2×10 mL). The organic layers were combined, dried (2×Na$_2$SO$_4$), and concentrated to give 408 mg of the title compound (contaminated with 10 mol % starting material) as a nearly colorless oil (2.15 mmol, 85% yield). 1H NMR (300 Hz, CDCl$_3$) δ 3.72 (t, J=4.9 Hz, 2H), 3.33 (br t, J=4.7 Hz, 2H), 2.70 (s, 3H), 1.45 (s, 9H).

d. [N,N'-Di(tert-butoxycarbonylamino)]-2-(tert-butoxycarbonylamino-ethoxy)-N-methylamino Guanidine

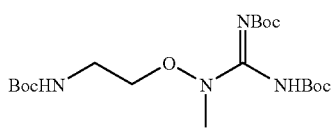

To a solution of 2-(tert-butoxycarbonylamino)ethoxy-N-methylamine (500 mg, 2.63 mmol), as prepared in the preceding step, in N,N-dimethylformamide (1 mL) was added [N,N'-di(tert-butoxycarbonyl)]amidinopyrazole (979 mg, 3.16 mmol) and the mixture was stirred at 50° C. overnight. The reaction mixture was cooled to ambient temperature, poured into water (10 mL) and extracted with methylene chloride (2×20 mL). The combined organic phases were washed with brine (10 mL), dried over Na2SO4 and concentrated in vacuo to afford 1.48 g of crude product. The residue was purified by flash column chromatography (20-40% ethyl acetate in hexanes) to yield the desired compound (723 mg, 63%). 1H-NMR (300 MHz, CDCl$_3$) δ 7.67 (br s, 1H), 5.50 (br s, 1H), 3.95 (t, J=4.8 Hz, 2H), 3.35 (q, J=5.0 Hz, 2H), 3.25 (s, 3H), 1.49 (s, 18H), 1.44 (s, 9H). LC/MS (m/z) [M+1]+ 433.3 (calculated for C19H37N4O7, 433.5).

e. 2-Aminoethoxy-N-methylamino Guanidine

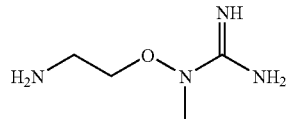

To the [N,N'-Di(tert-butoxycarbonylamino)]-2-(tert-butoxycarbonylamino-ethoxy)-N-methylamino guanidine (723 mg, 1.67 mmol), as prepared in the preceding step, was added conc. HCl, and the reaction mixture was stirred for 30 min. at room temperature. The solvent was evaporated under high vacuum to afford the desired product in quantitative yield. $^1$H-NMR (300 MHz, D$_2$O) δ 4.09 (t, J=5.0 Hz, 2H), 3.16-3.21 (s on top of t, J=5.0 Hz, 5H).

f. [6-Cyano-3-(2,2-difluoro-2-pyridin-2-yl-ethylamino)-2-fluoro-phenyl]-acetic Acid Pentafluorophenyl Ester

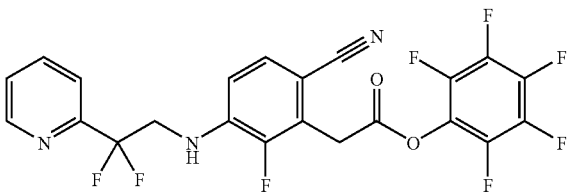

To a solution of the lithium salt of [6-cyano-3-(2,2-difluoro-2-pyridin-2-yl-ethylamino)-2-fluoro-phenyl]-acetic acid (75 mg, 0.22 mmol), prepared essentially as described in Example 1k, in N,N-dimethylformamide (0.250 mL) and methylene chloride (0.750 mL) was added pentafluorophenol (121 mg, 0.66 mmol), pyridine hydrochloride (52 mg, 0.45 mmol), dimethylaminopyridine (14 mg, 0.11 mmol), and finally diisopropylcarbodiimide (0.038 mL, 0.24 mmol). The mixture was stirred at room temperature for 24 h. The solvents were evaporated under high vacuum and the residue was purified by flash column chromatography (20-30% ethyl acetate in hexanes) to yield the desired compound (51 mg, 50%). $^1$H-NMR (300 MHz, CDCl$_3$) δ 8.68 (d, J=5.5 Hz, 1H), 7.84 (td, J=7.8 Hz, 1.7 Hz, 1H), 7.69 (dt, J=7.9 Hz, 1.1 Hz, 1H), 7.40-7.45 (m, 1H), 7.35 (dd, J=8.6 Hz, 1.3 Hz, 1H), 6.86 (t, J=8.5 Hz, 1H), 5.05 (br s, 1H), 4.12-4.23 (m, 4H). LC/MS (m/z) [M+1]$^+$ 502.3 (calculated for C$_{22}$H$_{12}$F$_8$N$_3$O$_2$, 502.3).

g. N-[2-(Amidino-N-methyl-aminooxy)ethyl]-2-{3-[(2,2-difluoro-2-pyridyl-ethyl)amino]-6-cyano-2-fluorophenyl}acetamide

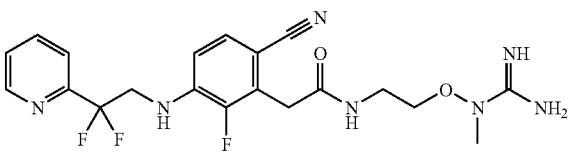

To a solution of [6-Cyano-3-(2,2-difluoro-2-pyridin-2-yl-ethylamino)-2-fluoro-phenyl]-acetic acid pentafluorophenyl ester (50 mg, 0.11 mmol), as prepared in the preceding step, in N,N-dimethylformamide (1 mL) was added 2-aminoethoxy-N-methylamino guanidine (prepared as described for Example 19e) and diisopropylethylamine (0.075 mL, 0.43 mmol) and the mixture was stirred for 12 h at room temperature. The solvents were evaporated under high vacuum and the residue was purified by flash column chromatography (inactivated with NH$_3$, 10% MeOH/CH$_2$Cl$_2$) to yield the desired compound (36 mg, 75%). $^1$H-NMR (300 MHz, CD$_3$OD) δ 8.66 (d, J=5.6 Hz, 1H), 7.94 (td, J=7.7 Hz, 1.7 Hz, 1H), 7.71 (dt, J=7.9 Hz, 1.0 Hz, 1H), 7.49-7.54 (m, 1H), 7.29 (dd, J=9.8 Hz, 1.2 Hz, 1H), 6.85 (t, J=8.5 Hz, 1H), 4.12 (t, J=14.0 Hz, 2H), 4.03 (t, J=5.2 Hz, 2H), 3.76 (d, J=1.78 Hz, 2H), 3.51 (t, J=5.2 Hz, 2H), 3.31 (s, 3H). LC/MS (m/z) [M+1]$^+$ 450.4 (calculated for C$_{20}$H$_{23}$F$_3$N$_7$O$_2$, 450.4).

Example 20

2-[6-Cyano-3-(2,2-difluoro-2-pyridin-2-yl-ethylamino)-2-fluorophenyl]-N-tetrazolo[1,5-b]pyridazin-6-ylmethyl-acetamide

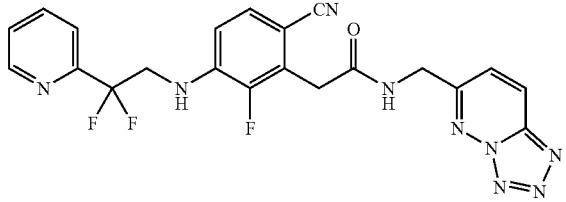

a. Tetrazolo[1,5-b]pyridazine-6-carbonitrile

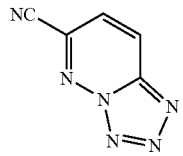

A mixture of 6-chloropyridazine-3-carbonitrile (291 mg, 2.12 mmol) (Szilagyi, G., et al; *European J. Med. Chem.* 19:111-117, 1984), sodium azide (149 mg, 2.29 mmol), and DMSO (0.9 mL) was stirred at rt for 20 min, then diluted with water (10 mL), and extracted with EtOAc (3×10 mL). The organic layers were combined, washed with brine (1×10 mL), dried (Na$_2$SO$_4$), and the clear pink solution was passed through a silica plug (EtOAc eluent). Treatment with decolorizing charcoal, filtration, and concentration with rotary evaporation afforded the title compound as an off-white solid (243 mg, 1.69 mmol, 80% yield). $^1$H-NMR (300 MHz, CDCl$_3$) δ 8.66 (d, J=9.3 Hz, 1H), 7.81 (d, J=9.3 Hz, 1H).

b. C-Tetrazolo[1,5-b]pyridazin-6-yl-methylamine

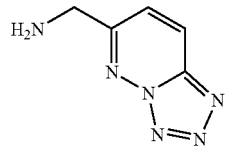

Tetrazolo[1,5-b]pyridazine-6-carbonitrile (228 mg, 1.58 mmol), as prepared in the previous step, was added to a mixture of 10% Pd/C (118 mg), MeOH (8.5 mL), and 12 N HCl (0.54 mL), and was then shaken in a Parr hydrogenation apparatus at 40 psig for 5 h. The mixture was then filtered through Celite, the filter cake was washed with MeOH (2×5 mL), and concentrated to afford 255 mg of the hydrochloride salt of the title compound as an off-white solid (1.29 mmol, 82% yield, assuming dihydrochloride salt). A portion of the salt was neutralized with saturated Na2CO3 and extracted with EtOAc. The organic layer was dried (Na2SO4) and concentrated to afford the title compound (free base). $^1$H-NMR (300 MHz, CDCl$_3$) δ 8.36 (d, 9.3 Hz, 1H), 7.65 (d, 9.3 Hz, 1H), 4.27 (s, 2H), 1.62 (br s, overlapped with water peak). LC/MS (m/z) [M+1]$^+$ 151.0 (calculated for C$_5$H$_6$N$_6$, 150.1).

c. 2-[6-Cyano-3-(2,2-difluoro-2-pyridin-2-yl-ethylamino)-2-fluoro-phenyl]-N-tetrazolo[1,5-b]pyridazin-6-ylmethyl-acetamide

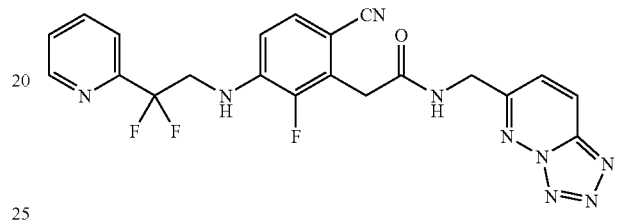

Prepared essentially as described in Example 1k, using C-Tetrazolo[1,5-b]pyridazin-6-yl-methylamine (prepared in the previous step) as the amine coupling partner. $^1$H-NMR (300 MHz, CD$_3$OD) δ 8.68-8.64 (m, 1H), 8.53 (d, J=9.4 Hz, 1H), 7.93 (dt, J=7.9 Hz, 1.7 Hz, 1H), 7.74 (d, J=9.4 Hz, 1H), 7.70 (dt, J=7.9 Hz, 1.1 Hz, 1H), 7.54-7.48 (m, 1H), 7.29 (dd, J=8.7 Hz, 1.3 Hz, 1H), 6.85 (t, J=8.5 Hz, 1H), 4.74 (s, 2H), 4.19-4.06 (m, 2H, obscured by EtOAc solvent peak), 3.85 (d, J=1.9 Hz, 2H). LC/MS (m/z) [M+1]$^+$ 468.3 (calculated for C$_{21}$H$_{16}$F$_3$N$_9$O, 467.1).

Example 21

Tablet Preparation

Tablets containing 25.0, 50.0, and 100.0 mg, respectively, of the following active compounds are prepared as illustrated below:

a. N-[2-(Amidinoaminooxy)ethyl]-2-{3-[(2,2-difluoro-2-(quinolinyl)ethyl)amino]-6-cyano-2-fluorophenyl}acetamide;

b. N-(6-Amino-2-methyl-pyridin-3-ylmethyl)-2-[6-cyano-3-(2,2-difluoro-2-pyridin-2-yl-ethylamino)-2-fluoro-phenyl]-acetamide; and c. N-[2-(Amidinoaminooxy)ethyl]-2-{3-[(2,2-difluoro-2-pyridylethyl)amino]-6-cyano-2-fluorophenyl}acetamide.

| TABLET FOR DOSES CONTAINING FROM 25-100 MG OF THE ACTIVE COMPOUND | | | |
|---|---|---|---|
| | Amount-mg | | |
| Active Compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

Example 22

Intravenous Solution Preparation

An intravenous dosage form of the above-indicated active compounds of Examples 1 and 2 is prepared as follows:

| Active Compound | 0.5-10.0 mg |
|---|---|
| Sodium Citrate | 5-50 mg |
| Citric Acid | 1-15 mg |
| Sodium Chloride | 1-8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Example 23

In Vitro Inhibition of Purified Enzymes

Reagents: All buffer salts were obtained from Sigma Chemical Company (St. Louis, Mo.), and were of the highest purity available. The enzyme substrate, S-2765 (Z-D-Arg-Gly-Arg-p-nitroanilide) was obtained from DiaPharma (West Chester, Ohio). N-succinyl-Ala-Ala-Pro-Arg-p-nitroanilide (BACHEM L-1720) was obtained from BACHEM (King of Prussia, Pa.). N-p-Tosyl-Gly-Pro-Lys-p-nitroanilide (Sigma T6140), N-succinyl-Ala-Ala-Pro-Phe-p-nitroanilide (Sigma S7388), N-CBZ-Val-Gly-Arg-p-nitroanilide (Sigma C7271) is obtained from Sigma and N-succinyl-Ala-Ala-Pro-Val-p-nitroanilide (BACHEM L-1770) is obtained from BACHEM (King of Prussia, Pa.).

Human α-thrombin and human factor Xa were obtained from Enzyme Research Laboratories (South Bend, Ind.). Human trypsin was obtained from Calbiochem (La Jolla, Calif.). Human plasmin is obtained from Enzyme Research Laboratories (South Bend, Ind.). Bovine α-chymotrypsin (Sigma C4129) and human kidney cell urokinase (Sigma U5004) are obtained from Sigma. Human leukocyte elastase is obtained from Elastin Products (Pacific, Mo.).

$K_i$ Determinations: All assays are based on the ability of the test compound to inhibit the enzyme-catalyzed hydrolysis of a peptide p-nitroanilide substrate. In a typical $K_i$ determination, substrate is prepared in DMSO, and diluted into an assay buffer consisting of 50 mM HEPES, pH 7.5, 200 mM NaCl, 0.05% n-octyl β-d-glucopyranoside. The final concentrations for each of the substrates is listed below. In general, substrate concentrations are lower than the experimentally determined value for $K_m$. Test compounds are prepared as 10 mM solutions in DMSO. Dilutions are prepared in DMSO yielding 7 final concentrations encompassing a 200-fold concentration range. Enzyme solutions are prepared at the concentrations listed below in assay buffer.

In a typical $K_i$ determination, into each well of a 96 well plate is pipetted 280 μL of substrate solution, 10 μL of test compound solution, and the plate allowed to thermally equilibrate at 37° C. in a Molecular Devices plate reader for 15 minutes. Reactions were initiated by the addition of a 10 μL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined apparent $K_i$ value (Ki app). The Ki is calculated from the Ki app using the Ki factor specific for the assay, where Ki=Ki app×Ki factor, or Ki=Ki app×(1/(1+[S]/Km)).

Thrombin: Thrombin activity was assessed as the ability to hydrolyze the substrate N-succinyl-Ala-Ala-Pro-Arg-p-nitroanilide (Km=320 μM, Ki factor=0.76). Substrate solutions were prepared at a concentration of 107 μM in assay buffer. Final DMSO concentration was 4.3%. Purified human α-thrombin was diluted into assay buffer to a concentration of 33 nM. Final reagent concentrations were: [thrombin]=1.1 nM, [substrate N-succinyl-Ala-Ala-Pro-Arg-p-nitroanilide]=100 μM.

Factor X [FXa]: FXa activity was assessed as the ability to hydrolyze the substrate S-2765 (Z-D-Arg-Gly-Arg-p-nitroanilide, Km=260 μM, Ki factor=0.72). Substrate solutions were prepared at a concentration of 107 μM in assay buffer. Final DMSO concentration was 3.3%. Purified activated human Factor X was diluted into assay buffer to a concentration of 16 nM. Final reagent concentrations were: [FXa]=0.53 nM, [S-2765]=100 μM.

Plasmin: Plasmin activity is assessed as the ability to hydrolyze the N-p-Tosyl-Gly-Pro-Lys-p-nitroanilide. Substrate solutions are prepared at a concentration of 37 μM (37 μM<<$K_m$=243 μM) in assay buffer. Final DMSO concentration is 4.3%. Purified human plasmin is diluted into assay buffer to a concentration of 240 nM. Final reagent concentrations are: [Plasmin]=8 nM, [N-p-Tosyl-Gly-Pro-Lys-p-nitroanilide]=37 μM.

Chymotrypsin: Chymotrypsin activity is assessed as the ability to hydrolyze N-succinyl-Ala-Ala-Pro-Phe-p-nitroanilide. Substrate solutions are prepared at a concentration of 14 μM (14 μM<<$K_m$=62 μM) in assay buffer. Final DMSO concentration is 4.3%. Purified bovine chymotrypsin is diluted into assay buffer to a concentration of 81 nM. Final reagent concentrations are: [Chymotrypsin]=2.7 nM, [N-succinyl-Ala-Ala-Pro-Phe-p-nitroanilide]=14 μM.

Trypsin: Trypsin activity was assessed as the ability to hydrolyze the substrate S-2765 (Z-D-Arg-Gly-Arg-p-nitroanilide, Km=61 μM, Ki factor=0.50). Substrate solutions were prepared at a concentration of 64 μM in assay buffer. Final DMSO concentration was 3.3%. Purified human trypsin was diluted into assay buffer to a concentration of 10 nM. Final reagent concentrations were: [Trypsin]=0.33 nM, [S-2765]=60 μM.

Elastase: Elastase activity is assessed as the ability to hydrolyze N-succinyl-Ala-Ala-Pro-Val-p-nitroanilide. Substrate solutions are prepared at a concentration of 19 μM (19 μM<<$K_m$=89 μM) in assay buffer. Final DMSO concentration is 4.3%. Purified human leukocyte elastase is diluted into assay buffer to a concentration of 750 nM. Final reagent concentrations are: [Elastase]=25 nM, [N-succinyl-Ala-Ala-Pro-Val-p-nitroanilide]=19 μM.

Urokinase: Urokinase activity is assessed as the ability to hydrolyze N-CBZ-Val-Gly-Arg-p-nitroanilide. Substrate solutions are prepared at a concentration of 100 μM (100 μM<$K_m$=1.2 μM) in assay buffer. Final DMSO concentration is 4.3%. Purified human kidney urokinase is diluted into assay buffer to a concentration of 1.2 μM. Final reagent concentrations are: [Urokinase]=40 nM, and [N-CBZ-Val-Gly-Arg-p-nitroanilide]=100 μM.

The results indicate that the compounds of Examples 1 through 20 have Ki values for human thrombin of between 0.0003 to 1.3 μM. The compound of Example 10 has a Ki of 0.0011 μM.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:
1. A compound of Formula I:

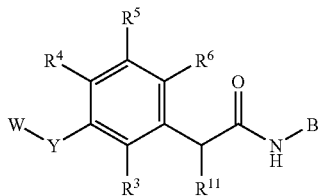

or a pharmaceutically acceptable salt thereof; wherein:

W is $R^1$ or $R^1S(O_2)$:

$R^1$ is $R^2$, $R^2(CH_2)_tC(R^{12})_2$, where t is 0-3, and each $R^{12}$ can be the same or different, $(R^2)(OR^{12})CH(CH_2)_p$, where p is 1-4, $(R^2)_2(OR^{12})C(CH_2)_p$, where p is 1-4, $R^2C(R^{12})_2(CH_2)_t$, wherein t is 0-3, and each $R^{12}$ can be the same or different, wherein $(R^{12})_2$ can also form a ring with C represented by $C_{3-9}$ cycloalkyl, $R^2CF_2(R^{12})_2(CH_2)_q$, wherein q is 0-2, and each $R^{12}$ can be the same or different, wherein $(R^{12})_2$ can also form a ring with C represented by $C_{3-9}$ cycloalkyl, $R^2CH_2C(R^{12})_2(CH_2)_q$, wherein q is 0-2, and each $R^{12}$ can be the same or different, wherein $(R^{12})_2$ can also form a ring with C represented by $C_{3-9}$ cycloalkyl, $(R^2)_2CH(CH_2)_r$, where r is 0-4 and each $R^2$ can be the same or different, and wherein $(R^2)_2$ can also form a ring with CH represented by $C_{3-9}$ cycloalkyl, $C_{7-12}$ bicyclic alkyl, $C_{10-16}$ tricyclic alkyl, or a 6-membered monocyclic heterocyclic ring which is unsaturated, and which has one heteroatom that is N;

$R^2O(CH_2)_p$, wherein p is 2-4, $(R^2)_2CF(CH_2)_r$, wherein r is 0-4 and each $R^2$ can be the same or different, wherein $(R^2)_2$ can also form a ring with C represented by $C_{3-9}$ cycloalkyl, $C_{7-12}$ bicyclic alkyl, $C_{10-16}$ tricyclic alkyl, or a 6-membered monocyclic-heterocyclic ring which is unsaturated, and which has one heteroatom that is selected from the group consisting of N, O, and S;

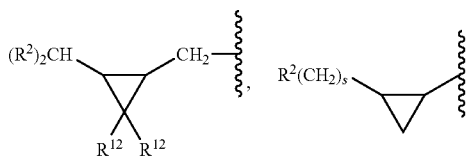

where s is 0 or 1, or
$R^2CF_2C(R^{12})_2$;

$R^2$ is phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, $CO_2R^{21}$, $CONH_2$, $CONR^{22}R^{23}$, $SO_2$ alkyl, $SO_2NH_2$, or $SO_2NR^{22}R^{23}$, a 6-membered monocyclic heteroaryl ring, wherein the heteroaryl ring has one heteroatom that is N and wherein the heteroaryl ring is unsubstituted or substituted with one or more of $C_{1-4}$ alkyl, $C_{1-4}$ alkoxy, halogen, hydroxy, $CF_3$, $OCF_3$, COOH, $CO_2R^{21}$, $CONH_2$, $CONR^{22}R^{23}$, $SO_2$ alkyl, $SO_2NH_2$, or $SO_2NR^{22}R^{23}$, $C_{3-9}$ cycloalkyl, which is unsubstituted or substituted with one or more of $C_{1-4}$ alkyl, $C_{1-4}$ alkoxy, halogen, hydroxy, $CF_3$, $OCF_3$, COOH, $CO_2R^{21}$, $CONH_2$, $CONR^{22}R^{23}$, $SO_2$alkyl, $SO_2NH_2$, or $SO_2NR^{22}R^{23}$, or $C_{7-12}$ bicyclic alkyl, which is unsubstituted or substituted with one or more of $C_{1-4}$ alkyl, $C_{1-4}$ alkoxy, halogen, hydroxy, $CF_3$, $OCF_3$, COOH, $CO_2R^{21}$, $CONH_2$, $CONR^{22}R^{23}$, $SO_2$alkyl, $SO_2NH_2$, or $SO_2NR^{22}R^{23}$;

Y is —NH— or O;

$R^3$ is hydrogen, halogen or OH;

$R^4$ and $R^5$ are independently hydrogen, halogen, alkyl, alkenyl, alkynyl, hydroxy, alkoxy, haloalkyl, haloalkoxy, hydroxyalkyl, cyano, nitro, —$CO_2R^x$, —$CH_2OR^x$ or —$OR^x$, where $R^x$, in each instance, is independently one of hydrogen or $C_{1-6}$ alkyl;

$R^6$ is cyano or acetylenyl;

$R^{11}$ is hydrogen, halogen or alkyl;

$R^{12}$ is hydrogen or halogen, $C_{1-6}$ alkyl, unsubstituted or substituted with one or more of hydroxy, COOH, amino, or halogen, $CF_3$;

$R^{21}$ is $C_{1-8}$ alkyl, $C_{1-8}$ cycloalkyl, $C_{1-8}$ alkyl ether, or $C_{1-8}$ cycloalkyl ether;

$R^{22}$ and $R^{23}$ are, independently, hydrogen, $C_{1-8}$ alkyl, $C_{1-8}$ cycloalkyl, $C_{1-8}$ alkyl ether, or $C_{1-8}$ cycloalkyl ether or taken together with the nitrogen atom to which they are attached, $R_{22}$ and $R_{23}$ form a 3 to 9 member saturated ring, optionally having from 0 to 2 additional heteroatoms selected from nitrogen or oxygen;

B is selected from the group consisting of:

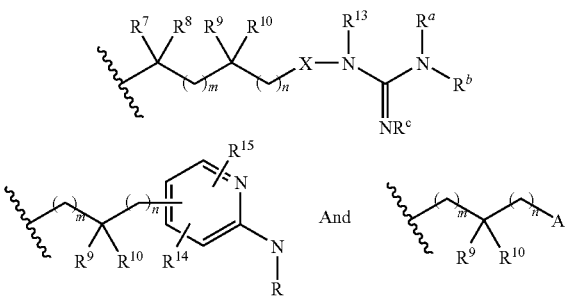

wherein $R^7$, $R^8$, $R^9$, and $R^{10}$ are independently hydrogen or alkyl;

X is —O—, —$NR^{18}$—, or —CH=N— (where N is bonded to $NR^{13}$) where $R^{18}$ is hydrogen or alkyl, wherein said alkyl is optionally substituted with amino, monoalkylamino, dialkylamino, alkoxy, hydroxy, carboxy, alkoxycarbonyl, aryloxycarbonyl, aralkoxycarbonyl, acylamino, cyano or trifluoromethyl;

$R^a$, $R^b$ and $R^c$ are independently hydrogen, alkyl, hydroxy, alkoxy, alkoxycarbonyloxy, cyano or —$CO_2R^w$,
where $R^w$ is $C_{1-12}$ alkyl, $C_{3-9}$ cycloalkyl, $C_{6-14}$ aryl, $C_{6-14}ar(C_{1-12})$ alkyl,
or

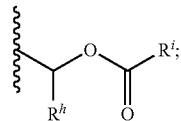

where $R^e$ and $R^f$ are independently hydrogen, $C_{1-6}$ alkyl, $C_{2-6}$ alkenyl or $C_{6-14}$ aryl, $R^g$ is hydrogen, $C_{1-6}$ alkyl, $C_{2-6}$ alkenyl or $C_{6-14}$ aryl, $R^h$ is hydrogen, $C_{1-6}$ alkyl, $C_{2-6}$ alkenyl or $C_{6-14}$ aryl, and $R^i$ is $C_{6-14}ar(C_{1-12})$ alkyl or $C_{1-12}$ alkyl;

n is from zero to 2;
m is from zero to 2;
$R^{13}$ is hydrogen or alkyl;
$R^{14}$ and $R^{15}$ are independently hydrogen, alkyl, cycloalkyl, halogen or alkoxy;
$R^{16}$ and $R^{17}$ are independently hydrogen, alkyl, hydroxy, alkoxy, cyano or —$CO_2R^j$, where $R^j$ is $C_{1-12}$ alkyl, $C_{3-9}$ cycloalkyl, $C_{6-14}$ aryl, $C_{6-14}ar(C_{1-12})$alkyl, or halo($C_{1-12}$)alkyl,
where $R^e$, $R^f$ and $R^g$ are independently hydrogen or $C_{1-12}$ alkyl; and
A is a 6-membered heteroaryl ring
wherein the heteroaryl ring has one heteroatom that is N, and is monosubstituted with —$NR^{19}R^{20}$, where $R^{19}$ and $R^{20}$ are independently hydrogen or $C_{1-4}$ alkyl,
or wherein the heteroaryl ring has one heteroatom that is N, and is optionally substituted with one or more of halogen, hydroxy, alkyl, alkoxy, or —$NR^{19}R^{20}$, where $R^{19}$ and $R^{20}$ are independently hydrogen or $C_{1-4}$ alkyl.

2. A compound of claim 1, wherein $R^2$ is
phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, $CONH_2$, or $SO_2NH_2$,
a 6-membered monocyclic heteroaryl ring, wherein the heteroaryl ring has one heteroatom that is N, and is optionally substituted with halogen, hydroxy, or alkyl,
$C_{3-9}$ cycloalkyl which can be saturated or unsaturated, or
$C_{7-12}$ bicyclic alkyl which can be saturated or unsaturated.

3. A compound of claim 1, wherein $R^3$ is hydrogen or halogen and $R^{11}$ is hydrogen or alkyl.

4. A compound of claim 1, wherein
$R^3$ is halogen;
$R^4$ and $R^5$ are independently hydrogen, halogen, or $C_{1-6}$ alkyl;
$R^{11}$ is hydrogen or $C_{1-6}$ alkyl;
$R^7$, $R^8$, $R^9$ and $R^{10}$ are independently hydrogen or $C_{1-6}$ alkyl;
$R^{18}$ is hydrogen or $C_{1-6}$ alkyl optionally substituted with amino, mono($C_{1-6}$)alkylamino, di($C_{1-6}$)alkylamino, $C_{1-8}$ alkoxy, hydroxy, carboxy, $C_{1-8}$alkoxycarbonyl, $C_{6-14}$ aryloxycarbonyl, $C_{6-14}ar(C_{1-20})$alkoxycarbonyl, acylamino, cyano or trifluoromethyl;
$R^a$, $R^b$ and $R^c$ are independently hydrogen or $C_{1-6}$ alkyl;
$R^{13}$ is hydrogen or $C_{1-6}$ alkyl;
$R^{14}$ and $R^{15}$ are independently hydrogen or $C_{1-6}$ alkyl; and
$R^{16}$ and $R^{17}$ are independently hydrogen or $C_{1-6}$ alkyl.

5. A compound according to claim 1, wherein B is

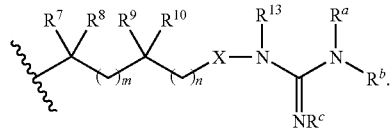

6. A compound according to claim 5, wherein X is O.

7. A compound according to claim 1, wherein B is

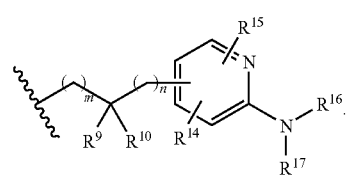

8. A compound according to claim 7, wherein $R^{16}$ and $R^{17}$ are hydrogen.

9. A compound according to claim 1, wherein B is

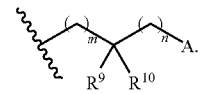

10. A compound according to claim 1, wherein:
W is $R^1$;
$R^1$ is $R^2CF_2C(R^{12})_2(CH_2)_q$;
$R^2$ is aryl or pyridyl, each of which is optionally substituted with halogen or alkyl;
$R^{12}$ is hydrogen; and
q is zero.

11. A compound according to claim 1, wherein:
W is $R^1$;
$R^1$ is $R^2CF_2C(R^{12})_2(CH_2)_q$;
$R^2$ is aryl or pyridyl, each of which is optionally substituted with halogen, alkyl or $SO_2$ alkyl;
$R^{12}$ is hydrogen; and
q is zero.

12. A compound according to claim 1, wherein $R^3$ is halogen.

13. A compound according to claim 12, wherein $R^3$ is chloro or fluoro.

14. A compound according to claim 13, wherein $R^3$ is fluoro and $R^4$ and $R^5$ are hydrogen.

15. A compound according to claim 1, wherein $R^{11}$ is hydrogen.

16. A compound according to claim 1, wherein $R^a$, $R^b$, $R^c$ and $R^{13}$ are each hydrogen.

17. A compound according to claim 1, wherein each of $R^7$, $R^8$, $R^9$ and $R^{10}$ are hydrogen.

18. A compound according to claim 1, wherein $R^6$ is cyano.

19. A compound according to claim 18, wherein $R^3$ is halogen.

20. A compound according to claim 19, wherein $R^3$ is fluoro while $R^4$ is hydrogen or fluoro and $R^5$ is hydrogen.

21. A compound which is one of:
N-[2-(Amidinoaminooxy)ethyl]-2-{3-[(2,2-difluoro-2-(5-methyl pyridyl)ethyl)amino]-6-cyano-2-fluorophenyl}acetamide;
N-[2-(Amidinoaminooxy)ethyl]-2-{3-[2-(3-chlorophenyl)-2,2-difluoro ethylamino]-6-cyano-2-fluorophenyl}acetamide;

N-[2-(Amidinoaminooxy)ethyl]-2-{3-[(2,2-difluoro-2-(4-methyl pyridyl)ethyl)amino]-6-cyano-2-fluorophenyl}acetamide;

N-[2-(Amidinoaminooxy)ethyl]-2-{3-[(2,2-difluoro-2-(6-methyl pyridyl)ethyl)amino]-6-cyano-2-fluorophenyl}acetamide;

N-[2-(Amidinoaminooxy)ethyl]-2-{3-[(2,2-difluoro-2-(3-methyl pyridyl)ethyl)amino]-6-cyano-2-fluorophenyl}acetamide;

N-[2-(Amidinoaminooxy)ethyl]-2-{3-[(2,2-difluoro-2-(quinolin-8-yl)ethyl)amino]-6-cyano-2-fluorophenyl}acetamide;

N-(6-Amino-2-methyl-pyridin-3-ylmethyl)-2-[6-cyano-3-(2,2-difluoro-2-pyridin-2-yl-ethylamino)-2-fluoro-phenyl]-acetamide;

N-(6-Amino-pyridin-3-ylmethyl)-2-[6-cyano-3-(2,2-difluoro-2-pyridin-2-yl-ethylamino)-2-fluoro-phenyl]-acetamide;

N-[2-(Amidinoaminooxy)ethyl]-2-{3-[(2,2-difluoro-2-pyridyl ethyl)amino]-6-cyano-2-fluorophenyl}acetamide;

N-[2-(Amidinoaminooxy)ethyl]-2-{3-[(2,2-difluoro-2-phenyl ethyl)amino]-6-cyano-2-fluorophenyl}acetamide;

N-[2-(Amidinoaminooxy)ethyl]-2-{3-[(2,2-difluoro-2-(3-fluoro phenyl)ethyl)amino]-6-cyano-2-fluorophenyl}acetamide;

N-[2-(Amidinoaminooxy)ethyl]-2-{3-[(2,2-difluoro-2-(3,4-difluoro phenyl)ethyl)amino]-6-cyano-2-fluorophenyl}acetamide;

N-[2-(Amidinoaminooxy)ethyl]-2-{3-[(2,2-difluoro-2-(5-chloro-pyridin-2-yl)ethyl)amino]-6-cyano-2-fluorophenyl}acetamide;

N-[2-(Amidinoaminooxy)ethyl]-2-{3-[(2,2-difluoro-2-(2-methanesulfonylphenyl)ethyl)amino]-6-cyano-2-fluorophenyl}acetamide;

N-[2-(Amidino-N-methyl-aminooxy)ethyl]-2-{3-[(2,2-difluoro-2-pyridyl-ethyl)amino]-6-cyano-2-fluorophenyl}acetamide;

or a pharmaceutically acceptable salt thereof.

22. A pharmaceutical composition, comprising a compound of claim 1 and a pharmaceutically-acceptable carrier.

23. A pharmaceutical composition, comprising a compound of claim 2 and a pharmaceutically-acceptable carrier.

24. A pharmaceutical composition, comprising a compound of claim 5 and a pharmaceutically-acceptable carrier.

25. A pharmaceutical composition, comprising a compound of claim 7 and a pharmaceutically-acceptable carrier.

26. A pharmaceutical composition, comprising a compound of claim 9 and a pharmaceutically-acceptable carrier.

27. A pharmaceutical composition, comprising a compound of claim 18 and a pharmaceutically-acceptable carrier.

28. A pharmaceutical composition, comprising a compound of claim 19 and a pharmaceutically-acceptable carrier.

29. A pharmaceutical composition, comprising a compound of claim 21 and a pharmaceutically-acceptable carrier.

30. A pharmaceutical composition according to claim 22, further comprising at least one of an anticoagulant, an antiplatelet agent or a thrombolytic agent.

31. A pharmaceutical composition according to claim 22, wherein said compound is present in an amount between about 0.1 and about 500 mg.

32. A method of treating thrombosis, or ischemia in a mammal in need thereof, comprising administering to said mammal an effective amount of a compound of claim 1.

33. A pharmaceutical composition according to claim 23, further comprising at least one of an anticoagulant, an antiplatelet agent or a thrombolytic agent.

34. A pharmaceutical composition according to claim 23, wherein said compound is present in an amount between about 0.1 and about 500 mg.

35. A pharmaceutical composition according to claim 22 adapted for oral administration.

36. A pharmaceutical composition according to claim 23 adapted for oral administration.

37. A pharmaceutical composition according to claim 24 adapted for oral administration.

38. A pharmaceutical composition according to claim 25 adapted for oral administration.

39. A pharmaceutical composition according to claim 26 adapted for oral administration.

40. A pharmaceutical composition according to claim 27 adapted for oral administration.

41. A pharmaceutical composition according to claim 28 adapted for oral administration.

42. A pharmaceutical composition according claim to 29 adapted for oral administration.

* * * * *

UNITED STATES PATENT AND TRADEMARK OFFICE
CERTIFICATE OF CORRECTION

| | | |
|---|---|---|
| PATENT NO. | : 7,550,474 B2 | Page 1 of 1 |
| APPLICATION NO. | : 10/816544 | |
| DATED | : June 23, 2009 | |
| INVENTOR(S) | : Kreutter et al. | |

It is certified that error appears in the above-identified patent and that said Letters Patent is hereby corrected as shown below:

Title Page, Item (73) Assignee:
Line 1, delete "Pharmaceuticals" and insert -- Pharmaceutical --.

Column 5,
Lines 60 and 61, delete "$C_{1-2}$" and insert -- $C_{1-12}$ --.

Column 38,
Line 50, delete "(11.6 μL)" and insert -- (11.6 mL) --.

Column 41,
Line 67, delete "t,J=8.47 Hz, H)" and insert -- t,J=8.47 Hz, 1H --.

Column 65,
Claim 1, line 31, delete "$R^2(CH_2)_1$" and insert -- $R^2(CH_2)_t$ --.

Signed and Sealed this
Eighteenth Day of October, 2011

David J. Kappos
*Director of the United States Patent and Trademark Office*